US008846661B2

(12) United States Patent
Schrimpf et al.

(10) Patent No.: US 8,846,661 B2
(45) Date of Patent: Sep. 30, 2014

(54) DIAZAHOMOADAMANTANE DERIVATIVES AND METHODS OF USE THEREOF

(75) Inventors: Michael R. Schrimpf, Grayslake, IL (US); Kevin B. Sippy, Antioch, IL (US)

(73) Assignee: AbbVie Inc., North Chicago, IL (US)

( * ) Notice: Subject to any disclaimer, the term of this patent is extended or adjusted under 35 U.S.C. 154(b) by 500 days.

(21) Appl. No.: 12/818,764

(22) Filed: Jun. 18, 2010

(65) Prior Publication Data
US 2010/0324027 A1 Dec. 23, 2010

Related U.S. Application Data

(60) Provisional application No. 61/218,479, filed on Jun. 19, 2009.

(51) Int. Cl.
*A61K 31/55* (2006.01)
*C07D 487/00* (2006.01)
*C07D 487/18* (2006.01)
*C07D 471/18* (2006.01)

(52) U.S. Cl.
CPC .................................. *C07D 471/18* (2013.01)
USPC ........................... 514/220; 540/496; 540/556

(58) Field of Classification Search
None
See application file for complete search history.

(56) References Cited

U.S. PATENT DOCUMENTS

| | | | | |
|---|---|---|---|---|
| 7,067,507 B2 * | 6/2006 | Pulley et al. | .................. | 514/183 |
| 2012/0277216 A1 * | 11/2012 | Nirogi et al. | .................. | 514/215 |

FOREIGN PATENT DOCUMENTS

| | | |
|---|---|---|
| EP | 1125922 A1 | 8/2001 |
| WO | 2008058096 A2 | 5/2008 |
| WO | 2008118743 A1 | 10/2008 |
| WO | 2008118747 A1 | 10/2008 |
| WO | 2011030349 A1 | 3/2011 |

OTHER PUBLICATIONS

Jantzen. Modern Pharmaceutics, 1996, p. 596.*
Cassels. Drug Discovery Today, 2005, 10 (23/24), 1657-1665.*
Adams C. E., et al. "Development of the α7 nicotinic cholinergic receptor in rat hippocampal formation", Dev. Brain Res., 2002, 139, 175-187.
Alkondon, et al., "The nicotinic acetylcholine receptor subtypes and their function in the hippocampus and cerebral cortex", Prog. Brain Res., 2004, 145, 109-120.
Anderson J., et al., "[3H]A-585539 [(1S,4S)-2,2-dimethyl-5-(6-phenylpyridazin-3-yl)-5-aza-2-azoniabicyclo[2.2.1]heptane], a novel high-affinity alpha7 neuronal nicotinic receptor agonist: radioligand binding characterization to rat and human brain", Journal of Pharm. and Exp. Therap., 2008, 324 (1), 179-187.
Balbani A., et al., "Recent developments for smoking cessation and treatment of nicotine dependence", Expert. Opin. Ther. Pat., 2007, 17 (3), 287-297.
Bitner R., et al. "Alpha-7 nAChR-mediated regulation of GSK3 and tau phosphorylation: potential for disease modification in Alzheimer's disease", 2007, Society of Neuroscience.
Broad L. M., et al., "Selective alpha7 nicotinic acetylcholine receptor ligands for the treatment of neuropsychiatric diseases", Drugs of the Future, 2007, 32 (2), 161-170.
Bunnelle W. H., et al., "Neuronal nicotinic acetylcholine receptor ligands as potential analgesics", Expert Opin. Ther. Patents, 2003, 13 (7), 1003-1021.
Couturier S., et al., "A Neuronal Nicotinic Acetylcholine Receptor Subunit (alpha7) Is Developmentally Regulated and forms a Homo-Oligomeric Channel Blocked by alpha-BTX", Neuron, 1990, 5, 847-856.
Dajas Bailador F., et al., "Nicotinic acetylcholine receptors and the regulation of neuronal signalling", TRENDS in Pharm. Sci., 2004, 25 (6), 317-324.
De Luca V., et al., "Regulation of alpha7-nicotinic receptor subunit and alpha7-like gene expression in the prefrontal cortex of patients with bipolar disorder and schizophrenia", Acta Psychiatr. Scand., 2006, 114, 211-215.
Decker M. W., et al., "The therapeutic potential of nicotinic acetylcholine receptor agonists for pain control", Expert Opin. Investig. Drugs, 2001, 10 (10), 1819-1830.
Falk, et al., "Higher expression of .alpha.7 nicotinic acetylcholine receptors in human fetal compared to adult brain", Developmental Brian Research, 2003, 142, 151-160.
Gotti Clementi "Neuronal nicotinic receptors: from structure to pathology", Progress in Neurobiology, 2004, 74, 363-396.
Gundish D. "Nicotinic acetylcholine receptor ligands as potential therapeutics", Expert Opin. Ther. Patents, 2005, 15 (9), 1221-1239.
Gurwitz D. "The therapeutic potential of nicotine and nicotinic agonists for weight control", Exp. Opin. Invest. Drugs, 1999, 8 (6), 747-760.
Hogg, et al. "Nicotinic acetylcholine receptors: From structure to brain function", Rev. Physiol Biochem. Pharmacol., 2003, 147, 1-46.
Jonnala, et al. "Relationship between the increased cell surface .alpha.7 nicotinic receptor expression and neuroprotection induced by several nicotinic receptor agonists", Journal of Neuroscience Research, 2001, 66, 565-572.
Keller, et al. "Performance of alpha7 nicotinic receptor null mutants is impaired in appetitive learning measured in a signaled nose poke task", Behay. Brain Res., 2005, 162, 143-152.
Kihara, et al. "alpha.7 Nicotinic receptor transduces signals to phosphastidylinositol 3-kinase to block A .beta.-amyloid-induced neurotoxicity", Journal of Biological Chemistry, 2001, 276 (17), 13541-13546.
Levin E. D. "Nicotinic Receptor Subtypes and Cognitive Function", J Neurobiol 2002, 53, 633-640.
Liu, et al. "alpha.-Amyloid peptide blocks the response of .alpha.7-containing nicotinic receptors on hippocampal neurons", PNAS, 2001, 98 (8), 4734-4739.
Pabreza, et al. "[.sup.3H]cytosine binding to nicotinic cholinergic receptors in brain", Molecular Pharmacology, 1990, 39, 9-12.
Paterson, D., et al. "Neuronal nicotinic receptors in the human brain", Progress in Neurobiology, 2000, 61, 75-111.
Sawa, et al. "Schizophrenia: neural mechanisms for novel therapies", Mol. Med, 2003, 9, 3-9.
Shimohama, et al. "Nicotinic .alpha.7 receptors protect against glutamate neurotoxicity and neuronal ischemic damage", Brain Research, 1998, 779, 359-363.

(Continued)

*Primary Examiner* — Andrew D Kosar
*Assistant Examiner* — John S Kenyon
(74) *Attorney, Agent, or Firm* — Lisa V. Mueller; Michael Best & Friedrich LLP

(57) ABSTRACT

The invention relates to compounds that are diazahomoadamantane derivatives, compositions comprising such compounds, and methods of using such compounds and compositions.

20 Claims, No Drawings

(56) References Cited

OTHER PUBLICATIONS

Tsuneki H., et al. "Mouse muscle denervation increases expression of an a7 nicotinic receptor with unusual pharmacology", J. Physiol, 2003, 547 (1), 169-179.

Vincler M. "Neuronal nicotinic receptors as targets for novel analgesics", Expert Opin. Investig. Drugs 2005, 14 (10), 1191-1198.

Vincler M. "Targeting the alpha9alpha10 nicotinic acetylcholine receptor to treat severe pain", Expert Opin. Ther. Targets 2007, 11 (7), 891-897.

Wilens T. E., et al. "A pilot controlled clinical trial of ABT-418, a cholinergic agonist, in the treatment of adults with attention deficit hyperactivity disorder", American Journal of Psychiatry, 1999, 156 (12), 1931-1937.

Extended European Search Report for Application No. EP10788604, mailed on Nov. 21, 2012, 6 pages.

International Preliminary Report on Patentability and Written Opinion for Application No. PCT/CN2010/000889, mailed on Dec. 20, 2011, 7 pages.

International Search Report for Application No. PCT/CN2010/000889, mailed on Sep. 23, 2010, 4 pages.

* cited by examiner

DIAZAHOMOADAMANTANE DERIVATIVES AND METHODS OF USE THEREOF

CROSS-REFERENCE TO RELATED APPLICATIONS

This patent application claims priority to U.S. Provisional Patent Application No. 61/218,479, filed on Jun. 19, 2009, the entirety of which is incorporated herein by reference.

TECHNICAL FIELD

The invention relates to diazahomoadamantane derivatives, compositions comprising such compounds, methods of preventing or treating conditions and disorders using such compounds and compositions, processes for preparing such compounds, and intermediates obtained during such processes.

DESCRIPTION OF RELATED TECHNOLOGY

Nicotinic acetylcholine receptors (nAChRs), belonging to the super family of ligand gated ion channels (LGIC), are widely distributed throughout the central nervous system (CNS) and the peripheral nervous system (PNS), and gate the flow of cations, controlled by acetylcholine (ACh). The nAChRs can be divided into nicotinic receptors of the muscular junction (NMJ) and neuronal nAChRs or neuronal nicotinic receptors (NNRs). The NNRs are understood to play an important role in regulating CNS function and the release of many neurotransmitters, including, but not necessarily limited to acetylcholine, norepinephrine, dopamine, serotonin and GABA. Consequently, nicotinic receptors mediate a very wide range of physiological effects, and have been targeted for therapeutic treatment of disorders relating to cognitive function, learning and memory, neurodegeneration, pain and inflammation, psychosis and sensory gating, mood and emotion, among others.

Many subtypes of NNRs exist in the CNS and periphery. Each subtype has a different effect on regulating the overall physiological function.

Typically, NNRs are ion channels that are constructed from a pentameric assembly of subunit proteins. Sixteen subunits of nAChRs have been reported to date, which are identified as $\alpha 2$-$\alpha 10$, $\beta 1$-$\beta 4$, $\gamma$, $\delta$, and $\epsilon$. Of these subunits, nine subunits, $\alpha 2$ through $\alpha 7$ and $\beta 2$ through $\beta 4$, prominently exist in the mammalian brain. Multiple functionally distinct nAChR complexes also exist, for example five $\alpha 7$ subunits can form a receptor as a homomeric functional pentamer or combinations of different subunits can complex together as in the case of $\alpha 4\beta 2$ and $\alpha 3\beta 4$ receptors (see for example, Vincler, M., et al., Exp. Opin. Ther. Targets, 2007, 11: 391-897; Paterson, D., et al., Prog. Neurobiol. 2000, 61: 75-111; Hogg, R. C., et al., Rev. Physiol., Biochem. Pharmacol., 2003, 147: 1-46; Gotti, C., et al., Prog. Neurobiol., 2004, 74: 363-396). These subunits provide for a great variety of homomeric and heteromeric combinations that account for the diverse receptor subtypes.

The NNRs, in general, are involved in various cognitive functions, such as learning, memory, attention, and therefore in CNS disorders, i.e., Alzheimer's disease (AD), Parkinson's disease (PD), attention deficit hyperactivity disorder (ADHD), Tourette's syndrome, schizophrenia, bipolar disorder, pain, and tobacco dependence (see for example, Keller, J. J., et al., Behav. Brain Res., 2005, 162: 143-52; Gundish, D., Expert Opin. Ther. Patents, 2005, 15 (9): 1221-1239; De Luca, V., et al., Acta Psychiatr. Scand., 2006, 114: 211-5).

The homomeric $\alpha 7$ receptor is one of the most abundant nicotinic receptors, along with $\alpha 4\beta 2$ receptors, in the human brain, wherein it is heavily expressed in the hippocampus, cortex, thalamic nuclei, ventral tegmental area and substantia nigra (see for example, Broad, L. M., et al., Drugs of the Future, 2007, 32: 161-170).

The role of $\alpha 7$ NNRs in neuronal signaling in the CNS also has been actively investigated (see for example, Couturier, S., et al., Neuron, 1990, 5: 847-56). The $\alpha 7$ NNRs have been demonstrated to regulate interneuron excitability, modulate the release of excitatory and inhibitory neurotransmitters, and lead to neuroprotective effects in experimental in vitro models of cellular damage (see for example, Alkondon, M., et al., Prog. Brain Res., 2004, 145: 109-20).

Biophysical studies have shown that ion channels comprised of $\alpha 7$ subunits, when expressed in heterologous expression systems, activate and desensitize rapidly, and furthermore, exhibit relatively higher calcium permeability compared to other NNR combinations (see for example, Dajas-Bailador, F., et al., Trends Pharmacol. Sci., 2004, 25: 317-24).

The NNR ligands have been also implicated in smoking cessation, weight control and as potential analgesics (see for example, Balbani, A. P. S., et al, Exp. Opin. Ther. Patents, 2003, 13: 287-297; Gurwitz, D., Exp. Opin. Invest. Drugs, 1999, 8: 747-760; Vincler, M., Exp. Opin. Invest. Drugs, 2005, 14: 1191-1198; Bunnelle, W. H., et al., Exp. Opin. Ther. Patents, 2003, 13: 1003-1021; Decker, M. W., et al., Exp. Opin. Invest. Drugs, 2001, 10: 1819-1830; Vincler, M., et al., Exp. Opin. Ther. Targets, 2007, 11: 891-897).

The $\alpha 7$ and $\alpha 4\beta 2$ NNRs have been shown to play a significant role in enhancing cognitive function, including aspects of learning, memory and attention (Levin, E. D., J. Neurobiol. 2002, 53: 633-640). For example, $\alpha 7$ NNRs have been linked to conditions and disorders related to attention deficit disorder, ADHD, AD, mild cognitive impairment, senile dementia, dementia associated with Lewy bodies, dementia associated with Down's syndrome, AIDS dementia, Pick's disease, as well as cognitive deficits associated with schizophrenia (CDS), among other systemic activities. The $\alpha 4\beta 2$ receptor subtype is implicated in attention, cognition, epilepsy, and pain control (Paterson, D., et al., Prog. Neurobiol. 2000, 61: 75-111).

Certain compounds, like the plant alkaloid nicotine, interact with all known subtypes of the nAChRs, accounting for the profound physiological effects of this compound. Nicotine is known to provide enhanced attention and cognitive performance, reduced anxiety, enhanced sensory gating, and analgesia and neuroprotective effects when administered. Such effects are mediated by the non-selective effect of nicotine at a variety of nicotinic receptor subtypes. However, nicotine also produces adverse consequences, such as cardiovascular and gastrointestinal problems that interfere at therapeutic doses, and its addictive nature and acute toxicity are well-known. Accordingly, there is a need to identify subtype-selective compounds that evoke the beneficial effects of nicotine while eliminating or decreasing adverse effects.

Pain is the most common symptom of disease and the most frequent complaint with which patients present to physicians. Pain is commonly segmented by duration (acute vs. chronic), intensity (mild, moderate, and severe), and type (nociceptive vs. neuropathic).

Nociceptive pain is the most well known type of pain, and is caused by tissue injury detected by nociceptors at the site of injury. After the injury, the site becomes a source of ongoing pain and tenderness. Nociceptive pain can be experienced as sharp, dull, or aching. This pain and tenderness are considered "acute" nociceptive pain. This pain and tenderness gradually diminish as healing progresses and disappear when healing is complete. Examples of acute nociceptive pain include surgical procedures (post-op pain), burns, ocular pain, inflammation (due to infection or arthritis) and bone fractures. Even though there may be no permanent nerve damage, "chronic" nociceptive pain results from some conditions when pain extends beyond six months. Examples of chronic nociceptive pain include osteoarthritis, rheumatoid arthritis, and musculoskeletal conditions (e.g., back pain), cancer pain, etc.

Neuropathic pain is defined as "pain initiated or caused by a primary lesion or dysfunction in the nervous system" by the International Association for the Study of Pain. Neuropathic pain may refer to peripheral neuropathic pain, which is caused by damage to nerves, or to central neuropathic pain, which is caused by damage to the brain, brainstem, or spinal cord. Neuropathic pain is not associated with nociceptive stimulation, although the passage of nerve impulses that is ultimately perceived as pain by the brain is the same in both nociceptive and neuropathic pain. The term neuropathic pain encompasses a wide range of pain syndromes of diverse etiologies. The three most commonly diagnosed pain types of neuropathic nature are diabetic neuropathy, cancer neuropathy, and HIV pain. In addition, neuropathic pain is diagnosed in patients with a wide range of other disorders, including fibromyalgia, trigeminal neuralgia, post-herpetic neuralgia, traumatic neuralgia, phantom limb, headaches, as well as a number of other disorders of ill-defined or unknown origin.

Pain is an unmet medical need and the methods and possibilities for treatments of such indications are insufficient. Although continued efforts are being made to treat pain using nAChR agonists, robust efficacy in pain may be limited by the range of side effects associated with their use, albeit to differing degrees. In light of the significance of chronic pain and the limitations in their treatment, it would be beneficial to identify new methods of treating such disorders, particularly in a manner that reduces adverse ganglionic effects such as at the gastrointestinal systems (e.g. emesis). It would be particularly beneficial to identify compounds and compositions that offer an opportunity to widen the therapeutic window of nicotinic (nAChR) agonists in pain. Enhanced efficacy with nAChR ligands for the treatment of other central nervous system diseases such as cognitive and attention deficits is also desirable.

The activity at the NNRs can be modified or regulated by the administration of subtype selective NNR ligands. The ligands can exhibit antagonist, agonist, or partial agonist properties and thus have potential in treatment of various cognitive disorders.

Although compounds that nonselectively demonstrate activity at a range of nicotinic receptor subtypes including the α4β2 and α7 NNRs are known, it would be beneficial to provide compounds that interact selectively with α7-containing neuronal NNRs, α4β2 NNRs, or both α7 and α4β2 NNRs compared to other subtypes.

SUMMARY OF THE INVENTION

The invention is directed to diazahomoadamantane derivatives, compositions comprising such compounds, and methods of using such compounds and compositions.

One aspect of the invention relates to a compound of formula (I)

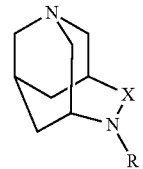

(I)

wherein
X is $CH_2$ or C=O;
R is hydrogen, $Ar^1$, $Ar^2$—$Ar^3$, —$(CH_2)_q Ar^3$, —C(O)$Ar^3$, —C(O)O$Ar^3$, —C(O)N$R^1 R^2$, —C(O)—$(CR^x R^y)_q$—$Ar^3$, —C(O)—$(CR^x R^y)_q$—O—$Ar^3$, —C(O)—$Ar^2$—$Ar^3$, or (i);

(i)

$Ar^1$, $Ar^2$, and $Ar^3$ are each independently aryl or heteroaryl;
A is aryl or heteroaryl;
q is 1, 2, 3, 4, or 5;
r and s are independently 0, 1, 2, or 3, wherein the total of r and s is 2, 3 or 4;
$R^1$ is hydrogen or alkyl;
$R^2$ is aryl, arylalkyl, heteroaryl, or heteroarylalkyl;
$R^x$ and $R^y$, at each occurrence, are each independently hydrogen, alkyl, fluorine, or haloalkyl;
wherein each aryl or heteroaryl or the aryl and heteroaryl moieties on arylalkyl and heteroarylalkyl groups are independently unsubstituted or substituted with 1, 2, 3, 4, or 5 substituents selected from the group consisting of alkyl, alkenyl, alkynyl, halogen, cyano, -$G^1$, —$NO_2$, —$OR^{1a}$, —O—$(CR^{4a}R^{5a})_p$—O—, —OC(O)$R^{1a}$, —OC(O)N($R^b$)($R^{3a}$), —$SR^{1a}$, —S(O)$_2 R^{2a}$, —S(O)$_2$N($R^b$)($R^{3a}$), —C(O)$R^{1a}$, —C(O)O$R^{1a}$, —C(O)N($R^b$)($R^{3a}$), —N($R^b$)($R^{3a}$), —N($R^a$)C(O)$R^{1a}$, —N($R^a$)C(O)O($R^{1a}$), —N($R^a$)C(O)N($R^b$)($R^{3a}$), —$(CR^{4a}R^{5a})_m$—$NO_2$, —$(CR^{4a}R^{5a})_m$—$OR^{1a}$, —$(CR^{4a}R^{5a})_m$—OC(O)$R^{1a}$, —$(CR^{4a}R^{5a})_m$—OC(O)N($R^b$)($R^{3a}$), —$(CR^{4a}R^{5a})_m$—$SR^{1a}$, —$(CR^{4a}R^{5a})_m$—S(O)$_2 R^{2a}$, —$(CR^{4a}R^{5a})$S(O)$_2$N($R^b$)($R^{3a}$), —$(CR^{4a}R^{5a})_m$—C(O)$R^{1a}$, —$(CR^{4a}R^{5a})_m$—C(O)O$R^{1a}$, —$(CR^{4a}R^{5a})_m$—C(O)N($R^b$) ($R^{3a}$), —$(CR^{4a}R^{5a})_m$—N($R^b$)($R^{3a}$), —$(CR^{4a}R^{5a})_m$—N($R^a$)C (O)$R^{1a}$, —$(CR^{4a}R^{5a})_m$—N($R^a$)C(O)O($R^{1a}$), —$(CR^{4a}R^{5a})_m$—N($R^a$)C(O)N($R^b$)($R^{3a}$), —$(CR^{4a}R^{5a})_m$-$G^2$, cyanoalkyl, and haloalkyl; wherein
$R^{1a}$ and $R^{3a}$, at each occurrence, are each independently hydrogen, alkyl, haloalkyl, $G^2$, or —$(CR^{6a}R^{7a})_n$-$G^2$;
$R^{2a}$, at each occurrence, is independently alkyl, haloalkyl, $G^2$, or —$(CR^{6a}R^{7a})_n$-$G^2$;
$R^{4a}$, $R^{5a}$, $R^{6a}$, and $R^{7a}$, at each occurrence, are each independently hydrogen, halogen, alkyl, or haloalkyl;
$R^a$ and $R^b$, at each occurrence, are each independently hydrogen, alkyl, or haloalkyl;
m and n, at each occurrence, are each independently 1, 2, 3, 4, or 5;
p, at each occurrence, is 1 or 2; —O—$(CR^{4a}R^{5a})_p$—O— is divalent substituent attached to two adjacent carbon atoms of the aryl or heteroaryl;
$G^1$, at each occurrence, is heterocycle or cycloalkyl, wherein each $G^1$ is independently unsubstituted or substituted with 1, 2, 3, 4, or 5 substituents selected from the group consisting of alkyl, alkenyl, alkynyl, halogen, cyano, oxo, —$NO_2$, —$OR^{1b}$, —$OC(O)R^{1b}$, —OC(O)N($R^b$)($R^{3b}$), —$SR^{1b}$, —$S(O)_2N(R^b)(R^{3b})$, —$C(O)OR^{1b}$, —$C(O)N(R^b)(R^{3b})$, —$N(R^b)(R^{3b})$, —$N(R^a)C(O)R^{1b}$, —$N(R^a)C(O)O(R^{1b})$, —$N(R^a)C(O)N(R^b)(R^{3b})$, —$(CR^{4b}R^{5b})_m$—$NO_2$, —$(CR^{4b}R^{5b})_m$—$OR^{1b}$, —$(CR^{4b}R^{5b})_m$—$OC(O)R^{1b}$, —$(CR^{4b}R^{5b})_m$—OC(O)N($R^b$)($R^{3b}$), —$(CR^{4b}R^{5b})_m$—$SR^{1b}$, —$(CR^{4b}R^{5b})_m$—$S(O)_2R^{2b}$, —$(CR^{4b}R^{5b})_m$—$S(O)_2N(R^b)(R^{3b})$, —$(CR^{4b}R^{5b})_m$—$C(O)R^{1b}$—$(CR^{4b}R^{5b})_m$—C(O)$OR^{1b}$—$(CR^{4b}R^{5b})_m$—$C(O)N(R^b)(R^{3b})$, —$(CR^{4b}R^{5b})_m$—$N(R^b)(R^{3b})$, —$(CR^{4b}R^{5b})_m$—$N(R^a)C(O)R^{1b}$, —$(CR^{4b}R^{5b})_m$—$N(R^a)C(O)O(R^{1b})$, —$(CR^{4b}R^{5b})_m$—$N(R^a)C(O)N(R^b)(R^{3b})$, cyanoalkyl, and haloalkyl;

$R^{1b}$ and $R^{3b}$, at each occurrence, are each independently hydrogen, alkyl, or haloalkyl;

$R^{2b}$, at each occurrence, is independently alkyl or haloalkyl; and $R^{4b}$ and $R^{5b}$, at each occurrence, are each independently hydrogen, halogen, alkyl, or haloalkyl;

$G^2$, at each occurrence, is aryl, heteroaryl, heterocycle, or cycloalkyl, wherein each $G^2$ is independently unsubstituted or substituted with 1, 2, 3, 4, or 5 substituents selected from the group consisting of alkyl, alkenyl, alkynyl, halogen, cyano, oxo, —$NO_2$, —$OR^{1b}$, —OC(O)$R^{1b}$, —OC(O)N($R^b$)($R^{3b}$), —$SR^{1b}$, —$S(O)_2R^{2b}$, —$S(O)_2N(R^b)(R^{3b})$, —$C(O)R^{1b}$, —$C(O)OR^{1b}$, —$C(O)N(R^b)(R^{3b})$, —$N(R^b)(R^{3b})$, —$N(R^a)C(O)R^{1b}$, —$N(R^a)C(O)O(R^{1b})$, —$N(R^a)C(O)N(R^b)(R^{3b})$, —$(CR^{4b}R^{5b})_m$—$NO_2$, —$(CR^{4b}R^{5b})_m$—$OR^{1b}$, —$(CR^{4b}R^{5b})_m$—OC(O)$R^{1b}$, —$(CR^{4b}R^{5b})_m$—OC(O)N($R^b$)($R^{3b}$), —$(CR^{4b}R^{5b})_m$—$SR^{1b}$, —$(CR^{4b}R^{5b})_m$—$S(O)_2R^{2b}$, —$(CR^{4b}R^{5b})_m$—$S(O)_2N(R^b)(R^{3b})$, —$(CR^{4b}R^{5b})_m$—$C(O)R^{1b}$, —$(CR^{4b}R^{5b})_m$—$C(O)OR^{1b}$, —$(CR^{4b}R^{5b})_m$—$C(O)N(R^b)(R^{3b})$, —$(CR^{4b}R^{5b})_m$—$N(R^b)(R^{3b})$, —$(CR^{4b}R^{5b})_m$—$N(R^a)C(O)R^{1b}$, —$(CR^{4b}R^{5b})_m$—$N(R^a)C(O)O(R^{1b})$, —$(CR^{4b}R^{5b})_m$—$N(R^a)C(O)N(R^b)(R^{3b})$, cyanoalkyl, and haloalkyl;

or a pharmaceutically acceptable salt, amide, ester or prodrug thereof.

Another aspect of the invention relates to pharmaceutical compositions comprising compounds of the invention. Such compositions can be administered in accordance with a method of the invention, typically as part of a therapeutic regimen for treatment or prevention of conditions and disorders related to NNR activity, and more particularly α7 NNR activity, α4β2 NNR activity, or both α7 NNR activity and α4β2 NNR activity.

A further aspect of the invention relates to a method of modulating α7 NNR activity, α4β2 NNR activity, or both α7 NNR activity and α4β2 NNR activity. The method is useful for treating, preventing, or both treating and preventing conditions and disorders related to α7 NNR activity, α4β2 NNR activity, or both α7 NNR activity and α4β2 NNR activity in mammals. More particularly, the method is useful for conditions and disorders related to attention deficit disorder, ADHD, AD, Parkinson's disease, Tourette's syndrome, schizophrenia, cognitive deficits of schizophrenia (CDS), mild cognitive impairment, age-associated memory impairment (AAMI), senile dementia, AIDS dementia, Pick's disease, dementia associated with Lewy bodies, dementia associated with Down's syndrome, amyotrophic lateral sclerosis, Huntington's disease, diminished CNS function associated with traumatic brain injury, acute pain, chronic pain, neuropathic pain, nociceptive pain, allodynia, inflammatory pain, inflammatory hyperalgesia, post herpetic neuralgia, neuropathies, neuralgia, diabetic neuropathy, HIV-related neuropathy, nerve injury, rheumatoid arthritic pain, osteoarthritic pain, burns, back pain, eye pain, visceral pain, cancer pain, dental pain, headache, migraine, carpal tunnel syndrome, fibromyalgia, neuritis, sciatica, pelvic hypersensitivity, pelvic pain, post operative pain, post stroke pain, menstrual pain, smoking cessation, ischemia, sepsis, wound healing, and other complications associated with diabetes, among other systemic and neuroimmunomodulatory activities.

This invention provides methods and compositions for inducing, promoting or otherwise facilitating pain relief. In one embodiment, the present invention relates to methods for treating or preventing pain, including nociceptive and/or neuropathic pain in mammals, and particularly in humans, comprising: (i) administering a nicotinic acetylcholine receptor ligand; and (ii) administering a nicotinic acetylcholine receptor subtype α4β2 allosteric modulator to the mammal in an amount effective to treat the pain. More particularly, the present method relates to the treatment of osteoarthritis pain by administering a therapeutically effective amount of a nicotinic acetylcholine receptor subtype α4β2 allosteric modulator, or a salt thereof, in combination with a nicotinic acetylcholine receptor ligand, or a salt thereof, to a subject in need of treatment.

The compounds, compositions comprising the compounds, methods for using the compounds, and processes for preparing the compounds, as well as intermediates obtained in such processes, are further described herein.

DETAILED DESCRIPTION

In another aspect, the present invention relates to composition comprising compounds having a formula (I) as described above and at least one pharmaceutically acceptable carrier.

In still yet another aspect, the present invention relates to methods for preventing and treating disease conditions, such as attention deficit disorder, ADHD, AD, Parkinson's disease, Tourette's syndrome, schizophrenia, cognitive deficits of schizophrenia (CDS), mild cognitive impairment, age-associated memory impairment (AAMI), senile dementia, AIDS dementia, Pick's disease, dementia associated with Lewy bodies, dementia associated with Down's syndrome, amyotrophic lateral sclerosis, Huntington's disease, diminished CNS function associated with traumatic brain injury, acute pain, acute pain, chronic pain, neuropathic pain, nociceptive pain, allodynia, inflammatory pain, inflammatory hyperalgesia, post herpetic neuralgia, neuropathies, neuralgia, diabetic neuropathy, HIV-related neuropathy, nerve injury, rheumatoid arthritic pain, osteoarthritic pain, burns, back pain, eye pain, visceral pain, cancer pain, dental pain, headache, migraine, carpal tunnel syndrome, fibromyalgia, neuritis, sciatica, pelvic hypersensitivity, pelvic pain, post operative pain, post stroke pain, menstrual pain, smoking cessation, ischemia, sepsis, wound healing, and other complications associated with diabetes, among other systemic and neuroimmunomodulatory activities, using compounds having a formula of formula (I) as described above.

In still yet another aspect, the present invention relates to the use of compounds having a formula (I) in the manufacture of a medicament for the prevention or treatment of the disease conditions, such as attention deficit disorder, ADHD, AD, Parkinson's disease, Tourette's syndrome, schizophrenia, cognitive deficits of schizophrenia (CDS), mild cognitive impairment, age-associated memory impairment (AAMI), senile dementia, AIDS dementia, Pick's disease, dementia associated with Lewy bodies, dementia associated with Down's syndrome, amyotrophic lateral sclerosis, Huntington's disease, diminished CNS function associated with traumatic brain injury, acute pain, acute pain, chronic pain, neuropathic pain, nociceptive pain, allodynia, inflammatory pain, inflammatory hyperalgesia, post herpetic neuralgia, neuropathies, neuralgia, diabetic neuropathy, HIV-related neuropathy, nerve injury, rheumatoid arthritic pain, osteoarthritic pain, burns, back pain, eye pain, visceral pain, cancer pain, dental pain, headache, migraine, carpal tunnel syndrome, fibromyalgia, neuritis, sciatica, pelvic hypersensitivity, pelvic pain, post operative pain, post stroke pain, menstrual pain, smoking cessation, ischemia, sepsis, wound healing, and other complications associated with diabetes, among other systemic and neuroimmunomodulatory activities, described above, alone or in combination with at least one pharmaceutically acceptable carrier.

In various embodiments, the present invention provides at least one variable that occurs more than one time in any substituent or in the compound of the present invention or any other formulae herein. Definition of a variable on each occurrence is independent of its definition at another occurrence. Further, combinations of substituents are permissible only if such combinations result in stable compounds. Stable compounds are compounds, which can be isolated from a reaction mixture.

Although typically it may be recognized that an asterisk is used to indicate that the exact subunit composition of a receptor is uncertain, for example α3b4* indicates a receptor that contains the α3 and β4 proteins in combination with other subunits, the term α7 as used herein is intended to include receptors wherein the exact subunit composition is both certain and uncertain. For example, as used herein α7 includes homomeric (α7)$_5$ receptors and α7* receptors, which denote a nAChR containing at least one α7 subunit.

a. Definitions

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of from 2 to 10 carbon atoms containing at least one double bond. Representative examples of alkenylene include, but are not limited to, —CH═CH—, —CH═CH$_2$CH$_2$—, and —CH═C(CH$_3$)CH$_2$—.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched, saturated hydrocarbon chain containing from 1 to 10 carbon atoms. The term "lower alkyl" or "C$_{1-6}$ alkyl" means a straight or branched chain hydrocarbon containing 1 to 6 carbon atoms. The term "C$_{1-3}$ alkyl" means a straight or branched chain hydrocarbon containing 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" means a divalent group derived from a straight or branched chain hydrocarbon of from 1 to 10 carbon atoms. Representative examples of alkylene include, but are not limited to, —CH$_2$—, —CH(CH$_3$)—, —C(CH$_3$)$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Representative examples of the aryl groups include, but are not limited to, dihydroindenyl, indenyl, naphthyl, dihydronaphthalenyl, and tetrahydronaphthalenyl. The bicyclic aryl is attached to the parent molecular moiety through any carbon atom contained within the bicyclic ring system. The aryl groups of the present invention can be unsubstituted or substituted.

The term "arylalkyl" as used herein, means an aryl group, as defined herein, appended to the parent molecular moiety through an alkylene group, as defined herein. Representative examples of arylalkyl include, but are not limited to, benzyl, 2-phenylethyl, 3-phenylpropyl, and 2-naphth-2-ylethyl.

The term "cyano" as used herein, means a —CN group.

The term "cyanoalkyl" as used herein, means a cyano group, as defined herein, appended to the parent molecular moiety through an alkylene group, as defined herein. Representative examples of cyanoalkyl include, but are not limited to, cyanomethyl, 2-cyanoethyl, and 3-cyanopropyl.

The term "cycloalkenyl" as used herein, means a monocyclic or bicyclic ring system containing from 3 to 10 carbons and containing at least one carbon-carbon double bond. Representative examples of monocyclic ring systems include, but are not limited to, 2-cyclohexen-1-yl, 3-cyclohexen-1-yl, 2,4-cyclohexadien-1-yl and 3-cyclopenten-1-yl. Bicyclic ring systems are exemplified by a monocyclic cycloalkenyl ring system which is fused to another monocyclic cycloalkyl ring as defined herein, a monocyclic aryl ring as defined herein, a monocyclic heterocycle as defined herein or a monocyclic heteroaryl as defined herein. The bicyclic ring systems of the present invention must be appended to the parent molecular moiety through an available carbon atom within the cycloalkenyl ring. Representative examples of bicyclic ring systems include, but are not limited to, 4,5-dihydro-benzo[1,2,5]oxadiazole, 3a,4,5,6,7,7a-hexahydro-1H-indenyl, 1,2,3,4,5,6-hexahydro-pentalenyl, 1,2,3,4,4a,5,6,8a-octahydro-pentalenyl.

The term "cycloalkyl" or "cycloalkane" as used herein, means a monocyclic, a bicyclic, or a tricyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring, or a bridged monocyclic ring system in which two non-adjacent carbon atoms of the monocyclic ring are linked by an alkylene bridge containing one, two, three, or four carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]

nonane, and bicyclo[4.2.1]nonane. Tricyclic cycloalkyls are exemplified by a bicyclic cycloalkyl fused to a monocyclic cycloalkyl, or a bicyclic cycloalkyl in which two non-adjacent carbon atoms of the ring systems are linked by an alkylene bridge of 1, 2, 3, or 4 carbon atoms. Representative examples of tricyclic-ring systems include, but are not limited to, tricyclo[3.3.1.0$^{3,7}$]nonane (octahydro-2,5-methanopentalene or noradamantane), and tricyclo[3.3.1.1$^{3,7}$]decane (adamantane). The monocyclic, bicyclic, and tricyclic cycloalkyls can be unsubstituted or substituted, and are attached to the parent molecular moiety through any substitutable atom contained within the ring system.

The term "halo" or "halogen" as used herein, means Cl, Br, I, or F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" as used herein, means an alkyl group, as defined herein, in which one, two, three, four, five or six hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, and trifluoropropyl such as 3,3,3-trifluoropropyl.

The term "heteroaryl" as used herein, means a monocyclic heteroaryl or a bicyclic heteroaryl or a tricyclic heteroaryl. The monocyclic heteroaryl is a five- or six-membered ring. The five-membered ring contains two double bonds. The five-membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo[1,2-c]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, thieno[2,3-c]pyridin-5-yl, thieno[3,2-b]pyridin-5-yl, and 5,6,7,8-tetrahydroquinolin-5-yl. The tricyclic heteroaryl consists of a bicyclic heteroaryl fused to a phenyl, or a bicyclic heteroaryl fused to a monocyclic cycloalkyl, or a bicyclic heteroaryl fused to a monocyclic cycloalkenyl, or a bicyclic heteroaryl fused to a monocyclic heteroaryl, or a bicyclic heteroaryl fused to a monocyclic heterocycle. Representative examples of tricyclic heteroaryl groups include, but are not limited to, dibenzo[b,d]thiophenyl, 9H-carbazolyl, and phenanthridine. The ring nitrogen and sulfur atoms of the monocyclic, bicyclic and tricyclic heteroaryl groups of the present invention can be oxidized. Representative examples of oxidized monocyclic, bicyclic and tricylic heteroaryl groups include, but are not limited to, pyridine 1-oxide, isoquinoline 2-oxide, and dibenzo[b,d]thiophene 5,5-dioxide, respectively. The monocyclic, bicyclic and tricyclic heteroaryl groups of the present invention can be substituted or unsubstituted and are connected to the parent molecular moiety through any carbon atom or any nitrogen atom contained within the ring systems.

The term "heteroarylalkyl," as used herein, means a heteroaryl group appended to the parent molecular moiety through an alkyl group, as defined herein.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but not limited to, octahydro-2,5-epoxypentalene, hexahydro-2H-2,5-methanocyclopenta[b]furan, hexahydro-1H-1,4-methanocyclopenta[c]furan, aza-admantane (1-azatricyclo[3.3.1.1$^{3,7}$]decane), and oxa-adamantane (2-oxatricyclo[3.3.1.1$^{3,7}$]decane), 1,4-diazatricyclo[4.3.1.1$^{3,8}$]undecane, 1,4-diazatricyclo[4.3.1.1$^{3,8}$]undecan-5-one. The monocyclic, bicyclic, and tricyclic heterocycles are connected to the parent molecular moiety through any carbon atom or any nitrogen atom contained within the rings, and can be unsubstituted or substituted.

The term "heteroatom" as used herein, means a nitrogen, oxygen, or sulfur atom.

The term "nitro" as used herein, means a —$NO_2$ group.

The term "oxo" as used herein, means a =O group.

The term "pain", as used herein, is understood to mean nociceptive pain and neuropathic pain, both chronic and acute pain, including but not limited to, osteoarthritis or rheumatoid arthritis pain, ocular pain, pains associated with intestinal inflammation, pains associated with cardiac muscle inflammation, pains associated with multiple sclerosis, pains associated with neuritis, pains associated with carcinomas and sarcomas, pains associated with AIDS, pains associated with chemotherapy, amputation pain, trigeminus neuralgia, headaches, such as migraine cephalalgia, or neuropathic pains, such as post-herpes zoster neuralgia, post-injury pains and post-operative pains.

The term "pharmaceutically acceptable salts, esters and amides" as used herein, include salts, zwitterions, esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base functional group with a suitable organic acid.

Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, malate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate, and undecanoate.

The term "pharmaceutically acceptable prodrug" or "prodrug," as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use.

b. Compounds

Compounds of the present invention have the formula (I) as described above.

Particular values of variable groups in compounds of formula (I) are as follows. Such values may be used where appropriate with any of the other values, definitions, claims or embodiments defined hereinbefore or hereinafter.

In one embodiment, X is C=O and R is hydrogen.
In another embodiment, X is $CH_2$ and R is hydrogen.
In one embodiment, X is C=O, and R is $Ar^1$.
In one embodiment, X is $CH_2$ and R is $Ar^1$.

In another embodiment, X is $CH_2$ and R is $Ar^1$, wherein $Ar^1$ is 5,5-dioxidodibenzo[b,d]thien-3-yl, phenyl, pyridyl, thiazolyl, pyridazinyl, pyrimidinyl, indolyl, thienyl, furanyl, pyrazolyl, benzofuranyl, indazolyl, benzothiophenyl, benzooxazolyl, benzothiazolyl, oxazolopyridinyl, or thiazolopyridinyl optionally substituted with 0, 1, 2, or 3 alkyl, halo, cyano, alkoxy, haloalkyl, nitro, or morpholino.

In a further embodiment, X is $CH_2$ and R is $Ar^1$, wherein $Ar^1$ is 5,5-dioxidodibenzo[b,d]thien-3-yl, benzooxazolyl, or benzothiazolyl, optionally unsubstituted or substituted with 1, 2, or 3 alkyl, halo, cyano, alkoxy, or haloalkyl.

In one embodiment, X is C=O, and R is $Ar^2$—$Ar^3$.
In one embodiment, X is $CH_2$ and R is $Ar^2$—$Ar^3$.

In another embodiment, X is $CH_2$, and R is $Ar^2$—$Ar^3$, wherein $Ar^3$ is 1,3,4-oxadiazolyl, pyrazolyl, pyridazinyl, pyridyl, phenyl, thiazolyl, or 1,3,4-thiadiazolyl; and $Ar^3$ is phenyl, benzothienyl, isoxazolyl, pyridyl, pyrimidinyl, indolyl, thiophenyl or thienyl, furanyl, pyrazolyl, benzofuranyl, or indazolyl, wherein $Ar^3$ and $Ar^3$ are each independently optionally substituted with 0, 1, 2, or 3 alkyl, halo, cyano, alkoxy, haloalkyl, haloalkoxy, nitro, —$OR^{1a}$, —O—$(CR^{4a}R^{5a})_p$—O—, —$C(O)R^{1a}$, —$N(R^b)(R^{3a})$ or —$N(R^a)C(O)R^{1a}$, wherein $R^{1a}$ and $R^{3a}$, $R^{3a}$, at each occurrence, are each independently alkyl or haloalkyl; $R^{4a}$ and $R^{5a}$, at each occurrence, are each independently hydrogen or alkyl; and $R^b$, at each occurrence, are each independently hydrogen, alkyl, or haloalkyl.

In a further embodiment, X is $CH_2$, and R is $Ar^2$—$Ar^3$, wherein $Ar^3$ is 1,3,4-oxadiazolyl, pyrazolyl, pyridazinyl, pyridyl, thiadiazolyl, or thiazolyl; and $Ar^3$ is phenyl, benzothienyl, isoxazolyl, pyridyl, pyrimidinyl, thiophenyl furanyl, or indolyl, wherein $Ar^3$ is unsubstituted and $Ar^3$ is unsubstituted or substituted with 1, 2, or 3 alkyl, halogen, cyano, —$OR^{1a}$, —O—$(CR^{4a}R^{5a})_p$—O—, —$C(O)R^{1a}$, —$N(R^b)(R^{3a})$, —$N(R^a)C(O)R^{1a}$, or haloalkyl; wherein $R^{1a}$ and $R^{3a}$, at each occurrence, are each independently alkyl or haloalkyl; $R^{4a}$ and $R^{5a}$, at each occurrence, are each independently hydrogen or alkyl; and $R^b$, at each occurrence, are each independently hydrogen, alkyl, or haloalkyl.

In one embodiment, X is C=O, and R is —C(O)—$Ar^2$—$Ar^3$.

In one embodiment, X is $CH_2$ and R is —C(O)—$Ar^2$—$Ar^3$.

In another embodiment, X is $CH_2$, and R is —C(O)—$Ar^2$—$Ar^3$, wherein $Ar^3$ is 1,3,4-oxadiazolyl, pyrazolyl, pyridazinyl, pyridyl, phenyl, thiazolyl, or 1,3,4-thiadiazolyl; and $Ar^3$ is phenyl, benzothienyl, isoxazolyl, pyridyl, pyrimidinyl, indolyl, thiophenyl or thienyl, furanyl, pyrazolyl, benzofuranyl, or indazolyl, wherein $Ar^3$ and $Ar^3$ are each independently optionally substituted with 0, 1, 2, or 3 alkyl, halo, cyano, alkoxy, haloalkyl, haloalkoxy, nitro —$OR^{1a}$, —O—$(CR^{4a}R^{5a})_p$—O—, —$C(O)R^{1a}$, —$N(R^b)(R^{3a})$, or —$N(R^a)C(O)R^{1a}$, wherein $R^{1a}$ and $R^{3a}$, at each occurrence, are each independently alkyl or haloalkyl; $R^{4a}$ and $R^{5a}$, at each occurrence, are each independently hydrogen or alkyl; and $R^b$, at each occurrence, are each independently hydrogen, alkyl, or haloalkyl.

In a further embodiment, X is $CH_2$, and R is —C(O)—$Ar^2$—$Ar^3$, wherein $Ar^3$ is pyrazolyl or thiadiazolyl; and $Ar^3$ is phenyl, wherein $Ar^3$ is unsubstituted and $Ar^3$ is unsubstituted or substituted with 1, 2, or 3 alkyl, halogen, cyano, —$OR^{1a}$, —O—$(CR^{4a}R^{5a})_p$—O—, —$C(O)R^{1a}$—$N(R^b)(R^{3a})$, —$N(R^a)C(O)R^{1a}$, or haloalkyl; wherein $R^{1a}$ and $R^{3a}$, at each occurrence, are each independently alkyl or haloalkyl; $R^{4a}$ and $R^{5a}$, at each occurrence, are each independently hydrogen or alkyl; and $R^b$, at each occurrence, are each independently hydrogen, alkyl, or haloalkyl.

In one embodiment, X is C=O, and R is —(CH$_2$)$_q$Ar$^3$.

In one embodiment, X is CH$_2$, and R is —(CH$_2$)$_q$Ar$^3$.

In another embodiment, X is CH$_2$, and R is —(CH$_2$)$_q$Ar$^3$, wherein q is 1, 2, 3, 4 or 5, and wherein Ar$^3$ is phenyl, pyridyl, thiazolyl, pyridazinyl, pyrimidinyl, indolyl, thienyl, furanyl, pyrazolyl, benzofuranyl, indazolyl, benzothiophenyl, benzooxazolyl, benzothiazolyl, oxazolopyridinyl, or thiazolopyridinyl optionally substituted with 0, 1, 2, or 3 alkyl, halo, cyano, alkoxy, haloalkyl, or nitro.

In one embodiment, X is C=O, and R is —C(O)Ar$^3$.

In another embodiment, X is CH$_2$, and R is —C(O)Ar$^3$, wherein Ar$^3$ is phenyl, pyridyl, thiazolyl, pyrazinyl, pyridazinyl, pyrimidinyl, indolyl, thienyl, furanyl, pyrazolyl, pyrrolyl, benzofuranyl, indazolyl, benzothienyl, benzooxazolyl, benzothiazolyl, indazolyl, oxazolopyridinyl, thiazolopyridinyl, thieno[3,2-b]pyridin-5-yl or quinolinyl optionally substituted with 0, 1, 2, or 3 alkyl, halogen, cyano, —OR$^{1a}$, —N(R$^b$)(R$^{3a}$), —N(R$^a$)C(O)R$^{1a}$, or haloalkyl; wherein R$^{1a}$ and R$^{3a}$, at each occurrence, are each independently alkyl or haloalkyl; and R$^b$ is hydrogen, alkyl, or haloalkyl.

In a further embodiment, X is CH$_2$, and R is —C(O)Ar$^3$, wherein Ar$^3$ is phenyl or heteroaryl, wherein heteroaryl is selected from pyridinyl, furanyl, indolyl, thienyl, pyrazinyl, quinolinyl, pyrrolyl, benzofuranyl, benzothienyl, thieno[3,2-b]pyridin-5-yl or indazolyl, and wherein the phenyl or heteroaryl is unsubstituted or substituted with 1, 2, 3, or 4 substituents selected from alkyl, halogen, cyano, —OR$^{1a}$, —N(R$^b$)(R$^{3a}$), —N(R$^a$)C(O)R$^{1a}$, or haloalkyl; wherein R$^{1a}$ and R$^{3a}$, at each occurrence, are each independently alkyl or haloalkyl; and R$^b$ is hydrogen, alkyl, or haloalkyl.

In one embodiment, X is C=O, and R is —C(O)OAr$^3$.

In one embodiment, X is CH$_2$, and R is —C(O)OAr$^3$, wherein Ar$^3$ is phenyl, pyridyl, thiazolyl, pyrazinyl, pyridazinyl, pyrimidinyl, indolyl, thienyl, furanyl, pyrazolyl, pyrrolyl, benzofuranyl, indazolyl, benzothienyl, benzooxazolyl, benzothiazolyl, indazolyl, oxazolopyridinyl, thiazolopyridinyl, thieno[3,2-b]pyridin-5-yl or quinolinyl optionally substituted with 0, 1, 2, or 3 alkyl, halogen, cyano, —OR$^{1a}$, —N(R$^b$)(R$^{3a}$), —N(R$^a$)C(O)R$^{1a}$, or haloalkyl; wherein R$^{1a}$ and R$^{3a}$, at each occurrence, are each independently alkyl or haloalkyl; and R$^b$ is hydrogen, alkyl, or haloalkyl.

In a further embodiment, X is CH$_2$, and R is —C(O)OAr$^3$, wherein Ar$^3$ is phenyl or heteroaryl, wherein heteroaryl is selected from pyridinyl, furanyl, indolyl, thienyl, pyrazinyl, quinolinyl, benzofuranyl, benzothienyl, pyrrolyl, thieno[3,2-b]pyridin-5-yl or indazolyl, wherein the phenyl or heteroaryl is unsubstituted or substituted with 1, 2, 3, or 4 substituents selected from alkyl, halogen, cyano, —OR$^{1a}$, —N(R$^b$)(R$^{3a}$), —N(R$^a$)C(O)R$^{1a}$, or haloalkyl; wherein R$^{1a}$ and R$^{3a}$, at each occurrence, are each independently alkyl or haloalkyl; and R$^b$ is hydrogen, alkyl, or haloalkyl.

In one embodiment, X is C=O, and R is —C(O)NR$^1$R$^2$.

In one embodiment, X is CH$_2$, and R is —C(O)NR$^1$R$^2$.

In another embodiment, X is CH$_2$, and R is —C(O)NR$^1$R$^2$, wherein R$^1$ is hydrogen or alkyl; and R$^2$ is aryl, arylalkyl, heteroaryl, or heteroarylalkyl, wherein each aryl or heteroaryl or the aryl and heteroaryl moieties on arylalkyl and heteroarylalkyl groups are independently unsubstituted or substituted with 1, 2, 3, 4, or 5 substituents selected from the group consisting of alkyl, alkenyl, alkynyl, arylalkyl, halogen, cyano, -G$^1$, —NO$_2$, —OR$^{1a}$, —O—(CR$^{4a}$R$^{5a}$)$_p$—O—, —OC(O)R$^{1a}$, —OC(O)N(R$^b$)(R$^{3a}$), —SR$^{1a}$, —S(O)$_2$R$^{2a}$, —S(O)$_2$N(R$^b$)(R$^{3a}$), —C(O)R$^{1a}$, —C(O)OR$^{1a}$, —C(O)N(R$^b$)(R$^{3a}$), —N(R$^b$)(R$^{3a}$), —N(R$^a$)C(O)R$^{1a}$, —N(R$^a$)C(O)O(R$^{1a}$), —N(R$^a$)C(O)N(R$^b$)(R$^{3a}$), —(CR$^{4a}$R$^{5a}$)$_m$—NO$_2$, —(CR$^{4a}$R$^{5a}$)$_m$—OR$^{1a}$, —(CR$^{4a}$R$^{5a}$)$_m$—OC(O)R$^{1a}$, —(CR$^{4a}$R$^{5a}$)OC(O)N(R$^b$)(R$^{3a}$), —(CR$^{4a}$R$^{5a}$)$_m$—SR$^{1a}$, —(CR$^{4a}$R$^{5a}$)S(O)$_2$R$^{2a}$, —(CR$^{4a}$R$^{5a}$)$_m$—S(O)$_2$N(R$^b$)(R$^{3a}$), —(CR$^{4a}$R$^{5a}$)$_m$—C(O)R$^{1a}$, —(CR$^{4a}$R$^{5a}$)$_m$—C(O)OR$^{1a}$, —(CR$^{4a}$R$^{5a}$)$_m$—C(O)N(R$^b$)(R$^{3a}$), —(CR$^{4a}$R$^{5a}$)$_m$—N(R$^b$)(R$^{3a}$)—(CR$^{4a}$R$^{5a}$)$_m$—N(R$^a$)C(O)R$^{1a}$, —(CR$^{4a}$R$^{5a}$)$_m$—N(R$^a$)C(O)O(R$^{1a}$), —(CR$^{4a}$R$^{5a}$)$_m$—N(R$^a$)C(O)N(R$^b$)(R$^{3a}$), —(CR$^{4a}$R$^{5a}$)$_m$—G$^2$, cyanoalkyl, and haloalkyl; wherein R$^{1a}$ and R$^{3a}$ at each occurrence, are each independently hydrogen, alkyl, haloalkyl, G$^2$, or —(CR$^{6a}$R$^{7a}$)$_n$-G$^2$; R$^{2a}$ at each occurrence, is independently alkyl, haloalkyl, G$^2$, or —(CR$^{6a}$R$^{7a}$)$_n$- G$^2$; R$^{4a}$, R$^{5a}$, R$^{6a}$, and R$^{7a}$, at each occurrence, are each independently hydrogen, halogen, alkyl, or haloalkyl; R$^a$ and R$^b$, at each occurrence, are each independently hydrogen, alkyl, or haloalkyl; m and n, at each occurrence, are each independently 1, 2, 3, 4, or 5; p, at each occurrence, is 1 or 2; —O—(CR$^{4a}$R$^{5a}$)$_p$—O— is a divalent substituent attached to two adjacent carbon atoms of the aryl or heteroaryl; G$^1$, at each occurrence, is heterocycle or cycloalkyl, wherein each G$^1$ is independently unsubstituted or substituted with 1, 2, 3, 4, or 5 substituents selected from the group consisting of alkyl, alkenyl, alkynyl, halogen, cyano, oxo, —NO$_2$, —OR$^{1b}$, —OC(O)R$^{1b}$, —OC(O)N(R$^b$)(R$^{3b}$), —SR$^{1b}$, —S(O)$_2$R$^{2b}$, —S(O)$_2$N(R$^b$)(R$^{3b}$), —C(O)R$^{1b}$, —C(O)OR$^{1b}$, —C(O)N(R$^b$)(R$^{3b}$), —N(R$^b$)(R$^{3b}$), —N(R$^a$)C(O)R$^{1b}$, —N(R$^a$)C(O)O(R$^{1b}$), —N(R$^a$)C(O)N(R$^b$)(R$^{3b}$), —(CR$^{4b}$R$^{5b}$)$_m$—NO$_2$, —(CR$^{4b}$R$^{5b}$)$_m$—OR$^{1b}$, —(CR$^{4b}$R$^{5b}$)$_m$—OC(O)R$^{1b}$, —(CR$^{4b}$R$^{5b}$)OC(O)N(R$^b$)(R$^{3b}$), —(CR$^{4b}$R$^{5b}$)$_m$—SR$^{1b}$, —(CR$^{4b}$R$^{5b}$)$_m$—S(O)$_2$R$^{2b}$, —(CR$^{4b}$R$^{5b}$)$_m$—S(O)$_2$N(R$^b$)(R$^{3b}$), —(CR$^{4b}$R$^{5b}$)$_m$—C(O)R$^{1b}$, —(CR$^{4b}$R$^{5b}$)$_m$—C(O)OR$^{1b}$, —(CR$^{4b}$R$^{5b}$)$_m$—C(O)N(R$^b$)(R$^{3b}$), —(CR$^{4b}$R$^{5b}$)$_m$—N(R$^b$)(R$^{3b}$), —(CR$^{4b}$R$^{5b}$)$_m$—N(R$^a$)C(O)R$^{1b}$, —(CR$^{4b}$R$^{5b}$)N(R$^a$)C(O)O(R$^{1b}$), —(CR$^{4b}$R$^{5b}$)$_m$—N(R$^a$)C(O)N(R$^b$)(R$^{3b}$), cyanoalkyl, and haloalkyl; R$^{1b}$ and R$^{3b}$, at each occurrence, are each independently hydrogen, alkyl, or haloalkyl; R$^{2b}$, at each occurrence, is independently alkyl or haloalkyl; R$^{4b}$ and R$^{5b}$, at each occurrence, are each independently hydrogen, halogen, alkyl, or haloalkyl; and G$^2$, at each occurrence, is aryl, heteroaryl, heterocycle, or cycloalkyl, wherein each G$^2$ is independently unsubstituted or substituted with 1, 2, 3, 4, or 5 substituents selected from the group consisting of alkyl, alkenyl, alkynyl, halogen, cyano, oxo, —NO$_2$, —OR$^{1b}$, —OC(O)R$^{1b}$, —OC(O)N(R$^b$)(R$^{3b}$), —SR$^{1b}$, —S(O)$_2$R$^{2b}$, —S(O)$_2$N(R$^b$)(R$^{3b}$), —C(O)R$^{1b}$, —C(O)OR$^{1b}$, —C(O)N(R$^b$)(R$^{3b}$), —N(R$^b$)(R$^{3b}$), —N(R$^a$)C(O)R$^{1b}$, —N(R$^a$)C(O)O(R$^{1b}$), —N(R$^a$)C(O)N(R$^b$)(R$^{3b}$), —(CR$^{4b}$R$^{5b}$)$_m$—NO$_2$, —(CR$^{4b}$R$^{5b}$)$_m$—OR$^{1b}$, —(CR$^{4b}$R$^{5b}$)$_m$—OC(O)R$^{1b}$, —(CR$^{4b}$R$^{5b}$)$_m$—OC(O)N(R$^b$)(R$^{3b}$), —(CR$^{4b}$R$^{5b}$)$_m$—SR$^{1b}$, —(CR$^{4b}$R$^{5b}$)$_m$—S(O)$_2$R$^{2b}$, —(CR$^{4b}$R$^{5b}$)$_m$—S(O)$_2$N(R$^b$)(R$^{3b}$), —(CR$^{4b}$R$^{5b}$)$_m$—C(O)R$^{1b}$, —(CR$^{4b}$R$^{5b}$)$_m$—C(O)OR$^{1b}$, —(CR$^{4b}$R$^{5b}$)$_m$—C(O)N(R$^b$)(R$^{3b}$), —(CR$^{4b}$R$^{5b}$)$_m$—N(R$^b$)(R$^{3b}$), —(CR$^{4b}$R$^{5b}$)$_m$—N(R$^a$)C(O)R$^{1b}$, —(CR$^{4b}$R$^{5b}$)$_m$—N(R$^a$)C(O)O(R$^{1b}$), —(CR$^{4b}$R$^{5b}$)$_m$—N(R$^a$)C(O)N(R$^b$)(R$^{3b}$), cyanoalkyl, and haloalkyl.

In a further embodiment, X is CH$_2$, and R is —C(O)NR$^1$R$^2$, wherein R$^1$ is hydrogen or alkyl; and R$^2$ is aryl, arylalkyl, heteroaryl, or heteroarylalkyl, wherein each aryl or heteroaryl or the aryl and heteroaryl moieties on arylalkyl and heteroarylalkyl groups are independently unsubstituted or substituted with 1, 2, or 3 substituents selected from the group consisting of alkyl, halogen, cyano, —OR$^{1a}$, —C(O)R$^{1a}$, —N(R$^b$)(R$^{3a}$), —N(R$^a$)C(O)R$^{1a}$; wherein R$^{1a}$ and R$^{3a}$, at each occurrence, are each independently hydrogen, alkyl, or haloalkyl; and R$^b$ is hydrogen or alkyl.

In one embodiment, X is C=O, and R is —C(O)—(CR$^x$R$^y$)$_q$—Ar$^3$ or —C(O)—(CR$^x$R$^y$)$_q$—O—Ar$^3$.

In one embodiment, X is CH$_2$, and R is —C(O)—(CR$^x$R$^y$)$_q$—Ar$^3$ or —C(O)—(CR$^x$R$^y$)$_q$—O—Ar$^3$.

In another embodiment, X is CH$_2$, and R is —C(O)—(CR$^x$R$^y$)$_q$—Ar$^3$ or —C(O)—(CR$^x$R$^y$)$_q$—O—Ar$^3$, wherein R$^x$ and R$^y$, at each occurrence, are each independently hydrogen, alkyl or haloalkyl; q is 1, 2 or 3; Ar$^a$ is aryl or heteroaryl; wherein each aryl or heteroaryl are independently unsubstituted or substituted with 1, 2, 3, 4, or 5 substituents selected from the group consisting of alkyl, alkenyl, alkynyl, arylalkyl, halogen, cyano, -G$^1$, —NO$_2$, —OR$^{1a}$, —O—(CR$^{4a}$R$^{5a}$)$_p$—O—, —OC(O)R$^{1a}$, —OC(O)N(R$^b$)(R$^{3a}$), —SR$^{1a}$, —S(O)$_2$R$^{2a}$, —S(O)$_2$N(R$^b$)(R$^{3a}$), —C(O)R$^{1a}$, —C(C)OR$^{1a}$, —C(O)N(R$^b$)(R$^{3a}$), —N(R$^b$)(R$^{3a}$), —N(R$^a$)C(O)R$^{1a}$, —N(R$^a$)C(O)O(R$^{1a}$), —N(R$^a$)C(O)N(R$^b$)(R$^{3a}$), —(CR$^{4a}$R$^{5a}$)$_m$—NO$_2$, —(CR$^{4a}$R$^{5a}$)$_m$—OR$^{1a}$, —(CR$^{4a}$R$^{5a}$)$_m$—OC(O)R$^{1a}$, —(CR$^{4a}$R$^{5a}$)$_m$—OC(O)N(R$^b$)(R$^{3a}$), —(CR$^{4a}$R$^{5a}$)$_m$—SR$^{1a}$, —(CR$^{4a}$R$^{5a}$)$_m$—S(O)$_2$R$^{2a}$, —(CR$^{4a}$R$^{5a}$)S(O)$_2$N(R$^b$)(R$^{3a}$)—(CR$^{4a}$R$^{5a}$)$_m$—C(O)R$^{1a}$, —(CR$^{4a}$R$^{5a}$)$_m$—C(O)OR$^{1a}$, —(CR$^{4a}$R$^{5a}$)$_m$—C(O)N(R$^b$)(R$^{3a}$), —(CR$^{4a}$R$^{5a}$)$_m$—N(R$^b$)(R$^{3a}$), —(CR$^{4a}$R$^{5a}$)$_m$—N(R$^a$)C(O)R$^{1a}$, —(CR$^{4a}$R$^{5a}$)$_m$—N(R$^a$)C(O)O(R$^{1a}$), —(CR$^{4a}$R$^{5a}$)$_m$—N(R$^a$)C(O)N(R$^b$)(R$^{3a}$), —(CR$^{4a}$R$^{5a}$)$_m$-G$^2$, cyanoalkyl, and haloalkyl; wherein R$^{1a}$ and R$^{3a}$, at each occurrence, are each independently hydrogen, alkyl, haloalkyl, G$^2$, or —(CR$^{6a}$R$^{7a}$)$_n$-G$^2$; R$^{2a}$, at each occurrence, is independently alkyl, haloalkyl, G$^2$, or —(CR$^{6a}$R$^{7a}$)$_n$-G$^2$; R$^{4a}$, R$^{5a}$, R$^{6a}$, and R$^{7a}$, at each occurrence are each independently hydrogen, halogen, alkyl, or haloalkyl; R$^a$ and R$^b$, at each occurrence, are each independently hydrogen, alkyl, or haloalkyl; m and n, at each occurrence, are each independently 1, 2, 3, 4, or 5; p, at each occurrence, is 1 or 2; —O—(CR$^{4a}$R$^{5a}$)$_p$—O— is a divalent substituent attached to two adjacent carbon atoms of the aryl or heteroaryl; G$^1$, at each occurrence, is heterocycle or cycloalkyl, wherein each G$^1$ is independently unsubstituted or substituted with 1, 2, 3, 4, or 5 substituents selected from the group consisting of alkyl, alkenyl, alkynyl, halogen, cyano, oxo, —NO$_2$, —OR$^{1b}$, —OC(O)R$^{1b}$, —OC(O)N(R$^b$)(R$^{3b}$), —SR$^{1b}$, —S(O)$_2$R$^{2b}$, —S(O)$_2$N(R$^b$)(R$^{3b}$), —C(O)R$^{1b}$—C(O)OR$^{1b}$, —C(O)N(R$^b$)(R$^{3b}$), —N(R$^b$)(R$^{3b}$), —N(R$^a$)C(O)R$^{1b}$, —N(R$^a$)C(O)O(R$^{1b}$), —N(R$^a$)C(O)N(R$^b$)(R$^{3b}$), —(CR$^{4b}$R$^{5b}$)$_m$—NO$_2$, —(CR$^{4b}$R$^{5b}$)$_m$—OR$^{1b}$, —(CR$^{4b}$R$^{5b}$)$_m$—OC(O)R$^{1b}$, —(CR$^{4b}$R$^{5b}$)$_m$—OC(O)N(R$^b$)(R$^{3b}$), —(CR$^{4b}$R$^{5b}$)$_m$—SR$^{1b}$, —(CR$^{4b}$R$^{5b}$)$_m$—S(O)$_2$R$^{2b}$, —(CR$^{4b}$R$^{5b}$)$_m$—S(O)$_2$N(R$^b$)(R$^{3b}$), —(CR$^{4b}$R$^{5b}$)$_m$—C(O)R$^{1b}$, —(CR$^{4b}$R$^{5b}$)$_m$—C(O)OR$^{1b}$, —(CR$^{4b}$R$^{5b}$)$_m$—C(O)N(R$^b$)(R$^{3b}$), —(CR$^{4b}$R$^{5b}$)$_m$—N(R$^b$)(R$^{3b}$), —(CR$^{4b}$R$^{5b}$)$_m$—N(R$^a$)C(O)R$^{1b}$, —(CR$^{4b}$R$^{5b}$)$_m$—N(R$^a$)C(O)O(R$^{1b}$), —(CR$^{4b}$R$^{5b}$)$_m$—N(R$^a$)C(O)N(R$^b$)(R$^{3b}$), cyanoalkyl, and haloalkyl; R$^{1b}$ and R$^{3b}$, at each occurrence, are each independently hydrogen, alkyl, or haloalkyl; R$^{2b}$, at each occurrence, is independently alkyl or haloalkyl; R$^{4b}$ and R$^{5b}$, at each occurrence, are each independently hydrogen, halogen, alkyl, or haloalkyl; and G$^2$, at each occurrence, is aryl, heteroaryl, heterocycle, or cycloalkyl, wherein each G$^2$ is independently unsubstituted or substituted with 1, 2, 3, 4, or 5 substituents selected from the group consisting of alkyl, alkenyl, alkynyl, halogen, cyano, oxo, —NO$_2$, —OR$^{1b}$, —OC(O)R$^{1b}$, —OC(O)N(R$^b$)(R$^{3b}$), —SR$^{1b}$, —S(O)$_2$R$^{2b}$, —S(O)$_2$N(R$^b$)(R$^{3b}$), —C(O)R$^{1b}$, —C(O)OR$^{1b}$, —C(O)N(R$^b$)(R$^{3b}$), —N(R$^b$)(R$^{3b}$), —N(R$^a$)C(O)R$^{1b}$, —N(R$^a$)C(O)O(R$^{1b}$), —N(R$^a$)C(O)N(R$^b$)(R$^{3b}$), —(CR$^{4b}$R$^{5b}$)$_m$—NO$_2$, —(CR$^{4b}$R$^{5b}$)$_m$—OR$^{1b}$, —(CR$^{4b}$R$^{5b}$)$_m$—OC(O)R$^{1b}$, —(CR$^{4b}$R$^{5b}$)$_m$—OC(O)N(R$^b$)(R$^{3b}$), —(CR$^{4b}$R$^{5b}$)$_m$—SR$^{1b}$, —(CR$^{4b}$R$^{5b}$)$_m$—S(O)$_2$R$^{2b}$, —(CR$^{4b}$R$^{5b}$)S(O)$_2$N(R$^b$)(R$^{3b}$), —(CR$^{4b}$R$^{5b}$)$_m$—C(O)R$^{1b}$, —(CR$^{4b}$R$^{5b}$)$_m$—C(O)OR$^{1b}$, —(CR$^{4b}$R$^{5b}$)C(O)N(R$^b$)(R$^{3b}$), —(CR$^{4b}$R$^{5b}$)$_m$—N(R$^b$)(R$^{3b}$), —(CR$^{4b}$R$^{5b}$)$_m$—N(R$^a$)C(O)R$^{1b}$, —(CR$^{4b}$R$^{5b}$)$_m$—N(R$^a$)C(O)O(R$^{1b}$), —(CR$^{4b}$R$^{5b}$)$_m$—N(R$^a$)C(O)N(R$^b$)(R$^{3b}$), cyanoalkyl, and haloalkyl.

In a further embodiment, X is CH$_2$, and R is —C(O)—(CR$^x$R$^y$)$_q$—Ar$^3$ or —C(O)—(CR$^x$R$^y$)$_q$—O—Ar$^3$, wherein R$^x$ and R$^y$, at each occurrence, are each independently hydrogen or alkyl; q is 1 or 2; Ar$^3$ is phenyl, naphthyl or thienyl; wherein the phenyl, naphthyl or thienyl is unsubstituted or substituted with 1, 2, 3, or 4 substituents selected from alkyl, halogen, cyano, —OR$^{1a}$—N(R$^b$)(R$^{3a}$), —N(R$^a$)C(O)R$^{1a}$, or haloalkyl; wherein R$^{1a}$ and R$^{3a}$, at each occurrence, are each independently alkyl or haloalkyl; and R$^b$ is hydrogen, alkyl, or haloalkyl.

In one embodiment, X is C═O, and R is (i).

In one embodiment, X is CH$_2$, and R is (i).

In another embodiment, X is CH$_2$, and R is (i), wherein R$^x$ and R$^y$, at each occurrence, are each independently hydrogen, alkyl or haloalkyl; r and s are independently 0, 1, 2, or 3, wherein the total of r and s is 2, 3 or 4; A is aryl or heteroaryl; wherein each aryl or heteroaryl are independently unsubstituted or substituted with 1, 2, 3, 4, or 5 substituents selected from the group consisting of alkyl, alkenyl, alkynyl, arylalkyl, halogen, cyano, -G$^1$, —NO$_2$, —OR$^{1a}$, —O—(CR$^{4a}$R$^{5a}$)$_p$—O—, —OC(O)R$^{1a}$, —OC(O)N(R$^b$)(R$^{3a}$), —SR$^{1a}$, —S(O)$_2$R$^{2a}$, —S(O)$_2$N(R$^b$)(R$^{3a}$), —C(O)R$^{1a}$, —C(O)OR$^{1a}$, —C(O)N(R$^b$)(R$^{3a}$), —N(R$^b$)(R$^{3a}$), —N(R$^a$)C(O)R$^{1a}$, —N(R$^a$)C(O)O(R$^{1a}$), —N(R$^a$)C(O)N(R$^b$)(R$^{3a}$), —(CR$^{4a}$R$^{5a}$)$_m$—NO$_2$ (CR$^{4a}$R$^{5a}$)$_m$—OR$^{1a}$, —(CR$^{4a}$R$^{5a}$)$_m$—OC(O)R$^{1a}$, —(CR$^{4a}$R$^{5a}$)$_m$—OC(O)N(R$^b$)(R$^{3a}$), —(CR$^{4a}$R$^{5a}$)$_m$—SR$^{1a}$, —(CR$^{4a}$R$^{5a}$)$_m$—S(O)$_2$R$^{2a}$, —(CR$^{4a}$R$^{5a}$)$_m$—S(O)$_2$N(R$^b$)(R$^{3a}$), —(CR$^{4a}$R$^{5a}$)$_m$—C(O)R$^{1a}$, —(CR$^{4a}$R$^{5a}$)$_m$—C(O)OR$^{1a}$, —(CR$^{4a}$R$^{5a}$)$_m$—C(O)N(R$^b$)(R$^{3a}$), —(CR$^{4a}$R$^{5a}$)$_m$—N(R$^b$)(R$^{3a}$), —(CR$^{4a}$R$^{5a}$)$_m$—N(R$^a$)C(O)R$^{1a}$, —(CR$^{4a}$R$^{5a}$)$_m$—N(R$^a$)C(O)O(R$^{1a}$), —(CR$^{4a}$R$^{5a}$)$_m$—N(R$^a$)C(O)N(R$^b$)(R$^{3a}$), —(CR$^{4a}$R$^{5a}$)$_m$-G$^2$, cyanoalkyl, and haloalkyl; wherein R$^{1a}$ and R$^{3a}$, at each occurrence, are each independently hydrogen, alkyl, haloalkyl, G$^2$, or —(CR$^{6a}$R$^{7a}$)$_n$-G$^2$; R$^{2a}$, at each occurrence, is independently alkyl, haloalkyl, G$^2$, or —(CR$^{6a}$R$^{7a}$)$_n$-G$^2$; R$^{4a}$,R$^{5a}$, R$^{6a}$, and R$^{7a}$, at each occurrence, are each independently hydrogen, halogen, alkyl, or haloalkyl; R$^a$ and R$^b$, at each occurrence, are each independently hydrogen, alkyl, or haloalkyl; m and n, at each occurrence, are each independently 1, 2, 3, 4, or 5; p, at each occurrence, is 1 or 2; —O—(CR$^{4a}$R$^{5a}$)$_p$—O— is divalent substituent attached to two adjacent carbon atoms of the aryl or heteroaryl; G$^1$, at each occurrence, is heterocycle or cycloalkyl, wherein each G$^1$ is independently unsubstituted or substituted with 1, 2, 3, 4, or 5 substituents selected from the group consisting of alkyl, alkenyl, alkynyl, halogen, cyano, oxo, —NO$_2$, —OC(O)R$^{1b}$, —OC(O)N(R$^b$)(R$^{3b}$), —SR$^{1b}$, —S(O)$_2$R$^{2b}$, —S(O)$_2$ N(R$^b$)(R$^{3b}$), —C(O)R$^{1b}$, —C(O)OR$^{1b}$, —C(O)N(R$^b$)(R$^{3b}$), —N(R$^b$)(R$^{3b}$), —N(R$^a$)C(O)R$^{1b}$, —N(R$^a$)C(O)O(R$^{1b}$), —N(R$^a$)C(O)N(R$^b$)(R$^{3b}$), —(CR$^{4b}$R$^{5b}$)NO$_2$, —(CR$^{4b}$R$^{5b}$)$_m$—OR$^{1b}$, —(CR$^{4b}$R$^{5b}$)$_m$—OC(O)R$^{1b}$, —(CR$^{4b}$R$^{5b}$)$_m$—OC(O)N(R$^b$)(R$^{3b}$), —(CR$^{4b}$R$^{5b}$)$_m$—SR$^{1b}$, —(CR$^{4b}$R$^{5b}$)$_m$—S(O)$_2$R$^{2b}$, —(CR$^{4b}$R$^{5b}$)$_m$—S(O)$_2$N(R$^b$)(R$^{3b}$), —(CR$^{4b}$R$^{5b}$)$_m$—C(O)R$^{1b}$, —(CR$^{4b}$R$^{5b}$)$_m$—C(O)OR$^{1b}$, —(CR$^{4b}$R$^{5b}$)$_m$—C(O)N(R$^b$)(R$^{3b}$), —(CR$^{4b}$R$^{5b}$)$_m$—N(R$^b$)(R$^{3b}$), —(CR$^{4b}$R$^{5b}$)$_m$—N(R$^a$)C(O)R$^{1b}$, —(CR$^{4b}$R$^{5b}$)$_m$—N(R$^a$)C(O)O(R$^{1b}$), —(CR$^{4b}$R$^{5b}$)$_m$—N(R$^a$)C(O)N(R$^b$)(R$^{3b}$), cyanoalkyl, and haloalkyl; R$^{1b}$ and R$^{3b}$, at each occurrence, are each independently hydrogen, alkyl, or haloalkyl; R$^{2b}$, at each occurrence, is independently alkyl or haloalkyl; R$^{4b}$ and R$^{5b}$, at each occurrence, are each independently hydrogen, halogen, alkyl, or haloalkyl; and G$^2$, at each occurrence, is aryl, heteroaryl, heterocycle, or cycloalkyl, wherein each G$^2$ is independently unsubstituted or substituted with 1, 2, 3, 4, or 5 substituents selected from the group consisting of alkyl, alkenyl, alkynyl, halogen, cyano, oxo, —NO$_2$, —OR$^{1b}$, —OC(O)R$^{1b}$, —OC (O)N(R$^b$)(R$^{3b}$), —SR$^{1b}$, —S(O)$_2$R$^{2b}$, —S(O)$_2$N(R$^b$)(R$^{3b}$), —C(O)R$^{1b}$, —C(O)OR$^{1b}$, —C(O)N(R$^b$)(R$^{3b}$), —N(R$^b$)(R$^{3b}$), —N(R$^a$)C(O)R$^{1b}$, —N(R$^a$)C(O)O(R$^{1b}$), —N(R$^a$)C(O)N(R$^b$)(R$^{3b}$), —(CR$^{4b}$R$^{5b}$)$_m$—NO$_2$, —(CR$^{4b}$R$^{5b}$)$_m$—OR$^{1b}$, —(CR$^{4b}$R$^{5b}$)$_m$—OC(O)R$^{1b}$, —(CR$^{4b}$R$^{5b}$)$_m$—OC(O)N(R$^b$)(R$^{3b}$), —(CR$^{4b}$R$^{5b}$)$_m$—SR$^{1b}$, —(CR$^{4b}$R$^{5b}$)$_m$—S(O)$_2$R$^{2b}$, —(CR$^{4b}$R$^{5b}$)$_m$—S(O)$_2$N(R$^b$)(R$^{3b}$), —(CR$^{4b}$R$^{5b}$)$_m$—C(O)R$^{1b}$, —(CR$^{4b}$R$^{5b}$)$_m$—C(O)OR$^{1b}$, —(CR$^{4b}$R$^{5b}$)$_m$—C(O)N(R$^b$)(R$^{3b}$), —(CR$^{4b}$R$^{5b}$)$_m$—N(R$^b$)(R$^{3b}$), —(CR$^{4b}$R$^{5b}$)$_m$—N(R$^a$)C(O)R$^{1b}$, —(CR$^{4b}$R$^{5b}$)$_m$—N(R$^a$)C(O)O(R$^{1b}$), —(CR$^{4b}$R$^{5b}$)$_m$—N(R$^a$)C(O)N(R$^b$)(R$^{3b}$), cyanoalkyl, and haloalkyl.

In a another embodiment, X is CH$_2$, and R (i), wherein R$^x$ and R$^y$, at each occurrence, are each independently hydrogen or alkyl; r and s are independently 0, 1, or 2, wherein the total of r and s is 2 or 3; A is phenyl, wherein the phenyl, is unsubstituted or substituted with 1, 2, 3, or 4 substituents selected from alkyl, halogen, cyano, —OR$^{1a}$, —N(R$^b$)(R$^{3a}$), —N(R$^a$)C(O)R$^{1a}$, or haloalkyl; wherein and R$^{1a}$ and R$^{3a}$, at each occurrence, are each independently alkyl or haloalkyl; and R$^b$ is hydrogen, alkyl, or haloalkyl.

In a another embodiment, X is CH$_2$, and R (i), wherein R$^x$ and R$^y$, at each occurrence, are each independently hydrogen or alkyl; r and s are independently 0, 1, or 2, wherein the total of r and s is 2 or 3; A is phenyl, wherein the phenyl, is unsubstituted or substituted with 1, 2, 3, or 4 substituents selected from alkyl, halogen, cyano, —OR$^{1a}$, —N(R$^b$)(R$^{3a}$), —N(R$^a$)C(O)R$^{1a}$, or haloalkyl; wherein and R$^{1a}$ and R$^{3a}$, at each occurrence, are each independently alkyl or haloalkyl; and R$^b$ is hydrogen, alkyl, or haloalkyl.

In a further embodiment, X is CH$_2$, and R (i), wherein R$^x$ and R$^y$ are each hydrogen; r and s are independently 0, 1, or 2, wherein the total of r and s is 2 or 3; A is phenyl, wherein the phenyl, is unsubstituted or substituted with 1, 2, or 3 substituents selected from alkyl, halogen, cyano, —OR$^{1a}$, —N(R$^b$)(R$^{3a}$), —N(R$^a$)C(O)R$^{1a}$, or haloalkyl; wherein R$^{1a}$ and R$^{3a}$, at each occurrence, are each independently alkyl or haloalkyl; and R$^b$ is hydrogen, alkyl, or haloalkyl.

Specific embodiments of compounds contemplated as part of the invention include, but are not limited to:

4-(thieno[2,3-c]pyridin-5-ylcarbonyl)-1,4-diazatricyclo[4.3.1.1$^{3,8}$]undecane;

4-(thieno[3,2-b]pyridin-5-ylcarbonyl)-1,4-diazatricyclo[4.3.1.1$^{3,8}$]undecane;

4-(5,5-dioxidodibenzo[b,d]thien-3-yl)-1,4-diazatricyclo[4.3.1.1$^{3,8}$]undecane;

4-(5-phenyl-1,3,4-oxadiazol-2-yl)-1,4-diazatricyclo[4.3.1.1$^{3,8}$]undecane;

4-(6-phenylpyridazin-3-yl)-1,4-diazatricyclo[4.3.1.1$^{3,8}$]undecane;

4-[6-(1-benzothien-5-yl)pyridazin-3-yl]-1,4-diazatricyclo[4.3.1.1$^{3,8}$]undecane;

4-(3-methoxybenzoyl)-1,4-diazatricyclo[4.3.1.1$^{3,8}$]undecane;

4-(1-naphthylacetyl)-1,4-diazatricyclo[4.3.1.1$^{3,8}$]undecane;

4-(pyridin-2-ylcarbonyl)-1,4-diazatricyclo[4.3.1.1$^{3,8}$]undecane;

4-(phenoxyacetyl)-1,4-diazatricyclo[4.3.1.1$^{3,8}$]undecane;

4-(3-chlorobenzoyl)-1,4-diazatricyclo[4.3.1.1$^{3,8}$]undecane;

N-[4-(1,4-diazatricyclo[4.3.1.1$^{3,8}$]undec-4-ylcarbonyl)phenyl]-N,N-dimethylamine;

4-[2-methylphenyl)acetyl]-1,4-diazatricyclo[4.3.1.1$^{3,8}$]undecane;

3-(1,4-diazatricyclo[4.3.1.1$^{3,8}$]undec-4-ylcarbonyl)benzonitrile;

4-(2-methylbenzoyl)-1,4-diazatricyclo[4.3.1.1$^{3,8}$]undecane;

N-[4-(1,4-diazatricyclo[4.3.1.1$^{3,8}$]undec-4-ylcarbonyl)phenyl]acetamide;

4-[(3-methylphenyl)acetyl]-1,4-diazatricyclo[4.3.1.1$^{3,8}$]undecane;

4-(2,5-dimethylbenzoyl)-1,4-diazatricyclo[4.3.1.1$^{3,8}$]undecane;

4-(3-phenylpropanoyl)-1,4-diazatricyclo[4.3.1.1$^{3,8}$]undecane;

N-[3-(1,4-diazatricyclo[4.3.1.1$^{3,8}$]undec-4-ylcarbonyl)phenyl]acetamide;

4-(4-ethylbenzoyl)-1,4-diazatricyclo[4.3.1.1$^{3,8}$]undecane;

4-{[2-(trifluoromethyl)phenyl]acetyl}-1,4-diazatricyclo[4.3.1.1$^{3,8}$]undecane;

4-(2,4-dimethylbenzoyl)-1,4-diazatricyclo[4.3.1.1$^{3,8}$]undecane;

4-(3-phenylbutanoyl)-1,4-diazatricyclo[4.3.1.1$^{3,8}$]undecane;

4-(1,2,3,4-tetrahydronaphthalen-2-ylcarbonyl)-1,4-diazatricyclo[4.3.1.1$^{3,8}$]undecane;

4-(4-ethoxybenzoyl)-1,4-diazatricyclo[4.3.1.1$^{3,8}$]undecane;

N-{4-[2-(1,4-diazatricyclo[4.3.1.1$^{3,8}$]undec-4-yl)-2-oxoethyl]phenyl}-N,N-dimethylamine;

4-(2,3-difluorobenzoyl)-1,4-diazatricyclo[4.3.1.1$^{3,8}$]undecane;

4-(3-methylbenzoyl)-1,4-diazatricyclo[4.3.1.1$^{3,8}$]undecane;

4-(2,5-dimethyl-3-furoyl)-1,4-diazatricyclo[4.3.1.1$^{3,8}$]undecane;

4-(pyridin-3-ylcarbonyl)-1,4-diazatricyclo[4.3.1.1$^{3,8}$]undecane;

4-(5-chloro-2-fluorobenzoyl)-1,4-diazatricyclo[4.3.1.1$^{3,8}$]undecane;

4-(3-methyl-2-furoyl)-1,4-diazatricyclo[4.3.1.1$^{3,8}$]undecane;

4-[(1-phenyl-1H-pyrazol-5-yl)carbonyl]-1,4-diazatricyclo[4.3.1.1$^{3,8}$]undecane;

4-(1H-indol-5-ylcarbonyl)-1,4-diazatricyclo[4.3.1.1$^{3,8}$]undecane;

4-(3,5-dimethoxybenzoyl)-1,4-diazatricyclo[4.3.1.1$^{3,8}$]undecane;

4-[(4-methylthien-2-yl)carbonyl]-1,4-diazatricyclo[4.3.1.1$^{3,8}$]undecane;

4-[(2,5-dimethoxyphenyl)acetyl]-1,4-diazatricyclo[4.3.1.1$^{3,8}$]undecane;

4-[(5-methylthien-2-yl)carbonyl]-1,4-diazatricyclo[4.3.1.1$^{3,8}$]undecane;

4-(2-fluorobenzoyl)-1,4-diazatricyclo[4.3.1.1$^{3,8}$]undecane;

4-[(2-fluorophenyl)acetyl]-1,4-diazatricyclo[4.3.1.1$^{3,8}$]undecane;

4-[4-(trifluoromethyl)benzoyl]-1,4-diazatricyclo[4.3.1.1$^{3,8}$]undecane;

4-(3,4-difluorobenzoyl)-1,4-diazatricyclo[4.3.1.1$^{3,8}$]undecane;

4-(thien-2-ylcarbonyl)-1,4-diazatricyclo[4.3.1.1$^{3,8}$]undecane;

4-[(5-methylpyrazin-2-yl)carbonyl]-1,4-diazatricyclo[4.3.1.1$^{3,8}$]undecane;

4-(2,3-dimethylbenzoyl)-1,4-diazatricyclo[4.3.1.1$^{3,8}$]undecane;

4-(quinolin-2-ylcarbonyl)-1,4-diazatricyclo[4.3.1.1$^{3,8}$]undecane;

4-(thien-2-ylacetyl)-1,4-diazatricyclo[4.3.1.1$^{3,8}$]undecane;

4-[(3-methoxyphenyl)acetyl]-1,4-diazatricyclo[4.3.1.1$^{3,8}$]undecane;
4-[(1-methyl-1H-pyrrol-2-yl)carbonyl]-1,4-diazatricyclo[4.3.1.1$^{3,8}$]undecane;
2-(1,4-diazatricyclo[4.3.1.1$^{3,8}$]undec-4-ylcarbonyl)phenol;
4-[(2-methoxypyridin-3-yl)carbonyl]-1,4-diazatricyclo[4.3.1.1$^{3,8}$]undecane;
4-(1H-pyrrol-2-ylcarbonyl)-1,4-diazatricyclo[4.3.1.1$^{3,8}$]undecane;
4-(3-chloro-4-fluorobenzoyl)-1,4-diazatricyclo[4.3.1.1$^{3,8}$]undecane;
4-(1H-indazol-3-ylcarbonyl)-1,4-diazatricyclo[4.3.1.1$^{3,8}$]undecane;
4-(5-chloro-2-methoxybenzoyl)-1,4-diazatricyclo[4.3.1.1$^{3,8}$]undecane;
4-(2,4-difluorobenzoyl)-1,4-diazatricyclo[4.3.1.1$^{3,8}$]undecane;
4-(thien-3-ylacetyl)-1,4-diazatricyclo[4.3.1.1$^{3,8}$]undecane;
4-(4-fluoro-3-methylbenzoyl)-1,4-diazatricyclo[4.3.1.1$^{3,8}$]undecane;
4-(2-furoyl)-1,4-diazatricyclo[4.3.1.1$^{3,8}$]undecane;
4-benzoyl-1,4-diazatricyclo[4.3.1.1$^{3,8}$]undecane;
4-(2-methoxybenzoyl)-1,4-diazatricyclo[4.3.1.1$^{3,8}$]undecane;
4-[5-(3-fluoro-4-methoxyphenyl)pyridin-3-yl]-1,4-diazatricyclo[4.3.1.1$^{3,8}$]undecane;
4-[5-(2,3-dihydro-1,4-benzodioxin-6-yl)pyridin-3-yl]-1,4-diazatricyclo[4.3.1.1$^{3,8}$]undecane;
N-{4-[5-(1,4-diazatricyclo[4.3.1.1$^{3,8}$]undec-4-yl)pyridin-3-yl]phenyl}-N,N-dimethylamine;
4-[5-(3,4,5-trimethoxyphenyl)pyridin-3-yl]-1,4-diazatricyclo[4.3.1.1$^{3,8}$]undecane;
4-[5-(3,5-dimethylisoxazol-4-yl)pyridin-3-yl]-1,4-diazatricyclo[4.3.1.1$^{3,8}$]undecane;
4-[5-(2,6-dimethoxyphenyl)pyridin-3-yl]-1,4-diazatricyclo[4.3.1.1$^{3,8}$]undecane;
4-(5-phenylpyridin-3-yl)-1,4-diazatricyclo[4.3.1.1$^{3,8}$]undecane;
4-[5-(4-methylphenyl)pyridin-3-yl]-1,4-diazatricyclo[4.3.1.1$^{3,8}$]undecane;
4-[5-(4-fluorophenyl)pyridin-3-yl]-1,4-diazatricyclo[4.3.1.1$^{3,8}$]undecane;
4-[5-(4-methoxyphenyl)pyridin-3-yl]-1,4-diazatricyclo[4.3.1.1$^{3,8}$]undecane;
4-{5-[4-(trifluoromethyl)phenyl]pyridin-3-yl}-1,4-diazatricyclo[4.3.1.1$^{3,8}$]undecane;
4-[5-(3-methylphenyl)pyridin-3-yl]-1,4-diazatricyclo[4.3.1.1$^{3,8}$]undecane;
4-[5-(3-fluorophenyl)pyridin-3-yl]-1,4-diazatricyclo[4.3.1.1$^{3,8}$]undecane;
4-[5-(3-methoxyphenyl)pyridin-3-yl]-1,4-diazatricyclo[4.3.1.1$^{3,8}$]undecane;
4-[5-(2-furyl)pyridin-3-yl]-1,4-diazatricyclo[4.3.1.1$^{3,8}$]undecane;
4-(5-thien-3-ylpyridin-3-yl)-1,4-diazatricyclo[4.3.1.1$^{3,8}$]undecane;
4-[5-(3,4-dimethoxyphenyl)pyridin-3-yl]-1,4-diazatricyclo[4.3.1.1$^{3,8}$]undecane;
4-(3,3'-bipyridin-5-yl)-1,4-diazatricyclo[4.3.1.1$^{3,8}$]undecane;
4-(3,4'-bipyridin-5-yl)-1,4-diazatricyclo[4.3.1.1$^{3,8}$]undecane;
4-[5-(2-methoxyphenyl)pyridin-3-yl]-1,4-diazatricyclo[4.3.1.1$^{3,8}$]undecane;
4-[5-(2,5-dimethoxyphenyl)pyridin-3-yl]-1,4-diazatricyclo[4.3.1.1$^{3,8}$]undecane;
4-[5-(2,4-dimethoxyphenyl)pyridin-3-yl]-1,4-diazatricyclo[4.3.1.1$^{3,8}$]undecane;
4-[5-(2-fluorophenyl)pyridin-3-yl]-1,4-diazatricyclo[4.3.1.1$^{3,8}$]undecane;
4-[5-(2-ethoxyphenyl)pyridin-3-yl]-1,4-diazatricyclo[4.3.1.1$^{3,8}$]undecane;
4-[5-(1,4-diazatricyclo[4.3.1.1$^{3,8}$]undec-4-yl)pyridin-3-yl]benzonitrile;
3-[5-(1,4-diazatricyclo[4.3.1.1$^{3,8}$]undec-4-yl)pyridin-3-yl]benzonitrile;
4-{5-[3-(trifluoromethyl)phenyl]pyridin-3-yl}-1,4-diazatricyclo[4.3.1.1$^{3,8}$]undecane;
4-[5-(1,3-benzodioxol-5-yl)pyridin-3-yl]-1,4-diazatricyclo[4.3.1.1$^{3,8}$]undecane;
4-(2'-methoxy-3,3'-bipyridin-5-yl)-1,4-diazatricyclo[4.3.1.1$^{3,8}$]undecane;
N-{3-[5-(1,4-diazatricyclo[4.3.1.1$^{3,8}$]undec-4-yl)pyridin-3-yl]phenyl}acetamide;
4-[5-(3,5-difluorophenyl)pyridin-3-yl]-1,4-diazatricyclo[4.3.1.1$^{3,8}$]undecane;
4-(6'-methoxy-3,3'-bipyridin-5-yl)-1,4-diazatricyclo[4.3.1.1$^{3,8}$]undecane;
4-[5-(2-methoxy-5-methylphenyl)pyridin-3-yl]-1,4-diazatricyclo[4.3.1.1$^{3,8}$]undecane;
4-[5-(4-methoxy-3-methylphenyl)pyridin-3-yl]-1,4-diazatricyclo[4.3.1.1$^{3,8}$]undecane;
4-[5-(3,4-difluorophenyl)pyridin-3-yl]-1,4-diazatricyclo[4.3.1.1$^{3,8}$]undecane;
1-{5-[5-(1,4-diazatricyclo[4.3.1.1$^{3,8}$]undec-4-yl)pyridin-3-yl]thien-2-yl}ethanone;
4-(5-pyrimidin-5-ylpyridin-3-yl)-1,4-diazatricyclo[4.3.1.1$^{3,8}$]undecane;
1-{2-[5-(1,4-diazatricyclo[4.3.1.1$^{3,8}$]undec-4-yl)pyridin-3-yl]phenyl}ethanone;
4-[5-(1H-indol-5-yl)pyridin-3-yl]-1,4-diazatricyclo[4.3.1.1$^{3,8}$]undecane;
4-[5-(1H-indol-4-yl)pyridin-3-yl]-1,4-diazatricyclo[4.3.1.1$^{3,8}$]undecane;
4-[5-(4-methoxyphenyl)-1,3-thiazol-2-yl]-1,4-diazatricyclo[4.3.1.1$^{3,8}$]undecane;
4-[5-(4-methylphenyl)-1,3-thiazol-2-yl]-1,4-diazatricyclo[4.3.1.1$^{3,8}$]undecane;
4-[5-(3-methylphenyl)-1,3-thiazol-2-yl]-1,4-diazatricyclo[4.3.1.1$^{3,8}$]undecane;
4-[5-(3-fluorophenyl)-1,3-thiazol-2-yl]-1,4-diazatricyclo[4.3.1.1$^{3,8}$]undecane;
4-[5-(2,5-dimethoxyphenyl)-1,3-thiazol-2-yl]-1,4-diazatricyclo[4.3.1.1$^{3,8}$]undecane;
4-[5-(4-fluorophenyl)-1,3-thiazol-2-yl]-1,4-diazatricyclo[4.3.1.1$^{3,8}$]undecane;
4-(6-chloro-1,3-benzothiazol-2-yl)-1,4-diazatricyclo[4.3.1.1$^{3,8}$]undecane;
4-(6-chloro-1,3-benzoxazol-2-yl)-1,4-diazatricyclo[4.3.1.1$^{3,8}$]undecane; or
4-(1,3-benzothiazol-2-yl)-1,4-diazatricyclo[4.3.1.1$^{3,8}$]undecane.

Another embodiment of this invention pertains to compounds of formula (I) wherein R is hydrogen, useful for the preparation of compounds of formula (I) wherein R is Ar$^1$, Ar$^2$—Ar$^3$, —(CH$_2$)$_q$Ar$^3$, —C(O)Ar$^3$, —C(O)Ar$^3$, —C(O)NR$^1$R$^2$, —C(O)—(CR$^x$R$^y$)$_q$—Ar$^3$, —C(O)—(CR$^x$R$^y$)$_q$—O—Ar$^3$, —C(O)—Ar$^2$—Ar$^3$, or (i).

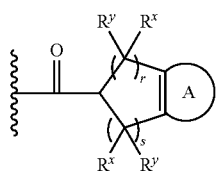

Specific embodiments contemplated as part of the invention include, but are not limited to compounds of formula (I), for example:

1,4-diazatricyclo[4.3.1.1$^{3,8}$]undecan-5-one or
1,4-diazatricyclo[4.3.1.1$^{3,8}$]undecane.

Compounds disclosed herein may contain asymmetrically substituted carbon or sulfur atoms, and accordingly may exist in, and be isolated as, single stereoisomers (e.g. single enantiomer or single diastereomer), mixtures of stereoisomers (e.g. any mixture of enantiomers or diastereomers) or racemic mixtures thereof. Individual optically-active forms of the compounds can be prepared for example, by synthesis from optically-active starting materials, by chiral synthesis, by enzymatic resolution, by biotransformation, or by chromatographic separation. It is to be understood that the present invention encompasses any racemic, optically-active, stereoisomeric form, or mixtures of various proportions thereof, which form possesses properties useful in the modulation of NNR activity, particularly α7NNRs, α4β2 NNRs, or both α7 and α4β2 NNRs. Where the stereochemistry of the chiral centers present in the chemical structures illustrated herein is not specified, the chemical structure is intended to encompass compounds containing either stereoisomer of each chiral center, and mixtures thereof.

Geometric isomers can exist in the present compounds. The invention contemplates the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen bond are designated as being of Z or E configuration and substituents around a cycloalkyl or heterocycle are designated as being of cis or trans configuration. It is to be understood that compounds disclosed herein may exhibit the phenomenon of tautomerism.

The compounds within this specification may be represented only by one of the possible tautomeric, geometric or stereoisomeric forms in naming of the compounds or formulae drawings. However, it is to be understood that the invention encompasses any tautomeric, geometric or stereoisomeric form, and mixtures thereof, and is not to be limited merely to any one tautomeric, geometric or stereoisomeric form utilized within the naming of the compounds or formulae drawings.

The present invention also includes isotopically-labeled compounds, which are identical to those recited in Formula I, but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, fluorine, and chlorine, such as but not limited to $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Compounds incorporating positron-emitting isotopes are useful in medical imaging and positron-emitting tomography (PET) studies for determining the distribution of receptors. Suitable positron-emitting isotopes that can be incorporated in compounds of formula (I) are $^{11}$C, $^{13}$N, $^{15}$O, and $^{18}$F. Isotopically-labeled compounds of formula (I) can generally be prepared by conventional techniques known to those skilled in the art or by processes analogous to those described in the accompanying Examples and Schemes using appropriate isotopically-labeled reagent in place of non-isotopically-labeled reagent. The radiolabeled compounds of the invention can be used as standards to determine the effectiveness of α7 NNR ligands in the binding assays, such as the assays described below.

c. Biological Data

To determine the effectiveness of representative compounds of this invention as ligands for α7 NNRs, the compounds of the invention were evaluated according to the [$^3$H]-DPPB binding assay or the [$^3$H]-methyllycaconitine (MLA) binding assay. To determine the effectiveness of representative compounds of this invention as ligands for α4β2 NNRs, the compounds of the invention were evaluated according to the [$^3$H]-cytisine binding assay, which were performed as described below.

Abbreviations which have been used in the descriptions of Biological Data that follow are: BSA for bovine serum albumin; BSS for balanced salt solution; HPLC for high-performance liquid chromatography; PEI for poly(ethyleneimine) solution; Tris for tris(hydroxymethyl)aminomethane; Tris-Cl for tris(hydroxymethyl)aminomethane hydrochloride.

(i) [$^3$H]-Cytisine Binding

Binding to α4β2 NNRs subtype was determined according to the conditions which were modified from the procedures described in Pabreza L. A., et al., Mol. Pharm. 1991, 39: 9-12. Membrane enriched fractions from rat brain minus cerebellum (ABS Inc., Wilmington, Del.) were slowly thawed at 4° C., washed and resuspended in 30 volumes of BSS-Tris buffer (120 mM NaCl/5 mM KCl/2 mM CaCl$_2$/2 mM MgCl$_2$/50 mM Tris-Cl, pH 7.4, 4° C.). Samples containing 100-200 µg of protein and 0.75 nM [$^3$H]-cytisine (30 C$_i$/mmol; Perkin Elmer/NEN Life Science Products, Boston, Mass.) were incubated in a final volume of 500 µL for 75 minutes at 4° C. Seven log-dilution concentrations of each compound were tested in duplicate. Non-specific binding was determined in the presence of 10 µM (−)-nicotine. Bound radioactivity was isolated by vacuum filtration onto prewetted glass fiber filter plates (Millipore, Bedford, Mass.) using a 96-well filtration apparatus (Packard Instruments, Meriden, Conn.) and were then rapidly rinsed with 2 mL of ice-cold BSS buffer (120 mM NaCl/5 mM KCl/2 mM CaCl$_2$/2 mM MgCl$_2$). Packard MicroScint-20® scintillation cocktail (40 µL) was added to each well and radioactivity determined using a Packard TopCount® instrument. The IC$_{50}$ values were determined by nonlinear regression in Microsoft Excel® software. K, values were calculated from the IC$_{50}$s using the Cheng-Prusoff equation, where $K_i = IC_{50}/(1+[Ligand]/K_D)$.

(ii) [$^3$H]-Methyllycaconitin (MLA) Binding

Binding conditions were similar to those for [$^3$H]-cytisine binding. Membrane enriched fractions from rat brain minus cerebellum (ABS Inc., Wilmington, Del.) were slowly thawed at 4° C., washed and resuspended in 30 volumes of BSS-Tris buffer (120 mM NaCl, 5 mM KCl, 2 mM $CaCl_2$, 2 mM $MgCl_2$, and 50 mM Tris-Cl, pH 7.4, 22° C.). Samples containing 100-200 µg of protein, 5 nM [$^3$H]-MLA (25 $C_i$/mmol; Perkin Elmer/NEN Life Science Products, Boston, Mass.) and 0.1% bovine serum albumin (BSA, Millipore, Bedford, Mass.) were incubated in a final volume of 500 µL for 60 minutes at 22° C. Seven log-dilution concentrations of each compound were tested in duplicate. Non-specific binding was determined in the presence of 10 µM MLA. Bound radioactivity was isolated by vacuum filtration onto glass fiber filter plates prewetted with 2% BSA using a 96-well filtration apparatus (Packard Instruments, Meriden, Conn.) and were then rapidly rinsed with 2 mL of ice-cold BSS. Packard MicroScint-20® scintillation cocktail (40 µL) was added to each well and radioactivity was determined using a Packard TopCount® instrument. The $IC_{50}$ values were determined by nonlinear regression in Microsoft Excel® software. $K_i$ values were calculated from the $IC_{50}$s using the Cheng-Prusoff equation, where $K_i=IC_{50}/(1+[Ligand]/K_D)$.

(iii) [$^3$H]-DPPB Binding

[$^3$H]-DPPB, [$^3$H]-(S,S)-2,2-dimethyl-5-(6-phenyl-pyridazin-3-yl)-5-aza-2-azonia-bicyclo[2.2.1]heptane iodide, binding to the α7 NNR subtype was determined using membrane enriched fractions from rat brain minus cerebellum or human cortex (ABS Inc., Wilmington, Del.) as described in Anderson, D. J.; et al., J. Pharmacol. Exp. Ther. 2008, 324: 179-187 which is incorporated herein by reference. Briefly, pellets were thawed at 4° C., washed and resuspended with a Polytron at a setting of 7 in 30 volumes of BSS-Tris buffer (120 mM NaCl, 5 mM KCl, 2 mM $CaCl_2$, 2 mM $MgCl_2$, and 50 mM Tris-Cl, pH 7.4, 4° C.). Seven log-dilution concentrations of test compounds containing 100-200 µg of protein, and 0.5 nM [$^3$H]-DPPB (62.8 Ci/mmol; R46V, Abbott Labs) were incubated in a final volume of 500 µL for 75 minutes at 4° C. in duplicate. Non-specific binding was determined in the presence of 10 µM methyllycaconitine. Bound radioactivity was collected on Millipore MultiScreen® harvest plates FB presoaked with 0.3% polyethyleneimine using a Packard cell harvester, washed with 2.5 mL ice-cold buffer, and radioactivity was determined using a Packard TopCount Microplate beta counter. $IC_{50}$ values were determined by nonlinear regression in Microsoft® Excel or Assay Explorer. $K_i$ values were calculated from the $IC_{50}$s using the Cheng-Prusoff equation, where $K_i=IC_{50}/(1+[Ligand]/K_D)$ and are shown in Table 1. [$^3$H]-DPPB was obtained according to the preparation procedures described below. Table 1. [$^3$H]-DPPB binding

TABLE 1

| [$^3$H]-DPPB binding | |
|---|---|
| Example | Ki (µM) |
| 1 | 0.701 |
| 3 | 0.0116 |
| 4 | 0.456 |
| 5 | 0.0023 |
| 8 | 0.0035 |
| 37 | >10 |
| 57 | 0.0236 |
| 90 | 0.0485 |
| 99 | >10 |
| 104 | 0.0263 |
| 105 | 0.1334 |
| 106 | 0.0264 |

TABLE 1-continued

| [$^3$H]-DPPB binding | |
|---|---|
| Example | Ki (µM) |
| 108 | 0.0377 |
| 110 | 0.0536 |
| 111 | 0.114 |
| 112 | 0.0355 |
| 113 | >10 |

(iv) [Methyl-$^3$H]2,2-Dimethyl-5-(6-phenyl-pyridazin-3-yl)-5-aza-2-azonia-bicyclo[2.2.1]heptane; iodide Preparation

[Methyl-3H]2,2-dimethyl-5-(6-phenyl-pyridazin-3-yl)-5-aza-2-azonia-bicyclo[2.2.1]heptane; iodide used in the [$^3$H]-DPPB binding assay above was prepared according to the following procedures.

Step 1: Preparation of t-Butyl(S,S)-5-(6-Phenyl-pyridazin-3-yl-2,5-diaza-bicyclo[2.2.1]heptane-2-carboxylate Triethylamine (20 mL) was added to a suspension of t-butyl(S,S)-2,5-diazabicyclo[2.2.1]heptane-2-carboxylate (3.43 g, 17.3 mmol, Aldrich Chemical Company) and 3-chloro-6-phenylpyridazine (3.30 g, 17.3 mmol, Aldrich Chemical Company) in toluene (50 mL) and the mixture was heated under nitrogen at 100° C. for 7 days. The dark mixture was cooled to room temperature, and the resulting precipitate was isolated by filtration, washed with toluene (15 mL) and dried under vacuum to provide the title compound as an off-white solid. The filtrate was concentrated and the residue was purified by column chromatography on silica gel, eluting with ethyl acetate, to provide additional product: MS (DCI/$NH_3$) m/z 353 (M+H)$^+$.

Step 2: Preparation of (S,S)-2-Methyl 5-(6-phenyl-pyridazin-3-yl-2,5-diaza-bicyclo[2.2.1]heptane The product obtained from Step 1 (3.41 g, 9.7 mmol) was dissolved in formic acid (20 mL) and treated with formalin (37% by weight, 1.0 g, 12.3 mmol). The mixture was heated at 100° C. for 1 hour, and the brown solution was cooled to room temperature and concentrated under vacuum. The residue was purified by column chromatography on silica gel, eluting with dichloromethane-methanol-ammonium hydroxide (95:5:1) to provide the title compound: MS (DCI/$NH_3$) m/z 267 (M+H)$^+$.

Step 3: Preparation of [$^3$H]-(S,S)-2,2-Dimethyl-5-(6-phenyl-pyridazin-3-yl-5-aza-2-azonia-bicyclo[2.2.1] heptane iodide ([$^3$H]-DPPB)

[$^3$H]Methyl iodide in toluene (250 mCi in 0.1 mL, 85 Ci/mmol, American Radiolabeled Chemicals, Inc.) was combined with a solution of the product obtained from Step 2 in dichloromethane (0.788 mg, 2.96 µmole in 0.45 mL). The vial was capped and the mixture was allowed to react overnight at room temperature. Methanol was added and the solvents were evaporated to give 42 mCi. The product was taken up in methanol for HPLC purification.

Step 4: Purification by High Performance Liquid Chromatography (HPLC)

About 7 mCi of [$^3$H]-DPPB was evaporated to dryness and the residue was dissolved in total about 4.5 mL acetonitrile:

water:trifluoroacetic acid (15:85:0.1). Approximately 0.9 mL per injection were made onto a Phenomenex® Luna® C18(2) column (5 micron, 250 mm×4.6 mm ID) using an Agilent HPLC system. [$^3$H]-DPPB was eluted by a gradient mobile phase from 10% B to 20% B in 20 minutes where Mobile Phase A=0.1% trifluoroacetic acid in water and Mobile Phase B=0.1% trifluoroacetic acid in acetonitrile at a flow rate of approximately 1 mL/minute. Peak detection and chromatograms were obtained with an Agilent variable wavelength UV detector set at 275 nm. The fractions containing [$^3$H]-DPPB were collected at approximately 14 minutes using an Agilent fraction collector. The fractions were combined and the solvents were evaporated in vacuo. The residue was dissolved in 200 proof ethanol (2 mL) to give 0.7 mCi.

Step 5: Determination of Purity and Specific Activity

[$^3$H]-DPPB was assayed using an Agilent 1100 series HPLC system consisting of a quaternary pump, an autosampler, and a photodiode array UV detector. A Packard Radiomatic A 500 radioactivity detector was connected to the HPLC system. For radiodetection, a 500 μL flow cell and a 3:1 ratio of Ultima-Flo M scintillation cocktail to HPLC mobile phase were used. The analyses were performed using a Phenomenex® Luna®C18(2) column (5 microns, 250 mm×4.6 mm ID). The mobile phase consisted of a gradient starting with 10% B and ramping to 20% B in 20 minutes followed by ramping to 90% B in 1 minute and hold at 90% B for 9 minutes, where Mobile Phase A=0.1% trifluoroacetic acid in water and Mobile Phase B=0.1% trifluoroacetic acid in acetonitrile. The flow rate was set at approximately 1 mL/minute and the UV detection was set at 275 nm.

Preferred compounds of the invention had K, values of from about 0.01 nanomolar to about 10 micromolar when tested by the [$^3$H]-MLA assay, many having a K, of less than 1 micromolar. Other preferred compounds demonstrated [$^3$H]-Cytisine binding values of compounds of the invention from about 0.01 nanomolar to at least 10 micromolar. Other preferred compounds demonstrated [$^3$H]-DPPB binding values of compounds of the invention from about 0.01 nanomolar to at least 10 micromolar. The most preferred compounds had binding affinity for either the α7 receptors, or the α4β2 receptors, or both in the range of 0.01-1000 nM. Some preferred compounds exhibited greater potency at α7 receptors compared to α4β2 receptors.

Compounds of the invention are ligands at α4β2, α7 NNRs, or both α4β2 and α7 NNRs that modulate function of α4β2, α7 NNRs, or both α4β2 and α7 NNRs by altering the activity of the receptor or signaling. The compounds can be inverse agonists that inhibit the basal activity of the receptor or antagonists that completely block the action of receptor-activating agonists. The compounds also can be partial agonists that partially block or partially activate the α4β2, α7, or both α4β2 and α7 NNR receptor or agonists that activate the receptor. Binding to α4β2, α7, or both α4β2 and α7 receptors also trigger key signaling processes involving various kinases and phosphatases and protein-protein interactions that are important to effects on memory, cytoprotection, gene transcription and disease modification.

d. Methods of Using the Compounds

Compounds and compositions of the invention are useful for modulating the effects of NNRs, and more particularly α7 NNRs, α4β2 NNRs, or both α7 and α4β2 NNRs. In particular, the compounds and compositions of the invention can be used for treating or preventing disorders modulated by α7 NNRs, or α4β2 NNRs, or both α7 and α4β2 NNRs. Typically, such disorders can be ameliorated by selectively modulating the α7 NNRs, α4β2 NNRs, or both α7 and α4β2 NNRs in a mammal, preferably by administering a compound or composition of the invention, either alone or in combination with one or more additional pharmaceutical agents, for example, as part of a therapeutic regimen.

Compounds for the method of the invention, including but not limited to those specified in the examples or otherwise specifically named, can modulate, and often possess an affinity for, NNRs, and more particularly α7 NNRs, α4β2 NNRs, or both α7 and α4β2 NNRs. As α7 NNRs, α4β2 NNRs, or both α7 and α4β2 NNRs ligands, the compounds of the invention can be useful for the treatment or prevention of a number of α7 NNR, α4β2 NNR, or both α7 and α4β2 NNR mediated diseases or conditions.

Specific examples of compounds that can be useful for the treatment or prevention of α7, α4β2, or both α7 and α4β2 NNRs mediated diseases or conditions include, but are not limited to, compounds described in the Compounds of the Invention and also in the Examples.

For example, α7 NNRs have been shown to play a significant role in enhancing cognitive function, including aspects of learning, memory and attention (Levin, E. D., J. Neurobiol. 2002, 53: 633-640). As such, α7 ligands are suitable for the treatment of conditions and disorders related to memory and/or cognition including, for example, attention deficit disorder, ADHD, AD, mild cognitive impairment, senile dementia, AIDS dementia, Pick's disease, dementia associated with Lewy bodies, and dementia associated with Down's syndrome, as well as CDS.

In addition, α7-containing NNRs have been shown to be involved in the cytoprotective effects of nicotine both in vitro (Jonnala, R. B., et al., J. Neurosci. Res. 2001, 66: 565-572) and in vivo (Shimohama, S. et al., Brain Res. 1998, 779: 359-363). More particularly, neurodegeneration underlies several progressive CNS disorders, including, but not limited to, Alzheimer's disease, Parkinson's disease, amyotrophic lateral sclerosis, Huntington's disease, dementia with Lewy bodies, as well as diminished CNS function resulting from traumatic brain injury. For example, the impaired function of α7 NNRs by β-amyloid peptides linked to Alzheimer's disease has been implicated as a key factor in development of the cognitive deficits associated with the disease (Liu, Q.-S., et al, Proc. Natl. Acad. Sci. USA 2001, 98: 4734-4739). α7 selective ligands can influence neuroprotective pathways leading to decreased phosphorylation of the tau protein, whose hyperphosphorylation is required for neurofibrillary tangle formation in various tau related pathologies such as Alzheimer's disease and various other dementias (Bitner et al., Soc. Neuroscience, 2006 abst 325.6). The activation of α7 NNRs has been shown to block this neurotoxicity (Kihara, T. et al., J. Biol. Chem. 2001, 276: 13541-13546). As such, selective ligands that enhance α7 activity can counter the deficits of Alzheimer's and other neurodegenerative diseases.

α7 NNRs also have been implicated in aspects of neurodevelopment, for example neurogenesis of the brain (Falk, L. et al., Developmental Brain Research 2003, 142:151-160; Tsuneki, H., et al., J. Physiol. (London) 2003, 547:169-179; Adams, C. E., et al., Developmental Brain Research 2002, 139:175-187). As such, α7 NNRs can be useful in preventing or treating conditions or disorders associated with impaired neurodevelopment, for example schizophrenia. (Sawa A., Mol. Med. 2003, 9:3-9).

Several compounds with high affinity for α4β2 NNRs have been shown to improve attentive and cognitive performance in preclinical models that are relevant to attention-deficit/ hyperactivity disorder (ADHD), a disease characterized by core symptoms of hyperactivity, inattentiveness, and impulsivity. For example, ABT-418, a full agonist at α4β2 NNRs, is efficacious in a variety of preclinical cognition models. ABT-418 administered transdermally, was shown in a controlled clinical trial in 32 adults to be effective in treating ADHD in general, and attentional/cognitive deficits in particular (Wilens, T. E.; et al., The American Journal of Psychiatry 1999, 156, 1931-1937). Likewise, ABT-418 showed a signal of efficacy in a pilot Alzheimer's disease trial. ABT-089, a α4β2 selective partial agonist, has been shown in rodent and primate animal models to improve attention, learning, and memory deficits. ABT-089 and another α4β2 agonist, ispronicline have shown efficacy in a pilot clinical trials (Wilens, T. E., et al., Biological Psychiatry 2006, 59, 1065-1070. Geerts, H., Curr. Opin. Invest. Drugs 2006, 7, 60-69.). In addition to cognition, compounds that interact with α4β2 NNRs such as ABT-594 and others are also efficacious in preclinical and clinical models of pain. As such, ligands that modulate both α7 and α4β2 activity can have broader spectrum of therapeutic efficacy in disease states such as those involving cognitive and attentive deficits, pain, neurodegenerative diseases and others.

Schizophrenia is a complex disease that is characterized by abnormalities in perception, cognition, and emotions. Significant evidence implicates the involvement of α7 NNRs in this disease, including a measured deficit of these receptors in post-mortem patients (Sawa A., Mol. Med. 2003, 9:3-9; Leonard, S., Eur. J. Pharmacol. 2000, 393: 237-242). Deficits in sensory processing (gating) are one of the hallmarks of schizophrenia. These deficits can be normalized by nicotinic ligands that operate at the α7 NNR (Adler L. E. et al., Schizophrenia Bull. 1998, 24: 189-202; Stevens, K. E. et al., Psychopharmacology 1998, 136: 320-327). More recent studies have shown that α4β2 nicotinic receptor stimulation also contributes to the effects of nicotine in the DBA/2 mouse model of sensory gating (Radek et al., Psychopharmacology (Berl). 2006 187:47-55). Thus, α7 and α7/α4β2 ligands demonstrate potential in the treatment schizophrenia.

A population of α7 or α4β2 NNRs in the spinal cord modulate neurotransmission that has been associated with the pain-relieving effects of nicotinic compounds (Cordero-Erausquin, M., et al., Proc. Natl. Acad. Sci. USA 2001, 98:2803-2807). The α7 NNR or and α7/α4β2 ligands demonstrate therapeutic potential for the treatment of pain states, including acute pain, acute pain, chronic pain, neuropathic pain, nociceptive pain, allodynia, inflammatory pain, inflammatory hyperalgesia, post herpetic neuralgia, neuropathies, neuralgia, diabetic neuropathy, HIV-related neuropathy, nerve injury, rheumatoid arthritic pain, osteoarthritic pain, burns, back pain, eye pain, visceral pain, cancer pain, dental pain, headache, migraine, carpal tunnel syndrome, fibromyalgia, neuritis, sciatica, pelvic hypersensitivity, pelvic pain, post operative pain, post stroke pain, and menstrual pain.

Compounds of the invention are particularly useful for treating and preventing a condition or disorder affecting memory, cognition, neurodegeneration, neurodevelopment, and schizophrenia.

Cognitive impairment associated with schizophrenia (CDS) often limits the ability of patients to function normally, a symptom not adequately treated by commonly available treatments, for example, treatment with an atypical antipsychotic (Rowley, M. et al., J. Med. Chem. 2001 44: 477-501). Such cognitive deficit has been linked to dysfunction of the nicotinic cholinergic system, in particular with decreased activity at α7 receptors (Friedman, J. I. et al., Biol. Psychiatry, 2002, 51: 349-357). Thus, activators of α7 receptors can provide useful treatment for enhancing cognitive function in schizophrenic patients who are being treated with atypical antipsychotics. Accordingly, the combination of an α7 NNR ligand and one or more atypical antipsychotic would offer improved therapeutic utility. Specific examples of suitable atypical antipsychotics include, but are not limited to, clozapine, risperidone, olanzapine, quietapine, ziprasidone, zotepine, iloperidone, and the like.

Compounds of the invention may be administered alone or in combination (i.e. co-administered) with one or more additional pharmaceutical agents. Combination therapy includes administration of a single pharmaceutical dosage formulation containing one or more of the compounds of invention and one or more additional pharmaceutical agents, as well as administration of the compounds of the invention and each additional pharmaceutical agent, in its own separate pharmaceutical dosage formulation. For example, a compound of formula (I) and one or more additional pharmaceutical agents, may be administered to the patient together, in a single oral dosage composition having a fixed ratio of each active ingredient, such as a tablet or capsule; or each agent may be administered in separate oral dosage formulations.

Where separate dosage formulations are used, compounds of the invention and one or more additional pharmaceutical agents may be administered at essentially the same time (e.g., concurrently) or at separately staggered times (e.g., sequentially).

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salts, esters, amides, prodrugs, or salts of prodrugs thereof. Compounds of the invention can also be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal range from about 0.10 μg/kg body weight to about 100 mg/kg body weight. More preferable doses can be in the range of from about 0.10 μg/kg body weight to about 10 mg/kg body weight. If desired, the effective daily dose can be divided into multiple doses for purposes of administration. Consequently, single dose compositions may contain such amounts or submultiples thereof to make up the daily dose.

e. Pharmaceutical Compositions

The invention also provides pharmaceutical compositions comprising of compounds of the invention, or pharmaceutically acceptable salts, amides, esters, prodrugs, or salts of prodrugs thereof, formulated together with one or more pharmaceutically acceptable carriers.

The compounds identified by the methods described hereinabove may be administered as the sole pharmaceutical agent or in combination with one or more other pharmaceutical agents where the combination causes no unacceptable adverse effects. For example, the compounds of this invention can be combined with an atypical antipsychotic. Specific examples of suitable atypical antipsychotics include, but are not limited to, clozapine, risperidone, olanzapine, quietapine, ziprasidone, zotepine, iloperidone, and the like. Thus, the present invention also includes pharmaceutical compositions which are comprised of therapeutically effective amount of compounds identified by the methods described herein, or pharmaceutically acceptable salts, prodrugs or salts of prodrugs thereof, one or more pharmaceutical agents as disclosed hereinabove, and one or more pharmaceutically acceptable carriers.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The pharmaceutical compositions can be formulated for oral administration in solid, semi-solid or liquid form.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It also can be desirable to include isotonic agents, for example, sugars, sodium chloride and the like. Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, may depend upon crystal size and crystalline form. Alternatively, a parenterally administered drug form can be administered by dissolving or suspending the drug in an oil vehicle.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions can be formulated according to the known art using suitable dispersing or wetting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof.

In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They can optionally contain opacifying agents and can also be of a composition that releases the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, eardrops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this invention. Aqueous liquid compositions of the invention also are particularly useful.

The compounds of the invention can be used in the form of pharmaceutically acceptable salts derived from inorganic or organic acids.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Examples of acids which can be employed to form pharmaceutically acceptable acid addition salts include such inorganic acids as hydrochloric acid, hydrobromic acid, sulfuric acid and phosphoric acid and such organic acids as benzenesulfonic acid, citric acid, gluconic acid, maleic acid, oxalic acid and succinic acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylammonium, dimethylammonium, trimethylammonium, triethylammonium, diethylammonium, ethylammonium and the like. Other representative organic amines useful for the formation of base addition salts include ethylenediamine, ethanolamine, diethanolamine, piperidine, and piperazine.

Compounds of the invention may exist as prodrugs. Prodrugs of the invention can be rapidly transformed in vivo to a parent compound of the invention, for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The invention also contemplates pharmaceutically acceptable compounds that when administered to a patient in need thereof may be converted through in vivo biotransformation into compounds of formula (I).

f. General Synthesis

This invention is intended to encompass compounds of the invention when prepared by synthetic processes or by metabolic processes. Preparation of the compounds of the invention by metabolic processes include those occurring in the human or animal body (in vivo) or processes occurring in vitro.

The synthesis of compounds of formula (I) are exemplified in Schemes 1-5.

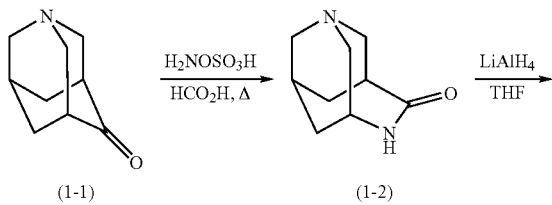

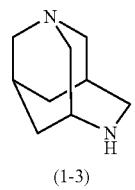

As outlined in Scheme 1, a compound of formula (1-2) can be prepared from a compound of formula (1-1) (A description of the synthesis can be found in Becker, D. P.; Flynn, D. L. Synthesis, 1992, 1080-1082.) by treatment with hydroxylamine-O-sulfonic acid in refluxing formic acid as described in Example 1. Compound (1-2) can then be reduced with lithium aluminum hydride in tetrahydrofuran initially at 0° C. and then with warming to reflux to produce compound (1-3) as described in Example 2.

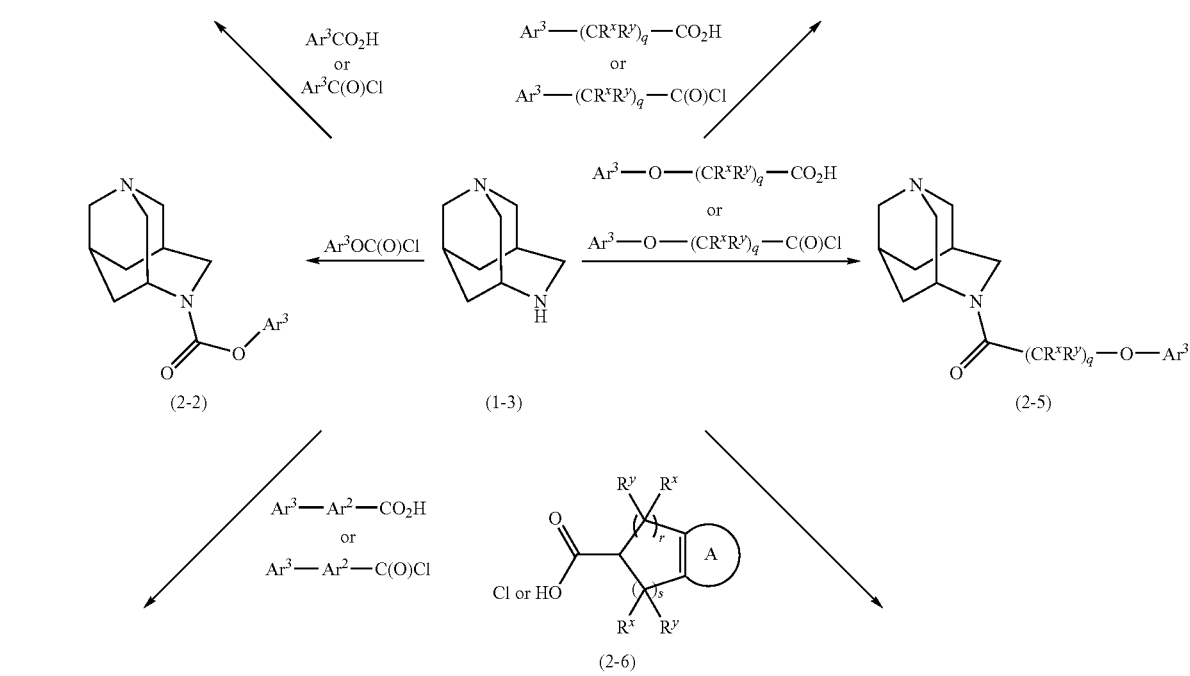

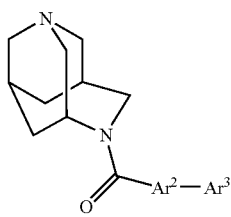

(2-3)

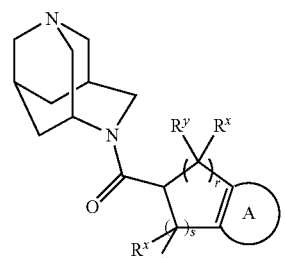

(2-7)

As described in Scheme 2, compounds of formula (2-1), (2-2), (2-3), (2-4), (2-5), and (2-7), wherein A, Ar², Ar³, R$^x$, R$^y$, q, r, and s are as described in the Summary of the Invention, can be prepared from compounds of formula (1-3). Compounds of formula (1-3) are treated with a carboxylic acid (Ar³CO₂H, Ar³—Ar²—CO₂H, Ar³—(CR$^x$R$^y$)$_q$—CO₂H, Ar³—O—(CR$^x$R$^y$)$_q$—CO₂H, or a carboxylic acid of formula (2-6)) utilizing conditions known to those skilled in the art which couple carboxylic acids to amines to generate amides will provide compounds of formula (2-1), (2-3), (2-4), (2-5) or (2-7) which are representative of compounds of formula (I). Examples of conditions known to generate amides from a mixture of a carboxylic acid and an amine include but are not limited to adding a coupling reagent such as but not limited to N-(3-dimethylaminopropyl)-N'-ethylcarbodiimide hydrochloride (EDCI, EDAC), 1,-dicyclohexylcarbodiimide (DCC), bis(2-oxo-3-oxazolidinyl)phosphinic chloride (BOPCl), O-(7-azabenzotriazol-1-yl)-N,N,N',N'-tetramethyluronium hexafluorophosphate (HATU), O-benzotriazol-1-yl-N,N,N',N'-tetramethyluronium tetrafluoroborate (TBTU). The coupling reagents may be added as a solid, a solution or as the reagent bound to a solid support resin. In addition to the coupling reagents, auxiliary-coupling reagents may facilitate the coupling reaction. Auxiliary coupling reagents that are often used in the coupling reactions include but are not limited to 4-dimethylaminopyridine (DMAP), 1-hydroxy-7-azabenzotriazole (HOAT) and 1-hydroxybenzotriazole (HOBT). The coupling reaction may be carried out in solvents such as but not limited to tetrahydrofuran, N,N,-dimethylformamide, pyridine and ethyl acetate. The reaction can be conducted in the presence of a base such as triethylamine or diisopropylethylamine. The reaction may be conducted at ambient or elevated temperatures.

Alternatively, the carboxylic acid may initially be converted to an acid chloride (Ar³C(O)Cl, Ar³—Ar²—C(O)Cl, Ar³—(CR$^x$R$^y$)$_q$—C(O)Cl, Ar³—O—(CR$^x$R$^y$)$_q$—C(O)Cl, or a carboxylic acid chloride of formula (2-6)), typically by suspending the carboxylic acid in a solvent such as dichloromethane and then adding oxalyl chloride and a catalytic amount of N,N,-dimethylformamide. The solvent may be removed by evaporation, and the acid chloride redissolved in pyridine. Addition of a compound of formula (1-3) in the presence of Hunig's base will furnish compounds of formula (2-1), (2-3), (2-4), (2-5) or (2-7) which are representative of compounds of formula (I). The reaction may be conducted at ambient or elevated temperatures over a period ranging from several hours to several days.

Compounds of formula (1-3) can also be converted to compounds of formula (2-2). Accordingly, compounds of formula (1-3) can be treated with a carbonochloridate (Ar³OC(O)Cl) in the presence of an amine base as triethyl amine, diisopropylethylamine or pyridine or alternatively an inorganic base such as sodium bicarbonate in water-dioxane in such solvents as N,N,-dimethylformamide or tetrahydrofuran. Compounds of formula (2-2) are representative of compounds of formula (I).

Scheme 3

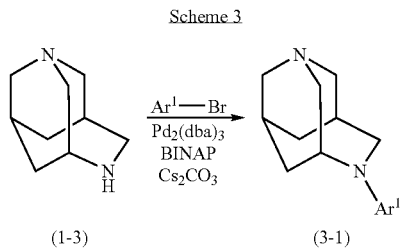

(1-3)                    (3-1)

As described in Scheme 3, compounds of formula (3-1), wherein Ar¹ is as described in the Summary of the Invention, can be prepared from compounds (1-3). A catalyst solution can be prepared by mixing tris(dibenzylideneacetone)dipalladium(0) (Pd₂(dba)₃) and racemic 2,2'-bis(diphenylphosphino)-1,1'-binaphthyl (BINAP) in toluene (4 mL) and heating the mixture to 80° C. for 15 minutes to 1 hour. The solution was cooled, and then compound (1-3) and the aryl bromide or heteroaryl bromide (Ar¹—Br) in toluene can be added. A base such as cesium carbonate is then added, and the reaction mixture was purged with nitrogen and heated to 80-85° C. for 16-48 hours to supply compounds of formula (3-1) which are representative of compounds of formula (I).

Scheme 4

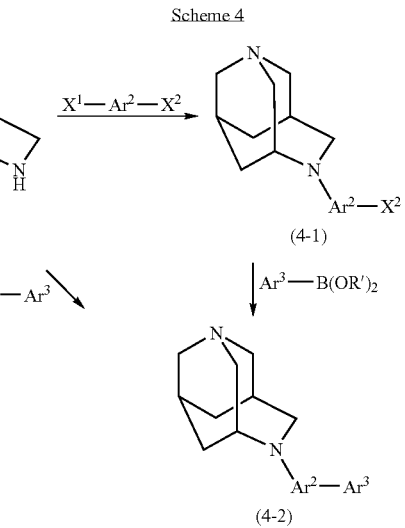

As described in Scheme 4, compound (1-3) can be converted to compounds of formula (4-2) in a one-step or two-step process. A solution of compound (1-3) in dry toluene can be treated with $X^1$—$Ar^3$—$X^2$; wherein $Ar^3$ is as described in the Summary of the Invention and $X^1$ and $X^2$ are independently chlorine, bromine, iodine or triflate; a catalyst such as tris(dibenzylideneacetone)dipalladium(0) ($Pd_2(dba)_3$), [1,1'-bis(diphenylphosphino)ferrocene]dichloropalladium(II), complex with dichloromethane or palladium(II) acetate; a ligand such as 1,3-bis(2,6-di-1-propylphenyl)imidazolium chloride or 2,2'-bis(diphenylphosphino)-1,1'-binaphthyl; and a base such as sodium tert-butoxide. The mixture is purged with nitrogen and then heated to 80-110° C. for 8 hours to 24 hours to provide compounds of formula (4-1). An example of $X^1$—$Ar^3$—$X^2$ is but is not limited to 3,6-dichloropyridazine, 3,5-dibromopyridine, or 2,5-dibromothiazole.

Compounds of formula (4-1) can then be converted to compounds of formula (4-2) under Suzuki reaction conditions. Accordingly, compounds of formula (4-1) can be treated with a boronic acid or borolane; wherein each R' is hydrogen, alkyl or taken to together with the boron and oxygen atoms form 4,4,5,5-tetramethyl-1,3,2-dioxaborolane; a catalyst such as dichlorobis(triphenylphosphine)palladium or [1,1'-bis(diphenylphosphino)ferrocene]dichloropalladium (II), complex with dichloromethane; a ligand such as (2-biphenyl)dicyclohexylphosphine or 2,2'-bis(diphenylphosphino)-1,1'-binaphthyl; and a base such as sodium carbonate or potassium carbonate in a mixture of ethanol, dioxane and water with subsequent heating in a microwave reactor to 100-175° C. for 5 to 30 minutes to give compounds of formula (4-2) which are representative of compounds of formula (I).

Other reagents are suitable for Suzuki reactions. The reaction typically requires the use of a base and a catalyst. Examples of other bases include but are not limited to potassium carbonate, potassium tert-butoxide, cesium carbonate, and cesium fluoride. Examples of catalysts include but are not limited to tetrakis(triphenylphosphine)palladium(0), [1,1'-bis(diphenylphosphino)ferrocene]dichloropalladium(II) complex with dichloromethane, tris(dibenzylideneacetone) dipalladium(0), and palladium(II) acetate. The reaction may be conducted in a solvent such as but not limited to water, dioxane, 1,2-dimethoxyethane, N,N-dimethylformamide, toluene, ethanol, tetrahydrofuran and the like or mixtures thereof. The reaction may be conducted at ambient or elevated temperatures with either conventional or microwave heating.

Compound (1-3) can be reacted with $X^1$—$Ar^2$—$Ar^3$ to provide compounds of formula (4-2) in one step. $Ar^3$ and $Ar^3$ are as defined in the Summary of the Invention and $X^1$ is chlorine, bromine, iodine or triflate. Compounds of formula $X^1$—$Ar^2$—$Ar^3$ are commercially available or can be prepared by methodology known to one skilled in the art. Compound (1-3) and compounds of formula $X^1$—$Ar^2$—$Ar^3$ can be combined with a catalyst such as tris(dibenzylideneacetone)dipalladium(0), a ligand such as 1,3-bis(2,6-di-iso-propylphenyl)imidazolium chloride, and a base such as sodium tert-butoxide in a solvent such as toluene or dioxane heated to 80-100° C. for 6 to 48 hours to provide compounds of formula (4-2) which are representative of compounds of formula (I).

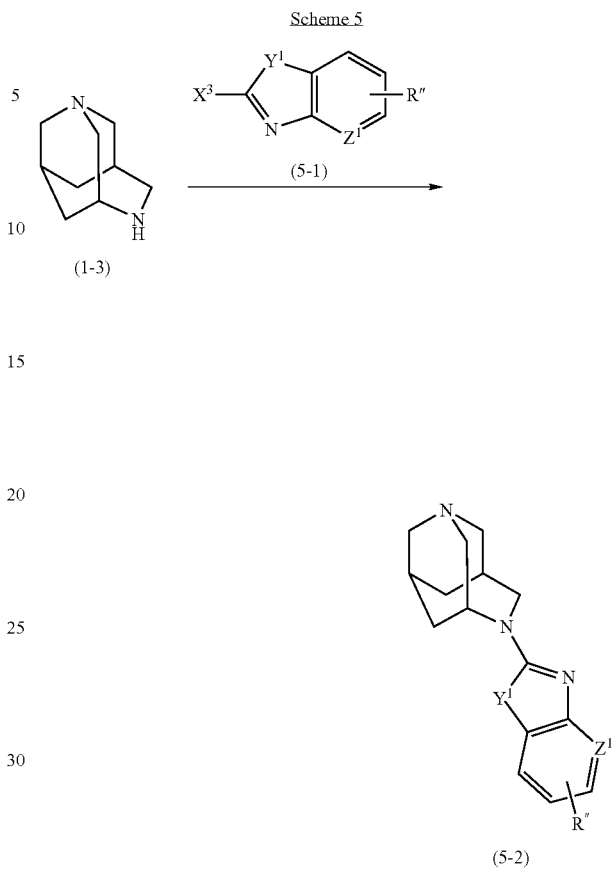

Scheme 5

As described in Scheme 4, compounds of formula (5-2) can be prepared from compound (1-3). Compounds of formula (5-1) have the structure indicated above and wherein $X^3$ is chloro or —$SCH_3$, $Y^1$ is O or S, $Z^1$ is CH or N, and R" is hydrogen, alkyl, halo, cyano, alkoxy, haloalkyl, or nitro. Accordingly, compound (1-3) can be reacted with compounds of formula (5-1) in the presence of a base such as triethylamine, diisopropylethylamine, pyridine, 2,6-lutidine, sodium hydroxide, potassium hydroxide, sodium carbonate, potassium carbonate, cesium carbonate, sodium tert-butoxide, potassium tert-butoxide, or 1,8-diazabicyclo[5.4.0]undec-7-ene in a solvent such as water, methanol, ethanol, isopropanol, acetonitrile, dichloromethane, chloroform, 1,2-dichloroethane, tetrahydrofuran, diethyl ether, dioxane, 1,2-dimethoxyethane, benzene, toluene, N,N-dimethylformamide, or dimethyl sulfoxide at a temperature from 50° C. to 150° C. to provide compounds of formula (5-2). Alternatively, compounds of formula (5-1), wherein $X^3$ is chloro can be coupled with compounds of formula (1-3) in the presence of a catalyst such as tris(dibenzylideneacetone) dipalladium(0), ligand such as 2,2'-bis(diphenylphosphino)-1,1'-binaphthyl, and base such as sodium t-butoxide in a heated solvent such as toluene to give compounds of formula (5-2). The heating can be accomplished by conventional methods or with microwave irradiation. Compounds of formula (5-2) are representative of compounds of formula (I).

Scheme 6

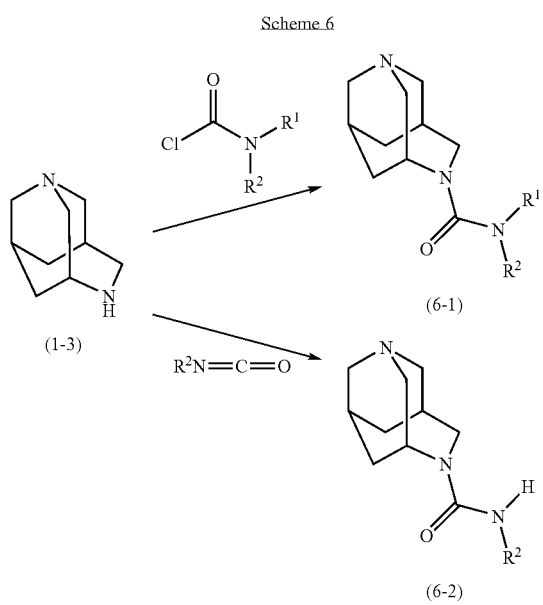

As described in Scheme 6, compounds of formula (6-1) and (6-2), wherein $R^1$ and $R^2$ are as described in the Summary of the Invention, can be prepared from compound (1-3). Accordingly, compound (1-3) can be reacted with compounds of formula $ClC(O)NR^1R^2$ in the presence of a base such as triethylamine or diisopropylethylamine in an optionally heated solvent such as dichloromethane, chloroform, 1,2-dichloroethane, tetrahydrofuran, or N,N-dimethylacetamide to give compounds of formula (6-1) which are representative of compounds of formula (I).

Alternatively, compound (1-3) can be reacted with compounds of formula $R^2NCO$ in the presence of a base such as triethylamine or diisopropylethylamine in an optionally heated solvent such as chloroform or toluene to give compounds of formula (6-2) which are representative of compounds of formula (I).

Scheme 7

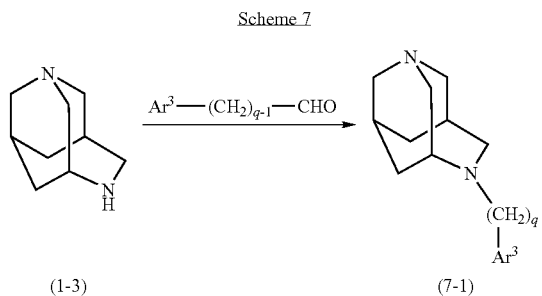

As described in Scheme 7, compounds of formula (7-1), wherein q and $Ar^a$ are as described in the Summary of the Invention, can be prepared from compounds of formula (1-3). Reductive amination of compounds of formula (1-3) with aldehydes of formula $Ar^a$—$(CH_2)_{q-1}$—CHO give compounds of formula (7-1) which are representative of compound of formula (I). The reductive amination can be performed by combining the amine and aldehyde in the presence of sodium cyanoborohydride or triacetoxyborohydride in acetic acid, methanol, dichloromethane, or 1,2-dichloroethane or combinations thereof. The reaction mixture can optionally be heated, and the reductant can be optionally attached to a solid support.

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the conventional manner, e.g., by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Chemical Synthesis ($3^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

g. Examples

The compounds and processes of the present invention will be better understood by reference to the following Examples, which are intended as an illustration of and not a limitation upon the scope of the application.

Abbreviations: DCI for desorption chemical ionization; HPLC for high-performance liquid chromatography; TLC for thin layer chromatography; and LC-MS for liquid chromatography/mass spectrometry.

LC-MS: Unless otherwise stated, the LC-MS measurements were obtained using one of the following methods.

LC-MS Method A: Agilent 1200 HPLC/6100 SQ System according to the following conditions: Mobile Phase A=water (0.05% trifluororacetic acid), B=acetonitrile (0.05% trifluororacetic acid); Gradient=5%-95% B in 1.2 minutes; Flow rate=1.8 mL/minute; Column: XBridge, C18, 3.5 nm, 50×4.6 mm; Oven temperature: 50° C.

LC-MS Method B: Agilent 1200 HPLC/6100 SQ System according to the following conditions: Mobile Phase A=water (0.1% Ammonia), B=acetonitrile; Gradient=5%-95% B in 1.2 minutes; flow rate=1.8 mL/minute; Column: XBridge, C18, 3.5 µm 50×4.6 mm; Oven temperature: 50° C.

LC-MS Method C: Agilent 1200 HPLC/1956 SQ System according to the following conditions: Mobile Phase A=water (0.1% formic Acid), B=acetonitrile (0.1% formic Acid); Gradient=5%-95% B in 1.2 minutes; flow rate=1.8 mL/minute; Column: XBridge, C18, 3.5 µm, 50×4.6 mm; Oven temperature: 50° C.

LC-MS Method D: Agilent 1200 HPLC/1956 SQ System according to the following conditions: Mobile Phase A=water (0.1% formic Acid), B=acetonitrile (0.1% formic Acid); Gradient=5%-95% B in 1.7 minutes; Flow rate=2.3 mL/minute; Column: XBridge, C18, 3.5 µm, 50×4.6 mm; Oven temperature: 50° C.

Preparative HPLC: Unless otherwise stated, the preparative HPLC purifications were carried out as follows to afford the target compounds [Gilson-GX281 HPLC system; Column: Shimadzu Shim-Pack PRC-ODS, 20×250 mm, 15 µm; Mobile Phase A=water (0.05% trifluoroacetic acid), B=acetonitrile, gradient: 30-60% B in 9 minutes; Flow rate 30 mL/minute; Detection wavelength 214 nm and 254 nm].

General Method A (Amide Formation)

To a solution of the carboxylic acid (1.2 equivalents) in N,N-dimethylformamide (4 mL) was added 1-hydroxybenzotriazole (HOBt; 1.0 equivalent), N-(3-dimethylaminopropyl)-N'-ethylcarbodiimide hydrochloride (EDCI; 1.2 equivalents) and N,N-diisopropyl-N-ethylamine (3.0 equivalents). After 30 minutes, the product of Example 2 (80 mg, 1.0 equivalent) was added and the reaction mixture was stirred at 20-25° C. for 2 days. The reaction mixture was concentrated under vacuum, and the residue was purified by either preparative TLC or preparative HPLC to afford the target compound.

General Method B (Bromopyridine Suzuki Coupling)

To a solution of the product of Example 65A (80 mg, 1.0 equivalent) in dioxane-water (6:1, 4 mL) was added the aryl- or heteroarylboronic acid, potassium carbonate (2 equivalents), and [1,1'-bis(diphenylphosphino)ferrocene]dichloropalladium(II), complex with dichloromethane (0.1 equivalents). The reaction mixture was stirred at 80° C. overnight. The reaction mixture was concentrated, and the residue was purified by either preparative TLC or preparative HPLC to afford the target compound.

General Method C (Bromothiazole Suzuki Coupling)\

To a solution of the product of Example 105A (100 mg, 0.318 mmol; 1.0 equivalent) in dioxane-water (6:1, 4 mL) was added the aryl- or heteroarylboronic acid (1.2 equivalents), potassium carbonate (88 mg, 0.636 mmol), and [1,1'-bis(diphenylphosphino)ferrocene]dichloropalladium(II), complex with dichloromethane (26 mg, 0.0318 mmol). The reaction mixture was stirred at 80° C. overnight. The reaction mixture was concentrated and the residue was purified by either preparative TLC or preparative HPLC.

Example 1

1,4-diazatricyclo[4.3.1.1$^{3,8}$]undecan-5-one

Example 1A 1,4-diazatricyclo[4.3.1.1$^{3,8}$]undecan-5-one

A solution of azaadamantan-4-one (2.0 g, 13.2 mmol; Synthesis 1992, 1080) in formic acid (10 mL) at room temperature was treated with a solution of hydroxylamine-O-sulfonic acid (2.24 g, 19.8 mmol; Aldrich) in formic acid (7 mL) added dropwise. The resulting mixture was then heated at reflux for 3.5 hours. After cooling the reaction mixture to room temperature, the solvent was removed under reduced pressure, and the resulting oil was diluted with 1 NNaOH and extracted with chloroform (3×). The combined organic extracts were washed with brine, dried ($Na_2SO_4$), filtered, and concentrated. The crude material was purified by flash chromatography over silica gel (115 g), eluting with 5-10% methanol (containing 1% ammonium hydroxide)-chloroform to afford the title compound: MS (DCI/$NH_3$) m/z 167 $(M+H)^+$, 184 $(M+NH_4)^+$.

Example 1B 1,4-diazatricyclo[4.3.1.1$^{3,8}$]undecan-5-one 4-methyl-benzenesulfonate The product of Example 1A (0.25 g, 15 mmol) was dissolved in ethyl acetate (12 mL) and ethanol (1 mL) at room temperature. A solution of p-toluenesulfonic acid monohydrate (0.29 g, 1.5 mmol; Aldrich) in ethyl acetate (2 mL) was added and the mixture was stirred for 2 hours. The resulting solid was collected by filtration, washed sequentially with ethyl acetate and ether, and dried overnight at 110° C. under high vacuum to afford the title compound: $^1$H NMR (300 MHz, $CD_3OD$) δ ppm 1.93-2.08 (m, 2 H) 2.18-2.34 (m, 3 H) 2.37 (s, 3 H) 2.83 (s, 1 H) 3.52 (t, J=13.1 Hz, 2 H) 3.66 (s, 3 H) 3.68-3.80 (m, 2 H) 3.85 (s, 1 H) 7.23 (d, J=8.1 Hz, 2 H) 7.70 (d, J=8.1 Hz, 2 H); MS (DCI/$NH_3$) m/z 167 $(M+H)^+$, 184 $(M+NH_4)^+$.

Example 2

1,4-diazatricyclo[4.3.1.1$^{3,8}$]undecane

A solution of the product of Example 1A (5.56 g, 35 mmol) in tetrahydrofuran (100 mL) was chilled to 0° C. and treated with lithium aluminum hydride (1.67 g, 44 mmol; Aldrich) added portionwise over 45 minutes. The resulting mixture was allowed to warm gradually to room temperature, then heated at reflux for 1 hour. The reaction was cooled again to 0° C. and quenched by the careful addition of sodium sulfate decahydrate (3.34 g, 10 mmol; Aldrich). After the mixture was stirred overnight, it was filtered through a bed of diatomaceous earth washing with excess ethyl acetate followed by chloroform. The filtrate and combined organic washes were concentrated, and the resulting crude material was filtered through a short plug of silica gel (100 mL), eluting with 4-12% methanol (containing 1% ammonium hydroxide)-chloroform, collecting all fractions to afford the title compound: $^1$H NMR (300 MHz, CDCl$_3$) δ ppm 1.64 (d, J=11.9 Hz, 3 H) 1.91-2.20 (m, 4 H) 2.56-2.96 (m, 4 H) 3.01-3.38 (m, 5 H); MS (DCI/NH$_3$) m/z 153 (M+H)$^+$.

Example 3

4-(thieno[2,3-c]pyridin-5-ylcarbonyl)-1,4-diazatricyclo[4.3.1.1$^{3,8}$]undecane Example 3A 4-(thieno[2,3-c]pyridin-5-ylcarbonyl)-1,4-diazatricyclo[4.3.1.1$^{3,8}$]undecane trifluoroacetate The product of Example 2 (0.20 g, 1.3 mmol) was stirred in tetrahydrofuran (10 mL) as thieno[2,3-c]pyridine-5-carboxylic acid (0.26 g, 1.4 mmol; Tetrahedron Lett. 1999, 40, 7935) and 1-hydroxybenzotriazole (0.36 g, 2.6 mmol; Aldrich) were added. After stirring for 5 minutes, N,N'-dicyclohexylcarbodiimide (DCC; 0.30 g, 1.4 mmol; Aldrich) was added, and the reaction was stirred for 24 hours. The solvent was removed under vacuum and the product was purified by preparative HPLC [Waters XTerra RP18 30×100 mm column, 5 µm, flow rate 40 mL/min, 5-50% gradient of acetonitrile in 0.1% aqueous trifluoroacetic acid] to afford the title compound as the corresponding trifluoroacetate: MS (DCI/NH$_3$) m/z 314 (M+H)$^+$.

Example 3B 4-(thieno[2,3-c]pyridin-5-ylcarbonyl)-1,4-diazatricyclo[4.3.1.1$^{3,8}$]undecane fumarate A solution of the product of Example 3A (0.11 g, 0.35 mmol) in 10% methanol-ether (20 mL) was treated with a saturated solution of fumaric acid in 10% methanol-ether until a precipitate began to form. After stirring for an additional 20 minutes, the mixture was filtered and the solid was rinsed with ethyl acetate to afford the title compound: $^1$H NMR (300 MHz, CD$_3$OD) δ ppm 2.03 (d, J=14.9 Hz, 2 H), 2.26 (s, 2 H), 2.31 (s, 1 H), 2.47 (s, 2 H), 3.56-3.64 (m, 2 H), 3.68-3.75 (m, 4 H), 4.51 (s, 1 H), 6.75 (s, 3 H), 7.65 (d, J=4.7 Hz, 1 H), 8.10 (d, J=5.4 Hz, 1 H), 8.58 (s, 1 H), 9.24 (s, 1 H); MS (DCI/NH$_3$) m/z 314 (M+H)$^+$.

Example 4

4-(thieno[3,2-b]pyridin-5-ylcarbonyl)-1,4-diazatricyclo[4.3.1.1$^{3,8}$]undecane The product of Example 2 (0.13 g, 0.85 mmol) was stirred in tetrahydrofuran (10 mL) as thieno[3,2-b]pyridine-5-carboxylic acid (0.168 g, 0.94 mmol; U.S. Pat. No. 5,374,635) and 1-hydroxybenzotriazole (0.115 g, 0.85 mmol; Aldrich) were added. After stirring for 5 minutes, N,N'-dicyclohexylcarbodiimide (DCC; 0.194 g, 0.94 mmol; Aldrich) was added, and the reaction was stirred for 24 hours. The solvent was removed under vacuum, and the product was purified by preparative HPLC [Waters XTerra RP18 30×100 mm column, 5 µm, flow rate 40 mL/min, 5-50% gradient of acetonitrile in 0.1% aqueous trifluoroacetic acid] to afford the title compound as the corresponding trifluoroacetate: $^1$H NMR (300 MHz, CDCl$_3$) δ ppm 1.74 (s, 1 H), 1.92 (s, 2 H), 2.14 (d, J=3.1 Hz, 4 H), 3.09 (s, 1 H), 3.13 (s, 2 H), 3.19 (s, 2 H), 3.44 (d, J=13.6 Hz, 2 H), 4.44 (d, J=8.1 Hz, 1 H), 7.59 (d, J=5.4 Hz, 1 H), 7.85 (d, J=5.4 Hz, 1 H), 8.18-8.23 (m, J=8.5 Hz, 1 H), 8.30-8.36 (m, J=8.5 Hz, 1 H); MS (DCI/NH$_3$) m/z 314 (M+H)$^+$.

Example 5

4-(5,5-dioxidodibenzo[b,d]thien-3-yl)-1,4-diazatricyclo[4.3.1.1$^{3,8}$]undecane A catalyst solution was prepared by mixing tris(dibenzylideneacetone)dipalladium(0) (Pd$_2$(dba)$_3$; 12 mg, 0.013 mmol; Alfa) and racemic 2,2'-bis(diphenylphosphino)-1,1'-binaphthyl (BINAP; 16 mg, 0.026 mmol; Strem) in toluene (4 mL) and heating the mixture to 80° C. for 15 minutes. The solution was cooled, and then the product of Example 2 (100 mg, 0.66 mmol) and 3-bromodibenzothiophene-5,5-dioxide (640 mg, 3.2 mmol; J. Heterocycl. Chem. 1969, 6, 517) in toluene (5 mL) were added. Cesium carbonate (0.32 g, 0.98 mmol; Aldrich) was then added, and the reaction mixture was purged with nitrogen and heated to 80-85° C. for 16 hours. After cooling to room temperature, the mixture was filtered through diatomaceous earth, and the product was purified by preparative HPLC [Waters® XTerra RP18 30×100 mm column, 5 µm, flow rate 40 mL/min, 5-50% gradient of acetonitrile in 0.1% aqueous trifluoroacetic acid] to afford the title compound as the corresponding trifluoroacetate: $^1$H NMR (300 MHz, DMSO-d$_6$) δ ppm 1.93 (d, J=12.2 Hz, 1 H), 2.13-2.29 (m, 3 H), 2.37 (s, 3 H), 3.46 (d, J=13.2 Hz, 1 H), 3.56 (s, 2 H), 3.70 (s, 2 H), 3.79 (d, J=12.9 Hz, 2 H), 3.97 (m, 1 H), 6.95-7.17 (m, 2 H), 7.43 (t, J=8.0 Hz, 1 H), 7.64 (t, J=7.6 Hz, 1 H), 7.69-7.85 (m, 3 H); MS (DCI/NH$_3$) m/z 367 (M+H)$^+$.

Example 6

4-(5-phenyl-1,3,4-oxadiazol-2-yl)-1,4-diazatricyclo[4.3.1.1$^{3,8}$]undecane

Example 6A 2-(benzylthio)-5-phenyl-1,3,4-oxadiazole

A suspension of 5-phenyl-[1,3,4]oxadiazole-2-thiol (3.1 g, 17.4 mmol; Aldrich) in ethanol (30 mL) was cooled to 0° C. and treated with diisopropylethylamine (3.1 mL, 17.4 mmol; Aldrich). The suspension cleared. Benzyl bromide (2.08 mL, 17.4 mmol; Aldrich) was then added, and the mixture was allowed to warm to room temperature. After 45 minutes, the resulting precipitate was collected by filtration and dried to afford the title compound.

Example 6B 4-(5-phenyl-1,3,4-oxadiazol-2-yl)-1,4-diazatricyclo[4.3.1.1$^{3,8}$]undecane A solution of the product of Example 2 (0.25 g, 1.60 mmol), diisopropylethylamine (0.28 mL, 1.60 mmol; Aldrich), and the product of Example 6A (0.39 g, 1.45 mmol) in dichlorobenzene (4 mL) was heated to 220° C. under microwave irradiation for 30 minutes. After cooling, the reaction mixture was diluted with chloroform (10 mL), washed sequentially with saturated sodium bicarbonate, water, and brine, and dried (NaSO$_4$). The material was purified by flash chromatography on silica gel, eluting with 0-4% methanol (containing 1% ammonium hydroxide)-chloroform to afford the title compound: MS (DCI/NH$_3$) m/z 297 (M+H)$^+$.

Example 6C 4-(5-phenyl-1,3,4-oxadiazol-2-yl)-1,4-diazatricyclo[4.3.1.1$^{3,8}$]undecane 4-methylbenzenesulfonate A solution of the product of Example 6B (0.28, 0.94 mmol) in ethyl acetate (5 mL) was treated with a solution of p-toluenesulfonic acid monohydrate (0.18 g, 0.94 mmol; Aldrich) in ethyl acetate (3 mL). After stirring overnight, the resulting solid was collected by filtration, rinsed with ethyl acetate, and dried to afford the title compound: $^1$H NMR (300 MHz, CD$_3$OD) δ ppm 1.97 (dd, J=21.5, 13.7 Hz, 2 H), 2.28-2.44 (m, 6 H), 2.73 (s, 1 H), 3.42 (s, 2 H), 3.48-3.61 (m, 2 H), 3.72-4.01 (m, 4 H), 4.87 (t, J=4.6 Hz, 1 H), 7.22 (d, J=8.1 Hz, 2 H), 7.47-7.61 (m, 3 H), 7.70 (d, J=8.1 Hz, 2 H), 7.93 (dd, J=7.0, 2.9 Hz, 2 H); MS (DCI/NH$_3$) m/z 297 (M+H)$^+$.

Example 7

4-(6-phenylpyridazin-3-yl)-1,4-diazatricyclo[4.3.1.1$^{3,8}$]undecane

Example 7A 4-(6-phenylpyridazin-3-yl)-1,4-diazatricyclo[4.3.1.1$^{3,8}$]undecane A solution of the product of Example 2 (0.10 g, 0.66 mmol) in dry toluene (10 mL) was treated with 3-chloro-6-phenylpyridazine (0.20 g, 1.0 mmol; Aldrich), tris(dibenzylideneacetone)dipalladium(0) (Pd$_2$(dba)$_3$; 0.01 g, 0.013 mmol; Alfa Aesar), 1,3-bis(2,6-di-iso-propylphenyl)imidazolium chloride (0.017 g, 0.04 mmol; Strem), and sodium tert-butoxide (0.148 g, 1.32 mmol). The mixture was purged with nitrogen and heated to 90° C. for 8 hours. After cooling to room temperature, the reaction was quenched by pouring into a 5% aqueous NaHCO$_3$ solution. The mixture was extracted with chloroform (3×), washed with brine, dried (MgSO$_4$), filtered and concentrated. The crude product was purified by flash chromatography on silica gel, eluting with 2-10% methanol (containing 1% ammonium hydroxide)-chloroform to afford the title compound: MS (DCI/NH$_3$) m/z 307 (M+H)$^+$.

Example 7B 4-(6-phenylpyridazin-3-yl)-1,4-diazatricyclo[4.3.1.1$^{3,s}$]undecane 4-methylbenzenesulfonate A solution of the product of Example 7A (0.08 g, 0.26 mmol) in ethyl acetate (5 mL) was treated with a solution of p-toluenesulfonic acid monohydrate (0.055 g, 0.029 mmol; Aldrich) in ethyl acetate (3 mL). After stirring overnight, the resulting solid was collected by filtration, rinsed with ethyl acetate, and dried to afford the title compound: $^1$H NMR (300 MHz, CD$_3$OD) δ ppm 1.89 (s, 1 H), 1.94 (s, 1 H), 2.30-2.48 (m, 6 H), 2.71-2.81 (m, 1 H), 3.44 (s, 3 H), 3.46-3.55 (m, 2 H), 3.70-3.88 (m, 4 H), 5.75 (t, J=4.9 Hz, 1 H), 7.24 (t, J=9.3 Hz, 3 H), 7.39-7.53 (m, 3 H), 7.70 (d, J=8.1 Hz, 2 H), 7.88-7.98 (m, 3 H); MS (DCI/NH$_3$) m/z 307 (M+H)$^+$.

Example 8

4-[6-(1-benzothien-5-yl)pyridazin-3-yl]-1,4-diazatricyclo[4.3.1.1$^{3,8}$]undecane Example 8A 4-(6-chloropyridazin-3-yl)-1,4-diazatricyclo[4.3.1.1$^{3,8}$]undecane A solution of the product of Example 2 (0.30 g, 2.0 mmol) in dry toluene (10 mL) was treated with 3,6-dichloropyridazine (0.71 g, 4.8 mmol; Aldrich), tris(dibenzylideneacetone)dipalladium(0) (Pd$_2$(dba)$_3$; 0.037 g, 0.04 mmol; Alfa Aesar), 1,3-bis(2,6-di-1-propylphenyl)imidazolium chloride (0.057 g, 0.12 mmol; Strem), and sodium tert-butoxide (0.45 g, 4.0 mmol; Aldrich). The mixture was purged with nitrogen and heated to 90° C. for 8 hours. After cooling to room temperature, the reaction was quenched by pouring into a 5% aqueous NaHCO$_3$ solution. The mixture was extracted with chloroform (3×), washed with brine, dried (MgSO$_4$), filtered and concentrated. The crude product was purified by preparative HPLC [Waters 30×100 mm XBridge Prep C18, 5 μm, 40 mL/min, 5-95% gradient of acetonitrile in buffer (0.1 M aqueous ammonium bicarbonate, adjusted to pH 10 with ammonium hydroxide)] to afford the title compound: MS (DCI/NH$_3$) m/z 265 (M+H)$^+$.

Example 8B

4-[6-(1-benzothien-5-yl)pyridazin-3-yl]-1,4-diazatricyclo[4.3.1.1$^{3,8}$]undecane A microwave-safe vial was charged with the product from Example 8A (0.060 g, 0.23 mmol), 2-(benzo[b]thiophen-5-yl)-4,4,5,5-tetramethyl-1,3,2-dioxaborolane (0.0825 g, 0.32 mmol; Maybridge), dichlorobis(triphenylphosphine)palladium (0.016 g, 0.023 mmol; Aldrich), (2-biphenyl)dicyclohexylphosphine (0.0024 g, 0.0068 mmol; Aldrich), and 3 mL 1:1:1 ethanol-dioxane-1 M sodium carbonate solution. The mixture was stirred for 5 minutes at room temperature, then heated in a microwave reactor at 150° C. (300 W) for 10 minutes. The reaction was filtered, concentrated, and purified by flash chromatography on silica gel, eluting with 5-10% methanol (containing 1% ammonium hydroxide)-chloroform to afford the title compound: MS (DCI/NH$_3$) m/z 363 (M+H)$^+$.

Example 8C

4-[6-(1-benzothien-5-yl)pyridazin-3-yl]-1,4-diazatricyclo[4.3.1.1$^{3,8}$]undecane 4-methylbenzenesulfonate A solution of the product of Example 8B (0.060 g, 0.16 mmol) in ethyl acetate (5 mL) was treated with a solution of p-toluenesulfonic acid monohydrate (0.033 g, 0.175 mmol) in ethyl acetate (3 mL). After stirring for 2 hours, the resulting solid was collected by filtration, rinsed with ethyl acetate, and dried to afford the title compound: $^1$H NMR (300 MHz, CD$_3$OD) δ ppm 1.93 (d, J=12.9 Hz, 2 H), 2.31-2.51 (m, 7 H), 2.73-2.86 (m, 1 H), 3.40-3.63 (m, 4 H), 3.73-3.93 (m, 4 H), 5.61-5.77 (m, 1 H), 7.21 (d, J=7.8 Hz, 2 H), 7.38 (d, J=9.8 Hz, 1 H), 7.49 (d, J=5.4 Hz, 1 H), 7.63-7.74 (m, 3 H), 7.95 (s, 1 H), 8.06 (t, J=9.3 Hz, 2 H), 8.39 (s, 1 H); MS (DCI/NH$_3$) m/z 363 (M+H)$^+$.

Example 9

4-(3-methoxybenzoyl)-1,4-diazatricyclo[4.3.1.1$^{3,8}$]undecane

The title compound was prepared from the product of Example 2 and 3-methoxybenzoic acid according to General Method A: LC-MS Method C (ESI+) m/z 287.0 (M+H)$^+$, retention time 1.361 minutes.

Example 10

4-(1-naphthylacetyl)-1,4-diazatricyclo[4.3.1.1$^{3,8}$]undecane

The title compound was prepared from the product of Example 2 and 1-naphthylacetic acid according to General Method A: LC-MS Method D (ESI−) m/z 321.0 (M+H)$^+$, retention time 1.540 minutes.

Example 11

4-(pyridin-2-ylcarbonyl)-1,4-diazatricyclo[4.3.1.1$^{3,8}$]undecane

The title compound was prepared from the product of Example 2 and pyridin-2-ylcarboxylic acid according to General Method A: $^1$H NMR (500 MHz, DMSO-d$_6$) δ ppm 8.59 (s, 1 H), 7.95 (t, 1 H), 7.59 (m, 1 H), 7.49 (m, 1 H), 5.09-4.34 (m, 1 H), 3.78-3.11 (m, 8 H), 2.63-2.42 (m, 1 H), 2.18-2.03 (m, 3 H), 1.85-1.66 (m, 2 H); LC-MS Method B (ESI+) m/z 258.0 (M+H)$^+$, retention time 1.459 minutes.

Example 12

4-(phenoxyacetyl)-1,4-diazatricyclo[4.3.1.1$^{3,8}$]undecane

The title compound was prepared from the product of Example 2 and phenoxyacetic acid according to General Method A: LC-MS Method C (ESI+) m/z 287.0 (M+H)$^+$, retention time 1.415 minutes.

Example 13

4-(3-chlorobenzoyl)-1,4-diazatricyclo[4.3.1.1$^{3,8}$]undecane

The title compound was prepared from the product of Example 2 and 3-chlorobenzoic acid according to General Method A: LC-MS Method C (ESI+) m/z 291.0 (M+H)$^+$, retention time 1.448 minutes.

Example 14

N-[4-(1,4-diazatricyclo[4.3.1.1$^{3,8}$]undec-4-ylcarbonyl)phenyl]-N,N-dimethylamine The title compound was prepared from the product of Example 2 and 4-dimethylaminobenzoic acid according to General Method A: LC-MS Method C (ESI+) m/z 300.0 (M+H)$^+$, retention time 1.430 minutes.

Example 15

4-[(2-methylphenypacetyl]-1,4-diazatricyclo[4.3.1.1$^{3,8}$]undecane

The title compound was prepared from the product of Example 2 and (2-methylphenyl)acetic acid according to General Method A: $^1$H NMR (500 MHz, DMSO-d$_6$) δ ppm 10.31 (s, 1 H), 7.15-7.06 (m, 4 H), 5.15-3.46 (m, 7 H), 3.34-3.17 (m, 5 H), 2.66-1.98 (m, 5 H), 1.66-1.45 (m, 2 H); LC-MS Method C (ESI+) m/z 285.0 (M+H)$^+$, retention time 1.507 minutes.

Example 16

3-(1,4-diazatricyclo[4.3.1.1$^{3,8}$]undec-4-ylcarbonyl)benzonitrile

The title compound was prepared from the product of Example 2 and 3-cyanobenzoic acid according to General Method A: LC-MS Method D (ESI+) m/z 282.0 (M+H)$^+$, retention time 1.344 minutes.

Example 17

4-(2-methylbenzoyl)-1,4-diazatricyclo[4.3.1.1$^{3,8}$]undecane

The title compound was prepared from the product of Example 2 and 2-methylbenzoic acid according to General Method A: LC-MS Method C (ESI+) m/z 271.0 (M+H)$^+$, retention time 1.419 minutes.

Example 18

N-[4-(1,4-diazatricyclo[4.3.1.1$^{3,8}$]undec-4-ylcarbonyl)phenyl]acetamide

The title compound was prepared from the product of Example 2 and 4-acetamidobenzoic acid according to General Method A: $^1$H NMR (500 MHz, CDCl$_3$) δ ppm 8.09 (d, 1 H), 7.46-7.43 (m, 2 H), 7.33-7.31 (m, 1 H), 7.27-7.22 (m, 1 H), 4.86-3.72 (m, 2 H), 3.68-3.24 (m, 2 H), 3.18-2.81 (m, 4 H), 2.31-2.17 (m, 5 H), 2.15-1.87 (m, 2H), 1.85-1.62 (m, 3 H); LC-MS Method D (ESI+) m/z 314.0 (M+H)$^+$, retention time 1.059 minutes.

Example 19

4-[(3-methylphenyl)acetyl]-1,4-diazatricyclo[4.3.1.1$^{3,8}$]undecane

The title compound was prepared from the product of Example 2 and 3-methylphenylacetic acid according to General Method A: LC-MS Method B (ESI+) m/z 285.0 (M+H)$^+$, retention time 1.670 minutes.

Example 20

4-(2,5-dimethylbenzoyl)-1,4-diazatricyclo[4.3.1.1$^{3,8}$]undecane

The title compound was prepared from the product of Example 2 and 2,5-dimethylbenzoic acid according to General Method A: $^1$H NMR (500 MHz, CDCl$_3$) δ ppm 7.07-6.99 (m, 3 H), 5.10-3.79 (m, 2 H), 3.49-3.01 (m, 3 H), 3.00-2.76 (m, 4 H), 2.34-2.22 (m, 8 H), 2.20-1.80 (m, 4 H); LC-MS Method A (ESI+) m/z 285.0 (M+H)$^+$, retention time 1.145 minutes.

Example 21

4-(3-phenylpropanoyl)-1,4-diazatricyclo[4.3.1.1$^{3,8}$]undecane

The title compound was prepared from the product of Example 2 and 3-phenylpropanoic acid according to General Method A: LC-MS Method D (ESI+) m/z 285.0 (M+H)$^+$, retention time 1.431 minutes.

Example 22

N-[3-(1,4-diazatricyclo[4.3.1.1$^{3,8}$]undec-4-ylcarbonyl)phenyl]acetamide

The title compound was prepared from the product of Example 2 and 3-acetamidobenzoic acid according to General Method A: $^1$H NMR (500 MHz, CDCl$_3$) δ ppm 7.95 (d, 1 H), 7.55-7.43 (m, 2 H), 7.32-7.31 (m, 1 H), 7.03-7.01 (m, 1 H), 4.82-3.79 (m, 2 H), 3.41-2.75 (m, 6 H), 2.67-1.80 (m, 6 H), 1.80-1.52 (m, 4 H); LC-MS Method C (ESI+) m/z 314.0 (M+H)$^+$, retention time 1.283 minutes.

Example 23

4-(4-ethylbenzoyl)-1,4-diazatricyclo[4.3.1.1$^{3,8}$]undecane

The title compound was prepared from the product of Example 2 and 4-ethylbenzoic acid according to General Method A: $^1$H NMR (500 MHz, CDCl$_3$) δ ppm 7.28-7.14 (m, 4H), 4.81-3.14 (m, 5 H), 2.92-2.58 (m, 6 H), 2.16-2.12 (m, 3 H), 1.75-1.70 (m, 3 H), 1.17 (t, 3 H); LC-MS Method A (ESI+) m/z 285.0 (M+H)$^+$, retention time 1.172 minutes.

Example 24

4-{[2-(trifluoromethyl)phenyl]acetyl}-1,4-diazatricyclo[4.3.1.1$^{3,8}$]undecane The title compound was prepared from the product of Example 2 and (2-trifluoromethylphenyl)acetic acid according to General Method A: LC-MS Method C (ESI+) m/z 339.0 (M+H)$^+$, retention time 1.590 minutes.

Example 25

4-(2,4-dimethylbenzoyl)-1,4-diazatricyclo[4.3.1.1$^{3,8}$]undecane

The title compound was prepared from the product of Example 2 and 2,4-dimethylbenzoic acid according to General Method A: $^1$H NMR (500 MHz, CDCl$_3$) δ ppm 7.06-6.99 (m, 3 H), 5.10-3.67 (m, 2 H), 3.37-3.05 (m, 3 H), 3.04-2.81 (m, 4 H), 2.32-2.19 (m, 7 H), 1.81-1.67 (m, 5 H); LC-MS Method C (ESI+) m/z 285.0 (M+H)$^+$, retention time 1.528 minutes.

Example 26

4-(3-phenylbutanoyl)-1,4-diazatricyclo[4.3.1.1$^{3,8}$]undecane

The title compound was prepared from the product of Example 2 and 3-phenylbutanoic acid according to General Method D (ESI+) m/z 299.0 (M+H)$^+$, retention time 1.494 minutes.

Example 27

4-(1,2,3,4-tetrahydronaphthalen-2-ylcarbonyl)-1,4-diazatricyclo[4.3.1.1$^{3,8}$]undecane The title compound was prepared from the product of Example 2 and 1,2,3,4-tetrahydronaphthalen-2-ylcarboxylic acid according to General Method A: LC-MS Method D (ESI+) m/z 311.0 (M+H)$^+$, retention time 1.557 minutes.

Example 28

4-(4-ethoxybenzoyl)-1,4-diazatricyclo[4.3.1.1$^{3,8}$]undecane

The title compound was prepared from the product of Example 2 and 4-ethoxybenzoic acid according to General Method A: LC-MS Method D (ESI+) m/z 301.0 (M+H)$^+$, retention time 1.406 minutes.

Example 29

N-{4-[2-(1,4-diazatricyclo[4.3.1.1$^{3,8}$]undec-4-yl)-2-oxoethyl]phenyl}-N,N-dimethylamine The title compound was prepared from the product of Example 2 and (4-dimethylaminophenyl)acetic acid according to General Method A: LC-MS Method A (ESI+) m/z 314.0 (M+H)$^+$, retention time 0.861 minutes.

Example 30

4-(2,3-difluorobenzoyl)-1,4-diazatricyclo[4.3.1.1$^{3,8}$]undecane

The title compound was prepared from the product of Example 2 and 2,3-difluorobenzoic acid according to General Method A: LC-MS Method D (ESI+) m/z 293.0 (M+H)$^+$, retention time 1.326 minutes.

Example 31

4-(3-methylbenzoyl)-1,4-diazatricyclo[4.3.1.1$^{3,8}$]undecane

The title compound was prepared from the product of Example 2 and 3-methylbenzoic acid according to General Method A: LC-MS Method D (ESI+) m/z 271.0 (M+H)$^+$, retention time 1.355 minutes.

Example 32

4-(2,5-dimethyl-3-furoyl)-1,4-diazatricyclo[4.3.1.1$^{3,8}$]undecane

The title compound was prepared from the product of Example 2 and 2,5-dimethyl-3-furoic acid according to General Method A: LC-MS Method D (ESI+) m/z 289.0 (M+H)$^+$, retention time 1.362 minutes.

Example 33

4-(pyridin-3-ylcarbonyl)-1,4-diazatricyclo[4.3.1.1$^{3,8}$]undecane

The title compound was prepared from the product of Example 2 and pyridine-3-carboxylic acid according to General Method A: LC-MS Method B (ESI+) m/z 258.0 (M+H)$^+$, retention time 1.330 minutes.

Example 34

4-(5-chloro-2-fluorobenzoyl)-1,4-diazatricyclo[4.3.1.1$^{3,8}$]undecane

The title compound was prepared from the product of Example 2 and 5-chloro-2-fluorobenzoic acid according to General Method A: LC-MS Method D (ESI+) m/z 309.0 (M+H)$^+$, retention time 1.397 minutes.

Example 35

4-(3-methyl-2-furoyl)-1,4-diazatricyclo[4.3.1.1$^{3,8}$]undecane

The title compound was prepared from the product of Example 2 and 3-methyl-2-furoic acid according to General Method A: LC-MS Method D (ESI+) m/z 261.0 (M+H)$^+$, retention time 1.274 minutes.

Example 36

4-[(1-phenyl-1H-pyrazol-5-yl)carbonyl]-1,4-diazatricyclo[4.3.1.1$^{3,8}$]undecane The title compound was prepared from the product of Example 2 and (1-phenyl-1H-pyrazol-5-yl)carboxylic acid according to General Method A: LC-MS Method D (ESI+) m/z 323.0 (M+H)$^+$, retention time 1.307 minutes.

Example 37

4-(1H-indol-5-ylcarbonyl)-1,4-diazatricyclo[4.3.1.1$^{3,8}$]undecane

The title compound was prepared from the product of Example 2 and 1H-indol-5-ylcarboxylic acid according to General Method A: LC-MS Method D (ESI+) m/z 296.0 (M+H)$^+$, retention time 1.243 minutes.

Example 38

4-(3,5-dimethoxybenzoyl)-1,4-diazatricyclo[4.3.1.1$^{3,8}$]undecane

The title compound was prepared from the product of Example 2 and 3,5-dimethoxybenzoic acid according to General Method A: LC-MS Method D (ESI+) m/z 317.0 (M+H)$^+$, retention time 1.356 minutes.

Example 39

4-[(4-methylthien-2-yl)carbonyl]-1,4-diazatricyclo[4.3.1.1$^{3,8}$]undecane

The title compound was prepared from the product of Example 2 and 4-methylthien-2-ylcarboxylic acid according to General Method A: $^1$H NMR (500 MHz, CDCl$_3$) δ ppm 7.20-6.99 (m, 2 H), 4.82-4.47 (d, 1 H), 3.91-3.78 (m, 2 H), 3.34-3.25 (m, 2 H), 3.08-2.85 (m, 4 H), 2.26-2.11 (m, 6 H), 1.87-1.65 (m, 3 H); LC-MS Method D (ESI+) m/z 277.0 (M+H)$^+$, retention time 1.338 minutes.

Example 40

4-[(2,5-dimethoxyphenyl)acetyl]-1,4-diazatricyclo[4.3.1.1$^{3,8}$]undecane

The title compound was prepared from the product of Example 2 and (2,5-dimethoxyphenyl)acetic acid according to General Method A: LC-MS Method D (ESI+) m/z 331.0 (M+H)$^+$, retention time 1.391 minutes.

Example 41

4-[(5-methylthien-2-yl)carbonyl]-1,4-diazatricyclo[4.3.1.1$^{3,8}$]undecane

The title compound was prepared from the product of Example 2 and 5-methylthien-2-ylcarboxylic acid according to General Method A: LC-MS Method D (ESI+) m/z 277.0 (M+H)$^+$, retention time 1.340 minutes.

Example 42

4-(2-fluorobenzoyl)-1,4-diazatricyclo[4.3.1.1$^{3,8}$]undecane

The title compound was prepared from the product of Example 2 and 2-fluorobenzoic acid according to General Method A: LC-MS Method D (ESI+) m/z 275.0 (M+H)$^+$, retention time 1.249 minutes.

Example 43

4-[(2-fluorophenyl)acetyl]-1,4-diazatricyclo[4.3.1.1$^{3,8}$]undecane

The title compound was prepared from the product of Example 2 and (2-fluorophenyl)acetic acid according to General Method A: LC-MS Method D (ESI+) m/z 289.0 (M+H)$^+$, retention time 1.362 minutes.

Example 44

4-[4-(trifluoromethyl)benzoyl]-1,4-diazatricyclo[4.3.1.1$^{3,8}$]undecane

The title compound was prepared from the product of Example 2 and 4-trifluoromethylbenzoic acid according to General Method A: $^1$H NMR (500 MHz, CDCl$_3$) δ ppm 7.66 (d, 2 H), 7.52-7.44 (dd, 2 H), 4.90-3.82 (m, 2 H), 3.48-3.14 (m, 2 H), 3.00-2.82 (m, 4 H), 2.32-2.20 (m, 3 H), 1.80-1.17 (m, 4 H); LC-MS Method B (ESI+) m/z 325.0 (M+H)$^+$, retention time 1.711 minutes.

Example 45

4-(3,4-difluorobenzoyl)-1,4-diazatricyclo[4.3.1.1$^{3,8}$]undecane

The title compound was prepared from the product of Example 2 and 3,4-difluorobenzoic acid according to General Method A: $^1$H NMR (500 MHz, DMSO-d$_6$) δ ppm 10.27 (s, 1 H), 7.61-7.26 (m, 3 H), 4.99-3.101 (m, 10 H), 2.51-1.99 (m, 4 H), 1.82-1.62 (m, 2 H); LC-MS Method D (ESI+) m/z 293.0 (M+H)$^+$, retention time 1.343 minutes.

Example 46

4-(thien-2-ylcarbonyl)-1,4-diazatricyclo[4.3.1.1$^{3,8}$]undecane

The title compound was prepared from the product of Example 2 and 2-thienylcarboxylic acid according to General Method A: $^1$H NMR (500 MHz, DMSO-d$_6$) δ ppm 10.17 (s, 1 H), 7.80 (s, 1 H), 7.59-7.22 (m, 2 H), 5.00-3.22 (m, 11 H), 2.56 (s, 1 H), 2.23-2.20 (m, 3 H), 2.00-1.77 (m, 2 H); LC-MS Method D (ESI+) m/z 263.0 (M+H)+, retention time 1.204 minutes.

Example 47

4-[(5-methylpyrazin-2-yl)carbonyl]-1,4-diazatricyclo[4.3.1.1$^{3,8}$]undecane

The title compound was prepared from the product of Example 2 and 5-methylpyrazin-2-ylcarboxylic acid according to General Method A: LC-MS Method D (ESI+) m/z 273.0 (M+H)+, retention time 1.040 minutes.

Example 48

4-(2,3-dimethylbenzoyl)-1,4-diazatricyclo[4.3.1.1$^{3,8}$]undecane

The title compound was prepared from the product of Example 2 and 2,3-dimethylbenzoic acid according to General Method A: $^1$H NMR (500 MHz, DMSO-d$_6$) δ ppm 10.23 (s, 1 H), 7.20-7.14 (m, 2 H), 7.06-7.03 (m, 1 H), 5.19-2.38 (m, 9 H), 2.26-1.82 (m, 9 H), 1.77-1.49 (m, 2 H); LC-MS Method D (ESI+) m/z 285.0 (M+H)+, retention time 1.403 minutes.

Example 49

4-(quinolin-2-ylcarbonyl)-1,4-diazatricyclo[4.3.1.1$^{3,8}$]undecane

The title compound was prepared from the product of Example 2 and quinoline-2-carboxylic acid according to General Method A: LC-MS Method D (ESI+) m/z 308.0 (M+H)+, retention time 1.351 minutes.

Example 50

4-(thien-2-ylacetyl)-1,4-diazatricyclo[4.3.1.1$^{3,8}$]undecane

The title compound was prepared from the product of Example 2 and thien-2-ylacetic acid according to General Method A: $^1$H NMR (500 MHz, CDCl$_3$) δ ppm 7.21-7.19 (m, 1H), 6.96-6.88 (m, 2 H), 4.99-4.31 (m, 1 H), 3.95-3.93 (m, 2 H), 3.69-3.66 (m, 2 H), 3.29-3.25 (m, 2 H), 2.92-2.83 (m, 4 H), 2.17-2.11 (m, 3 H), 1.66-1.60 (m, 3 H); LC-MS Method D (ESI+) m/z 277.0 (M+H)+, retention time 1.281 minutes.

Example 51

4-[(3-methoxyphenyl)acetyl]-1,4-diazatricyclo[4.3.1.1$^{3,8}$]undecane

The title compound was prepared from the product of Example 2 and (3-methoxyphenyl)acetic acid according to General Method A: LC-MS Method D (ESI+) m/z 301.0 (M+H)+, retention time 1.370 minutes.

Example 52

4-[(1-methyl-1H-pyrrol-2-yl)carbonyl]-1,4-diazatricyclo[4.3.1.1$^{3,8}$]undecane The title compound was prepared from the product of Example 2 and 1-methyl-1H-pyrrol-2-ylcarboxylic acid according to General Method A: LC-MS Method D (ESI+) m/z 260.0 (M+H)+, retention time 1.228 minutes.

Example 53

2-(1,4-diazatricyclo[4.3.1.1$^{3,8}$]undec-4-ylcarbonyl)phenol

The title compound was prepared from the product of Example 2 and 2-hydroxybenzoic acid according to General Method A: LC-MS Method D (ESI+) m/z 273.0 (M+H)+, retention time 1.153 minutes.

Example 54

4-[(2-methoxypyridin-3-yl)carbonyl]-1,4-diazatricyclo[4.3.1.1$^{3,8}$]undecane

The title compound was prepared from the product of Example 2 and 2-methoxynicotinic acid according to General Method A: LC-MS Method D (ESI+) m/z 288.0 (M+H)+, retention time 1.135 minutes.

Example 55

4-(1H-pyrrol-2-ylcarbonyl)-1,4-diazatricyclo[4.3.1.1$^{3,8}$]undecane

The title compound was prepared from the product of Example 2 and 1H-pyrrol-2-ylcarboxylic acid according to General Method A: LC-MS Method D (ESI+) m/z 245.0 (M+H)+, retention time 1.16 minutes.

Example 56

4-(3-chloro-4-fluorobenzoyl)-1,4-diazatricyclo[4.3.1.1$^{3,8}$]undecane

The title compound was prepared from the product of Example 2 and 3-chloro-4-fluorobenzoic acid according to General Method A: LC-MS Method D (ESI+) m/z 309.0 (M+H)+, retention time 1.435 minutes.

Example 57

4-(1H-indazol-3-ylcarbonyl)-1,4-diazatricyclo[4.3.1.1$^{3,8}$]undecane

The title compound was prepared from the product of Example 2 and 1H-indazol-3-ylcarboxylic acid according to General Method A: $^1$H NMR (500 MHz, CDCl$_3$) δ ppm 12.01 (br, 1 H), 0.91 (d, 1 H), 7.45 (d, 1 H), 7.38 (d, 1 H), 7.22 (d, 1 H), 5.06-4.92 (m, 1 H), 4.04-3.82 (m, 2 H), 3.46-2.88 (m, 6 H), 2.28-1.70 (m, 6 H); LC-MS Method D (ESI+) m/z 296.0 (M+H)+, retention time 1.314 minutes.

Example 58

4-(5-chloro-2-methoxybenzoyl)-1,4-diazatricyclo[4.3.1.1$^{3,8}$]undecane

The title compound was prepared from the product of Example 2 and 5-chloro-2-methoxybenzoic acid according to General Method A: LC-MS Method D (ESI+) m/z 321.0 (M+H)+, retention time 1.417 minutes.

Example 59

4-(2,4-difluorobenzoyl)-1,4-diazatricyclo[4.3.1.1$^{3,8}$]undecane

The title compound was prepared from the product of Example 2 and 2,4-difluorobenzoic acid according to General Method A: LC-MS Method D (ESI+) m/z 293.0 (M+H)$^+$, retention time 1.314 minutes.

Example 60

4-(thien-3-ylacetyl)-1,4-diazatricyclo[4.3.1.1$^{3,8}$]undecane

The title compound was prepared from the product of Example 2 and thien-3-ylacetic acid according to General Method A: LC-MS Method D (ESI+) m/z 277.0 (M+H)$^+$, retention time 1.278 minutes.

Example 61

4-(4-fluoro-3-methylbenzoyl)-1,4-diazatricyclo[4.3.1.1$^{3,8}$]undecane

The title compound was prepared from the product of Example 2 and 4-fluoro-3-methylbenzoic acid according to General Method A: LC-MS Method D (ESI+) m/z 289.0 (M+H)$^+$, retention time 1.405 minutes.

Example 62

4-(2-furoyl)-1,4-diazatricyclo[4.3.1.1$^{3,8}$]undecane

The title compound was prepared from the product of Example 2 and 2-furoic acid according to General Method A: LC-MS Method D (ESI+) m/z 247.0 (M+H)$^+$, retention time 1.081 minutes.

Example 63

4-benzoyl-1,4-diazatricyclo[4.3.1.1$^{3,8}$]undecane

The title compound was prepared from the product of Example 2 and benzoic acid according to General Method A: $^1$H NMR (500 MHz, DMSO-d$_6$) δ ppm 10.24 (s, 1 H), 7.46-7.36 (m, 5 H), 5.03-4.18 (m, 1 H), 3.78-3.06 (m, 10 H), 2.62-2.42 (m, 1 H), 2.20-2.01 (m, 3 H), 1.81-1.61 (m, 2 H); LC-MS Method C (ESI+) m/z 257.0 (M+H)$^+$, retention time 1.299 minutes.

Example 64

4-(2-methoxybenzoyl)-1,4-diazatricyclo[4.3.1.1$^{3,8}$]undecane

The title compound was prepared from the product of Example 2 and 2-methoxybenzoic acid according to General Method A: LC-MS Method C (ESI+) m/z 287.0 (M+H)$^+$, retention time 1.406 minutes.

Example 65

4-[5-(3-fluoro-4-methoxyphenyl)pyridin-3-yl]-1,4-diazatricyclo[4.3.1.1$^{3,8}$]undecane

Example 65A 4-(5-Bromopyridin-3-yl)-1,4-diazatricyclo[4.3.1.1$^{3,8}$]undecane To a solution of the product of Example 2 (2 g, 13.1 mmol) in toluene (50 mL) under a nitrogen atmosphere was added 3,5-dibromopyridine (6.15 g, 26.3 mmol), sodium tert-butoxide (2.5 g, 26.0 mmol), 2,2'-bis(diphenylphosphino)-1,1'-binaphthyl (1.65 g, 26.4 mmol) and tris(dibenzylideneacetone)dipalladium(0) (1.2 g, 20.8 mmol). The mixture was stirred at reflux overnight. After cooling, the reaction mixture was concentrated under reduced pressure. The residue was purified by chromatography on silica gel (chloroform/methanol=20/1) to afford the title compound: $^1$H NMR (500 MHz, CDCl$_3$): δ ppm 7.42-7.31 (m, 3H), 3.23-3.05 (m, 5H), 2.83-2.72 (m, 4H), 2.08-1.92 (m, 4H), 1.58-1.56 (m, 3H).

Example 65B

4-[5-(3-fluoro-4-methoxyphenyl)pyridin-3-yl]-1,4-diazatricyclo[4.3.1.1$^{3,8}$]undecane The title compound was prepared from the product of Example 65A and 3-fluoro-4-methoxyphenylboronic acid according to General Method B: LC-MS Method B (ESI+) m/z 354.0 (M+H)$^+$, retention time 1.80 minutes.

Example 66

4-[5-(2,3-dihydro-1,4-benzodioxin-6-yl)pyridin-3-yl]-1,4-diazatricyclo[4.3.1.1$^{3,8}$]undecane The title compound was prepared from the product of Example 65A and (2,3-dihydro-1,4-benzodioxin-6-yl)boronic acid according to General Method B: LC-MS Method D (ESI+) m/z 364.0 (M+H)$^+$, retention time 1.30 minutes.

Example 67

N-{4-[5-(1,4-diazatricyclo[4.3.1.1$^{3,8}$]undec-4-yl)pyridin-3-yl]phenyl}-N,N-dimethylamine The title compound was prepared from the product of Example 65A and 4-dimethylaminophenylboronic acid according to General Method B: $^1$H NMR (500 MHz, CDCl$_3$) δ ppm 8.15 (s, 1 H), 8.03 (s, 1 H), 7.48 (d, 2 H), 7.06 (s, 1 H), 6.80 (d, 2 H), 3.73-3.35 (m, 7 H), 3.06-3.03 (m, 8 H), 2.27-2.17 (m, 3 H), 2.04-1.79 (m, 3 H), 1.88-1.77 (m, 3 H); LC-MS Method D (ESI+) m/z 349.0 (M+H)$^+$, retention time 1.24 minutes.

Example 68

4-[5-(3,4,5-trimethoxyphenyl)pyridin-3-yl]-1,4-diazatricyclo[4.3.1.1$^{3,8}$]undecane The title compound was prepared from the product of Example 65A and 3,4,5-trimethoxyphenylboronic acid according to General Method B: $^1$H NMR (500 MHz, CDCl$_3$) δ ppm 8.16 (s, 2 H), 7.03 (s, 1 H), 6.73 (s, 2 H), 4.1 (s, 1 H), 3.91 (s, 9H.), 3.73-3.37 (m, 5 H), 3.05-3.00 (m, 4 H), 2.27-2.17 (m, 5 H); LC-MS Method D (ESI+) m/z 396.0 (M+H)+, retention time 1.32 minutes.

Example 69

4-[5-(3,5-dimethylisoxazol-4-yl)pyridin-3-yl]-1,4-diazatricyclo[4.3.1.1$^{3,8}$]undecane The title compound was prepared from the product of Example 65A and 3,5-dimethylisoxazol-4-ylboronic acid according to General Method B: LC-MS Method B (ESI+) m/z 325.0 (M+H)+, retention time 1.61 minutes.

Example 70

4-[5-(2,6-dimethoxyphenyl)pyridin-3-yl]-1,4-diazatricyclo[4.3.1.1$^{3,8}$]undecane The title compound was prepared from the product of Example 65A and 2,6-dimethoxyphenylboronic acid according to General Method B: LC-MS Method D (ESI+) m/z 366.0 (M+H)+, retention time 1.34 minutes.

Example 71

4-(5-phenylpyridin-3-yl)-1,4-diazatricyclo[4.3.1.1$^{3,8}$]undecane

The title compound was prepared from the product of Example 65A and phenylboronic acid according to General Method B: $^1$H NMR (500 MHz, CDCl$_3$) δ ppm 6 ppm 8.14 (d, 2 H), 7.56 (d, 2 H), 7.46 (t, 2 H), 7.39 (t, 1 H), 7.10 (s, 1 H), 3.73-3.37 (m, 5 H), 3.05-2.97 (m, 3 H), 2.27-2.17 (m, 4 H), 1.88-1.77 (m, 3 H); LC-MS Method D (ESI+) m/z 306.0 (M+H)+, retention time 1.28 minutes.

Example 72

4-[5-(4-methylphenyl)pyridin-3-yl]-1,4-diazatricyclo[4.3.1.1$^{3,8}$]undecane

The title compound was prepared from the product of Example 65A and 4-methylphenylboronic acid according to General Method B: LC-MS Method D (ESI+) m/z 320.0 (M+H)+, retention time 1.37 minutes.

Example 73

4-[5-(4-fluorophenyl)pyridin-3-yl]-1,4-diazatricyclo[4.3.1.1$^{3,8}$]undecane

The title compound was prepared from the product of Example 65A and 4-fluorophenylboronic acid according to General Method B: LC-MS Method D (ESI+) m/z 324.0 (M+H)+, retention time 1.31 minutes.

Example 74

4-[5-(4-methoxyphenyl)pyridin-3-yl]-1,4-diazatricyclo[4.3.1.1$^{3,8}$]undecane

The title compound was prepared from the product of Example 65A and 4-methoxyphenylboronic acid according to General Method B: LC-MS Method D (ESI+) m/z 336.0 (M+H)+, retention time 1.32 minutes.

Example 75

4-{5-[4-(trifluoromethyl)phenyl]pyridin-3-yl}-1,4-diazatricyclo[4.3.1.1$^{3,8}$]undecane The title compound was prepared from the product of Example 65A and 4-trifluoromethylphenylboronic acid according to General Method B: LC-MS Method D (ESI+) m/z 374.0 (M+H)+, retention time 1.47 minutes.

Example 76

4-[5-(3-methylphenyl)pyridin-3-yl]-1,4-diazatricyclo[4.3.1.1$^{3,8}$]undecane

The title compound was prepared from the product of Example 65A and 3-methylphenylboronic acid according to General Method B: LC-MS Method D (ESI+) m/z 320.0 (M+H)+, retention time 1.37 minutes.

Example 77

4-[5-(3-fluorophenyl)pyridin-3-yl]-1,4-diazatricyclo[4.3.1.1$^{3,8}$]undecane

The title compound was prepared from the product of Example 65A and 3-fluorophenylboronic acid according to General Method B: LC-MS Method D (ESI+) m/z 324.0 (M+H)+, retention time 1.31 minutes.

Example 78

4-[5-(3-methoxyphenyl)pyridin-3-yl]-1,4-diazatricyclo[4.3.1.1$^{3,8}$]undecane

The title compound was prepared from the product of Example 65A and 3-methoxyphenylboronic acid according to General Method B: LC-MS Method D (ESI+) m/z 336.0 (M+H)+, retention time 1.32 minutes.

Example 79

4-[5-(2-furyl)pyridin-3-yl]-1,4-diazatricyclo[4.3.1.1$^{3,8}$]undecane

The title compound was prepared from the product of Example 65A and 2-furylboronic acid according to General Method B: LC-MS Method B (ESI+) m/z 296.0 (M+H)+, retention time 1.72 minutes.

Example 80

4-(5-thien-3-ylpyridin-3-yl)-1,4-diazatricyclo[4.3.1.1$^{3,8}$]undecane

The title compound was prepared from the product of Example 65A and thien-3-ylboronic acid according to General Method B: LC-MS Method D (ESI+) m/z 312.0 (M+H)+, retention time 1.25 minutes.

Example 81

4-[5-(3,4-dimethoxyphenyl)pyridin-3-yl]-1,4-diazatricyclo[4.3.1.1$^{3,8}$]undecane The title compound was prepared from the product of Example 65A and 3,4-dimethoxyphenylboronic acid according to General Method B: $^1$H NMR (500 MHz, CDCl$_3$) δ ppm 8.14 (d, 2 H), 7.19 (d, 1 H), 7.07 (d, 2 H), 6.93 (d, 1 H), 4.13 (s, 1 H), 3.91 (s, 3 H), 3.87 (s, 3 H), 3.81-3.30 (m, 7 H), 3.09-2.95 (m, 4 H), 2.34-2.18 (m, 3 H); LC-MS Method D (ESI+) m/z 366.0 (M+H)$^+$, retention time 1.28 minutes.

Example 82

4-(3,3'-bipyridin-5-yl)-1,4-diazatricyclo[4.3.1.1$^{3,8}$]undecane

The title compound was prepared from the product of Example 65A and 3-pyridinylboronic acid according to General Method B: LC-MS Method B (ESI+) m/z 307.0 (M+H)$^+$, retention time 1.54 minutes.

Example 83

4-(3,4'-bipyridin-5-yl)-1,4-diazatricyclo[4.3.1.1$^{3,8}$]undecane

The title compound was prepared from the product of Example 65A and 4-pyridinylboronic acid according to General Method B: LC-MS Method B (ESI+) m/z 307.0 (M+H)$^+$, retention time 1.54 minutes.

Example 84

4-[5-(2-methoxyphenyl)pyridin-3-yl]-1,4-diazatricyclo[4.3.1.1$^{3,8}$]undecane

The title compound was prepared from the product of Example 65A and 2-methoxyphenylboronic acid according to General Method B: LC-MS Method D (ESI+) m/z 336.0 (M+H)$^+$, retention time 1.30 minutes.

Example 85

4-[5-(2,5-dimethoxyphenyl)pyridin-3-yl]-1,4-diazatricyclo[4.3.1.1$^{3,8}$]undecane The title compound was prepared from the product of Example 65A and 2,5-dimethoxyphenylboronic acid according to General Method B: LC-MS Method D (ESI+) m/z 366.0 (M+H)$^+$, retention time 1.36 minutes.

Example 86

4-[5-(2,4-dimethoxyphenyl)pyridin-3-yl]-1,4-diazatricyclo[4.3.1.1$^{3,8}$]undecane The title compound was prepared from the product of Example 65A and 2,4-dimethoxyphenylboronic acid according to General Method B: LC-MS Method D (ESI+) m/z 366.0 (M+H)$^+$, retention time 1.37 minutes.

Example 87

4-[5-(2-fluorophenyl)pyridin-3-yl]-1,4-diazatricyclo[4.3.1.1$^{3,8}$]undecane

The title compound was prepared from the product of Example 65A and 2-fluorophenylboronic acid according to General Method B: LC-MS Method D (ESI+) m/z 324.0 (M+H)$^+$, retention time 1.30 minutes.

Example 88

4-[5-(2-ethoxyphenyl)pyridin-3-yl]-1,4-diazatricyclo[4.3.1.1$^{3,8}$]undecane

The title compound was prepared from the product of Example 65A and 2-ethoxyphenylboronic acid according to General Method B: LC-MS Method D (ESI+) m/z 350.0 (M+H)$^+$, retention time 1.40 minutes.

Example 89

4-[5-(1,4-diazatricyclo[4.3.1.1$^{3,8}$]undec-4-yl)pyridin-3-yl]benzonitrile

The title compound was prepared from the product of Example 65A and 4-cyanophenylboronic acid according to General Method B: LC-MS Method D (ESI+) m/z 331.0 (M+H)$^+$, retention time 1.26 minutes.

Example 90

3-[5-(1,4-diazatricyclo[4.3.1.1$^{3,8}$]undec-4-yl)pyridin-3-yl]benzonitrile

The title compound was prepared from the product of Example 65A and 3-cyanophenylboronic acid according to General Method B: LC-MS Method D (ESI+) m/z 331.0 (M+H)$^+$, retention time 1.27 minutes.

Example 91

4-{5-[3-(trifluoromethyl)phenyl]pyridin-3-yl}-1,4-diazatricyclo[4.3.1.1$^{3,8}$]undecane The title compound was prepared from the product of Example 65A and 3-trifluorophenylboronic acid according to General Method B: LC-MS Method D (ESI+) m/z 374.0 (M+H)$^+$, retention time 1.46 minutes.

Example 92

4-[5-(1,3-benzodioxol-5-yl)pyridin-3-yl]-1,4-diazatricyclo[4.3.1.1$^{3,8}$]undecane The title compound was prepared from the product of Example 65A and 1,3-benzodioxol-5-ylboronic acid according to General Method B: LC-MS Method D (ESI+) m/z 350.0 (M+H)$^+$, retention time 1.37 minutes.

Example 93

4-(2'-methoxy-3,3'-bipyridin-5-yl)-1,4-diazatricyclo[4.3.1.1$^{3,8}$]undecane

The title compound was prepared from the product of Example 65A and 2-methoxypyridin-3-ylboronic acid according to General Method B: LC-MS Method D (ESI+) m/z 337.0 (M+H)$^+$, retention time 1.24 minutes.

Example 94

N-{3-[5-(1,4-diazatricyclo[4.3.1.1$^{3,8}$]undec-4-yl)pyridin-3-yl]phenyl}acetamide The title compound was prepared from the product of Example 65A and 3-acetamidophenylboronic acid according

Example 95

4-[5-(3,5-difluorophenyl)pyridin-3-yl]-1,4-diazatricyclo[4.3.1.1$^{3,8}$]undecane The title compound was prepared from the product of Example 65A and 3,5-difluorophenylboronic acid according to General Method B: LC-MS Method D (ESI+) m/z 342.0 (M+H)$^+$, retention time 1.36 minutes.

Example 96

4-(6'-methoxy-3,3'-bipyridin-5-yl)-1,4-diazatricyclo[4.3.1.1$^{3,8}$]undecane

The title compound was prepared from the product of Example 65A and 2-methoxypyridin-5-ylboronic acid according to General Method B: LC-MS Method D (ESI+) m/z 337.0 (M+H)$^+$, retention time 1.23 minutes.

Example 97

4-[5-(2-methoxy-5-methylphenyl)pyridin-3-yl]-1,4-diazatricyclo[4.3.1.1$^{3,8}$]undecane The title compound was prepared from the product of Example 65A and 2-methoxy-5-methylboronic acid according to General Method B: LC-MS Method D (ESI+) m/z 350.0 (M+H)$^+$, retention time 1.41 minutes.

Example 98

4-[5-(4-methoxy-3-methylphenyl)pyridin-3-yl]-1,4-diazatricyclo[4.3.1.1$^{3,8}$]undecane The title compound was prepared from the product of Example 65A and 4-methoxy-3-methylphenylboronic acid according to General Method B: LC-MS Method D (ESI+) m/z 350.0 (M+H)$^+$, retention time 1.42 minutes.

Example 99

4-[5-(3,4-difluorophenyl)pyridin-3-yl]-1,4-diazatricyclo[4.3.1.1$^{3,8}$]undecane The title compound was prepared from the product of Example 65A and 3,4-difluorophenylboronic acid according to General Method B: LC-MS Method D (ESI+) m/z 336.0 (M+H)$^+$, retention time 1.30 minutes.

Example 100

1-{5-[5-(1,4-diazatricyclo[4.3.1.1$^{3,8}$]undec-4-yl)pyridin-3-yl]thien-2-yl}ethanone The title compound was prepared from the product of Example 65A and 5-acetylthiophen-2-ylboronic acid according to General Method B: LC-MS Method D (ESI+) m/z 354.0 (M+H)$^+$, retention time 1.26 minutes.

Example 101

4-(5-pyrimidin-5-ylpyridin-3-yl)-1,4-diazatricyclo[4.3.1.1$^{3,8}$]undecane

The title compound was prepared from the product of Example 65A and pyrimidin-5-ylboronic acid according to General Method B: LC-MS Method B (ESI+) m/z 308.0 (M+H)$^+$, retention time 1.45 minutes.

Example 102

1-{2-[5-(1,4-diazatricyclo[4.3.1.1$^{3,8}$]undec-4-yl)pyridin-3-yl]phenyl}ethanone The title compound was prepared from the product of Example 65A and 2-acetylphenylboronic acid according to General Method B: LC-MS Method D (ESI+) m/z 348.0 (M+H)$^+$, retention time 1.26 minutes.

Example 103

4-[5-(1H-indol-5-yl)pyridin-3-yl]-1,4-diazatricyclo[4.3.1.1$^{3,8}$]undecane

The title compound was prepared from the product of Example 65A and 1H-indol-5-ylboronic acid according to General Method B: LC-MS Method D (ESI+) m/z 344.0 (M+H)$^+$, retention time 1.30 minutes.

Example 104

4-[5-(1H-indol-4-yl)pyridin-3-yl]-1,4-diazatricyclo[4.3.1.1$^{3,8}$]undecane

The title compound was prepared from the product of Example 65A and 1H-indol-4-ylboronic acid according to General Method B: LC-MS Method D (ESI+) m/z 344.0 (M+H)$^+$, retention time 1.27 minutes.

Example 105

4-[5-(4-methoxyphenyl)-1,3-thiazol-2-yl]-1,4-diazatricyclo[4.3.1.1$^{3,8}$]undecane

Example 105A 4-(5-bromo-1,3-thiazol-2-yl)-1,4-diazatricyclo[4.3.1.1$^{3,8}$]undecane To a solution of the product of Example 2 (1 g, 6.55 mmol) in toluene (50 mL) under nitrogen was added 2,5-dibromothiazole (3.18 g, 13.1 mmol), potassium carbonate (1.80 g, 13.1 mmol), 2,2'-bis(diphenylphosphino)-1,1'-binaphthyl (403 mg, 0.655 mmol) and palladium(II) acetate (74 mg, 0.328 mmol). The mixture was stirred overnight at reflux. After cooling, the reaction mixture was concentrated under reduced pressure and the residue was purified by chromatography on silica gel (1:2 petroleum ether-ethyl acetate) to afford the title compound: $^1$H NMR (500 MHz, CDCl$_3$) δ ppm 7.40 (s, 1H), 4.75-4.71 (m, 1H), 3.64-3.59 (q, 2H), 3.48-3.40 (q, 2H), 3.08-3.05 (m, 4H), 2.29-2.18 (m, 3H), 1.88-1.80 (m, 3H).

Example 105B

4-[5-(4-methoxyphenyl)-1,3-thiazol-2-yl]-1,4-diazatricyclo[4.3.1.1$^{3,8}$]undecane The title compound was prepared from the product of Example 105A and 4-methoxyphenylboronic acid according to General Method C: $^1$H NMR (500 MHz, CDCl$_3$) δ ppm 7.35 (d, 2 H), 7.28 (s, 1 H), 6.88 (d, 2 H), 4.75-4.71 (m, 1 H), 3.64-3.59 (q, 2 H), 3.48-3.40 (q, 2 H), 3.08-3.05 (m, 4 H), 2.29-2.18 (m, 3 H), 1.88-1.80 (m, 3 H); LC-MS Method D (ESI+) m/z 342.0 (M+H)⁺, retention time 1.44 minutes.

Example 106

4-[5-(4-methylphenyl)-1,3-thiazol-2-yl]-1,4-diazatricyclo[4.3.1.1³,⁸]undecane

The title compound was prepared from the product of Example 105A and 4-methylphenylboronic acid according to General Method C: LC-MS Method D (ESI+) m/z 326.0 (M+H)⁺, retention time 1.54 minutes.

Example 107

4-[5-(3-methylphenyl)-1,3-thiazol-2-yl]-1,4-diazatricyclo[4.3.1.1³,⁸]undecane

The title compound was prepared from the product of Example 105A and 3-methylphenylboronic acid according to General Method C: LC-MS Method D (ESI+) m/z 326.0 (M+H)⁺, retention time 1.55 minutes.

Example 108

4-[5-(3-fluorophenyl)-1,3-thiazol-2-yl]-1,4-diazatricyclo[4.3.1.1³,⁸]undecane

The title compound was prepared from the product of Example 105A and 3-fluorophenylboronic acid according to General Method C: LC-MS Method D (ESI+) m/z 330.0 (M+H)⁺, retention time 1.55 minutes.

Example 109

4-[5-(2,5-dimethoxyphenyl)-1,3-thiazol-2-yl]-1,4-diazatricyclo[4.3.1.1³,⁸]undecane The title compound was prepared from the product of Example 105A and 2,5-dimethoxyphenylboronic acid according to General Method C: LC-MS Method D (ESI+) m/z 372.0 (M+H)⁺, retention time 1.44 minutes.

Example 110

4-[5-(4-fluorophenyl)-1,3-thiazol-2-yl]-1,4-diazatricyclo[4.3.1.1³,⁸]undecane

The title compound was prepared from the product of Example 105A and 4-fluorophenylboronic acid according to General Method C: LC-MS Method D (ESI+) m/z 330.0 (M+H)⁺, retention time 1.51 minutes.

Example 111

4-(6-chloro-1,3-benzothiazol-2-yl)-1,4-diazatricyclo[4.3.1.1³,⁸]undecane

A mixture of the product of Example 2 (25 mg, 0.16 mmol), 2,6-dichloro-1,3-benzothiazole (40 mg, 0.19 mmol), tris(dibenzylideneacetone)dipalladium(0) (9 mg), 2,2'-bis(diphenylphosphino)-1,1'-binaphthyl (12 mg) and sodium tert-butoxide (22 mg, 0.38 mmol) in toluene (7 mL) was stirred at 85° C. overnight. After the reaction mixture was concentrated under vacuum, the residue was purified by preparative HPLC [Mobile Phase A=water (10 mM NH₄HCO₃), B=acetonitrile, Gradient: 30-60% B in 9 minutes) to afford the title compound: ¹H NMR (500 MHz, D₂O) δ ppm 7.63 (d, 1 H), 7.37 (t, 1 H), 7.32 (t, 1 H), 4.64 (br, 1 H), 3.94-3.84 (m, 3 H), 3.78-3.66 (m, 5 H), 2.83 (s, 1 H), 2.39-2.31 (m, 3 H), 2.02-1.87 (m, 2 H); LC-MS Method D (ESI+) m/z 320.0 (M+H)⁺, retention time 1.61 minutes.

Example 112

4-(6-chloro-1,3-benzoxazol-2-yl)-1,4-diazatricyclo[4.3.1.1³,⁸]undecane

A mixture of the product of Example 2 (40 mg, 0.26 mmol) and 2,6-dichloro-1,3-benzoxazole (30 mg, 0.16 mmol) in ethanol (6 mL) was stirred at 85° C. for 45 minutes under microwave irradiation (Biotage Initiator™ Sixty EXP, 375 W maximum). After removal of the solvent, the residue was purified by prep-TLC(CHCl₃-CH₃OH=20:1) to afford the title compound: LC-MS Method A (ESI+) m/z 304.0 (M+H)⁺, retention time 1.23 minutes.

Example 113

4-(1,3-benzothiazol-2-yl)-1,4-diazatricyclo[4.3.1.1³,⁸]undecane

A mixture of the product of Example 2 (35 mg, 0.23 mmol) and 2-chloro-1,3-benzothiazole (33 mg, 0.20 mmol) in ethanol (6 mL) was stirred at 85° C. for 45 minutes under microwave irradiation (Biotage Initiator™ Sixty EXP, 375 W maximum). After concentration of the reaction mixture, the residue was purified by prep-TLC(CHCl₃-CH₃OH=20:1) to afford the title compound: ¹H NMR (500 MHz, D₂O) δ ppm 7.96 (d, 2 H), 7.56 (t, 1 H), 7.50 (t, 1 H), 4.23-4.04 (m, 6 H), 3.6-3.0 (m, 3 H), 2.61-1.73 (m, 6 H); LC-MS Method D (ESI+) m/z 286.0 (M+H)⁺, retention time 1.23 minutes.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:
1. A compound of formula (I)

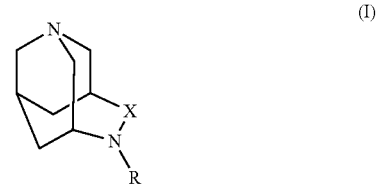

wherein
X is CH₂ or C═O;
R is hydrogen, Ar¹, Ar²—Ar³, —(CH₂)$_q$Ar³, —C(O)Ar³, —C(O)OAr³, —C(O)NR¹R², —C(O)—(CR$^x$R$^y$)$_q$—Ar³, —C(O)—(CR$^x$R$^y$)$_q$—O—Ar³, —C(O)—Ar²—Ar³, or (i);

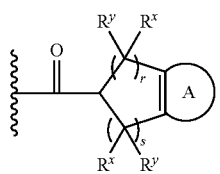

(i)

Ar¹, Ar², and Ar³ are each independently aryl or heteroaryl;
A is aryl or heteroaryl;
q is 1, 2, 3, 4, or 5;
r and s are independently 0, 1, 2, or 3, wherein the total of r and s is 2, 3 or 4;
R¹ is hydrogen or alkyl;
R² is aryl, arylalkyl, heteroaryl, or heteroarylalkyl;
$R^x$ and $R^y$, at each occurrence, are each independently hydrogen, alkyl, fluorine, or haloalkyl;
wherein each aryl or heteroaryl or the aryl and heteroaryl moieties on arylalkyl and heteroarylalkyl groups are independently unsubstituted or substituted with 1, 2, 3, 4, or 5 substituents selected from the group consisting of alkyl, alkenyl, alkynyl, halogen, cyano, -G¹, —NO₂, —OR¹ᵃ, —O—(CR⁴ᵃR⁵ᵃ)ₚ—O—, —OC(O)R¹ᵃ, —OC(O)N(Rᵇ)(R³ᵃ), —SR¹ᵃ, —S(O)₂R²ᵃ, —S(O)₂N(Rᵇ)(R³ᵃ), —C(O)R¹ᵃ, —C(O)OR¹ᵃ, —C(O)N(Rᵇ)(R³ᵃ), —N(Rᵇ)(R³ᵃ), —N(Rᵃ)C(O)R¹ᵃ, —N(Rᵃ)C(O)O(R¹ᵃ), —N(Rᵃ)C(O)N(Rᵇ)(R³ᵃ), —(CR⁴ᵃR⁵ᵃ)ₘ—NO₂, —(CR⁴ᵃR⁵ᵃ)ₘ—OR¹ᵃ, —(CR⁴ᵃR⁵ᵃ)ₘ—OC(O)R¹ᵃ, —(CR⁴ᵃR⁵ᵃ)ₘ—OC(O)N(Rᵇ)(R³ᵃ), —(CR⁴ᵃR⁵ᵃ)ₘ—SR¹ᵃ, —(CR⁴ᵃR⁵ᵃ)ₘ—S(O)₂R²ᵃ, —(CR⁴ᵃR⁵ᵃ)S(O)₂N(Rᵇ)(R³ᵃ), —(CR⁴ᵃR⁵ᵃ)ₘ—C(O)R¹ᵃ, —(CR⁴ᵃR⁵ᵃ)ₘ—C(O)OR¹ᵃ, —(CR⁴ᵃR⁵ᵃ)ₘ—C(O)N(Rᵇ)(R³ᵃ), —(CR⁴ᵃR⁵ᵃ)ₘ—N(Rᵇ)(R³ᵃ), —(CR⁴ᵃR⁵ᵃ)ₘ—N(Rᵃ)C(O)R¹ᵃ, —(CR⁴ᵃR⁵ᵃ)ₘ—N(Rᵃ)C(O)O(R¹ᵃ), —(CR⁴ᵃR⁵ᵃ)ₘ—N(Rᵃ)C(O)N(Rᵇ)(R³ᵃ), —(CR⁴ᵃR⁵ᵃ)ₘ-G², cyanoalkyl, and haloalkyl; wherein R¹ᵃ and R³ᵃ, at each occurrence, are each independently hydrogen, alkyl, haloalkyl, G², or —(CR⁶ᵃR⁷ᵃ)ₙ-G²;
R²ᵃ, at each occurrence, is independently alkyl, haloalkyl, G², or —(CR⁶ᵃR⁷ᵃ)ₙ-G²;
R⁴ᵃ, R⁵ᵃ, R⁶ᵃ, and R⁷ᵃ, at each occurrence, are each independently hydrogen, halogen, alkyl, or haloalkyl;
Rᵃ and Rᵇ, at each occurrence, are each independently hydrogen, alkyl, or haloalkyl;
m and n, at each occurrence, are each independently 1, 2, 3, 4, or 5;
p, at each occurrence, is 1 or 2;
—O—(CR⁴ᵃR⁵ᵃ)ₚ—O— is a divalent substituent attached to two adjacent carbon atoms of the aryl or heteroaryl;
G¹, at each occurrence, is heterocycle or cycloalkyl, wherein each G¹ is independently unsubstituted or substituted with 1, 2, 3, 4, or 5 substituents selected from the group consisting of alkyl, alkenyl, alkynyl, halogen, cyano, oxo, —NO₂, —OR¹ᵇ, —OC(O)R¹ᵇ, —OC(O)N(Rᵇ)(R³ᵇ), —SR¹ᵇ, —S(O)₂R²ᵇ, S(O)₂N(Rᵇ)(R³ᵇ), —C(O)R¹ᵇ, —C(O)OR¹ᵇ, —C(O)N(Rᵇ)(R³ᵇ), —N(Rᵇ)(R³ᵇ), —N(Rᵃ)C(O)R¹ᵇ, —N(Rᵃ)C(O)O(R¹ᵇ), —N(Rᵃ)C(O)N(Rᵇ)(R³ᵇ), —(CR⁴ᵇR⁵ᵇ)ₘ—NO₂, —(CR⁴ᵇR⁵ᵇ)ₘ—OR¹ᵇ, —(CR⁴ᵇR⁵ᵇ)ₘ—OC(O)R¹ᵇ, —(CR⁴ᵇR⁵ᵇ)ₘ—OC(O)N(Rᵇ)(R³ᵇ), —(CR⁴ᵇR⁵ᵇ)ₘ—SR¹ᵇ, —(CR⁴ᵇR⁵ᵇ)ₘ—S(O)₂R²ᵇ, —(CR⁴ᵇR⁵ᵇ)ₘ—S(O)₂N(Rᵇ)(R³ᵇ), —(CR⁴ᵇR⁵ᵇ)ₘ—C(O)R¹ᵇ, —(CR⁴ᵇR⁵ᵇ)ₘ—C(O)OR¹ᵇ, —(CR⁴ᵇR⁵ᵇ)ₘ—C(O)N(Rᵇ)(R³ᵇ), —(CR⁴ᵇR⁵ᵇ)ₘ—N(Rᵇ)(R³ᵇ), —(CR⁴ᵇR⁵ᵇ)ₘ—N(Rᵃ)C(O)R¹ᵇ, —(CR⁴ᵇR⁵ᵇ)ₘ—N(Rᵃ)C(O)O(R¹ᵇ), —(CR⁴ᵇR⁵ᵇ)ₘ—N(Rᵃ)C(O)N(Rᵇ)(R³ᵇ), cyanoalkyl, and haloalkyl;

R¹ᵇ and R³ᵇ, at each occurrence, are each independently hydrogen, alkyl, or haloalkyl;
R²ᵇ, at each occurrence, is independently alkyl or haloalkyl;
R⁴ᵇ and R⁵ᵇ, at each occurrence, are each independently hydrogen, halogen, alkyl, or haloalkyl; and
G², at each occurrence, is aryl, heteroaryl, heterocycle, or cycloalkyl, wherein each G² is independently unsubstituted or substituted with 1, 2, 3, 4, or 5 substituents selected from the group consisting of alkyl, alkenyl, alkynyl, halogen, cyano, oxo, —NO₂, —OR¹ᵇ, —OC(O)R¹ᵇ, —OC(O)N(Rᵇ)(R³ᵇ), —SR¹ᵇ, —S(O)₂R²ᵇ, —S(O)₂N(Rᵇ)(R³ᵇ), —C(O)R¹ᵇ, —C(O)OR¹ᵇ, —C(O)N(Rᵇ)(R³ᵇ), —N(Rᵇ)(R³ᵇ), —N(Rᵃ)C(O)R¹ᵇ, —N(Rᵃ)C(O)O(R¹ᵇ), —N(Rᵃ)C(O)N(Rᵇ)(R³ᵇ), —(CR⁴ᵇR⁵ᵇ)ₘ—NO₂, —(CR⁴ᵇR⁵ᵇ)ₘ—OR¹ᵇ, —(CR⁴ᵇR⁵ᵇ)ₘ—OC(O)R¹ᵇ, —(CR⁴ᵇR⁵ᵇ)ₘ—OC(O)N(Rᵇ)(R³ᵇ), —(CR⁴ᵇR⁵ᵇ)ₘ—SR¹ᵇ, —(CR⁴ᵇR⁵ᵇ)ₘ—S(O)₂R²ᵇ, —(CR⁴ᵇR⁵ᵇ)ₘ—S(O)₂N(Rᵇ)(R³ᵇ), —(CR⁴ᵇR⁵ᵇ)ₘ—C(O)R¹ᵇ, —(CR⁴ᵇR⁵ᵇ)ₘ—C(O)OR¹ᵇ, —(CR⁴ᵇR⁵ᵇ)ₘ—C(O)N(Rᵇ)(R³ᵇ), —(CR⁴ᵇR⁵ᵇ)ₘ—N(Rᵇ)(R³ᵇ), —(CR⁴ᵇR⁵ᵇ)ₘ—N(Rᵃ)C(O)R¹ᵇ, —(CR⁴ᵇR⁵ᵇ)ₘ—N(Rᵃ)C(O)O(R¹ᵇ), —(CR⁴ᵇR⁵ᵇ)ₘ—N(Rᵃ)C(O)N(Rᵇ)(R³ᵇ), cyanoalkyl, and haloalkyl;

or a pharmaceutically acceptable salt, amide, or ester thereof.

2. The compound of claim 1, wherein R is Ar¹.

3. The compound of claim 2, wherein X is CH₂, and Ar¹ is a bicyclic or tricyclic heteroaryl optionally oxidized on an oxidizable nitrogen or sulfur and either unsubstituted or substituted with 1, 2, or 3 substituents selected from halogen or alkyl.

4. The compound of claim 1, wherein R is Ar²—Ar³ or —C(O)—Ar²—Ar³.

5. The compound of claim 4, wherein
X is CH₂,
Ar² is heteroaryl selected from oxadiazolyl, pyridazinyl, pyrazolyl, pyridinyl, thiadiazolyl or 1,3-thiazolyl;
Ar³ is phenyl or heteroaryl, wherein the phenyl or heteroaryl is unsubstituted or substituted with 1, 2, 3, or 4 substituents selected from alkyl, halogen, cyano, —OR¹ᵃ, —O—(CR⁴ᵃR⁵ᵃ)ₚ—O—, —C(O)R¹ᵃ, —N(Rᵇ)(R³ᵃ), —N(Rᵃ)C(O)R¹ᵃ, or haloalkyl; wherein
R¹ᵃ and R³ᵃ, at each occurrence, are each independently alkyl or haloalkyl;
R⁴ᵃ and R⁵ᵃ, at each occurrence, are each independently hydrogen or alkyl; and
Rᵇ, at each occurrence, are each independently hydrogen, alkyl, or haloalkyl.

6. The compound of claim 1, wherein R is —C(O)Ar³ or —C(O)OAr³.

7. The compound of claim 6, wherein
X is CH₂;
Ar³ is phenyl or heteroaryl, wherein heteroaryl is selected from pyridinyl, furanyl, benzofuranyl, indolyl, thienyl, benzothienyl, pyrazinyl, quinolinyl, pyrrolyl, thieno[3,2-b]pyridin-5-yl or indazolyl, and wherein the phenyl or heteroaryl is unsubstituted or substituted with 1, 2, 3, or 4 substituents selected from alkyl, halogen, cyano, —OR¹ᵃ, —N(Rᵇ)(R³ᵃ), —N(Rᵃ)C(O)R¹ᵃ, or haloalkyl;

wherein
R$^{1a}$ and R$^{3a}$, at each occurrence, are each independently alkyl or haloalkyl; and
R$^b$ is hydrogen, alkyl, or haloalkyl.

8. The compound of claim 1, wherein R is —(CH$_2$)$_q$Ar$^3$.
9. The compound of claim 1, wherein R is —C(O)NR$^1$R$^2$.
10. The compound of claim 1, wherein R is —C(O)—(CR$^x$R$^y$)$_q$—Ar$^3$ or —C(O)—(CR$^x$R$^y$)$_q$—O—Ar$^3$.
11. The compound of claim 10, wherein
X is CH$_2$;
R$^x$ and R$^y$, at each occurrence, are each independently hydrogen or alkyl;
q is 1 or 2;
Ar$^3$ is phenyl, naphthyl or thienyl, wherein the phenyl, naphthyl or thienyl is unsubstituted or substituted with 1, 2, 3, or 4 substituents selected from alkyl, halogen, cyano, —OR$^{1a}$, —N(R$^b$)(R$^{3a}$), —N(R$^a$)C(O)R$^{1a}$, or haloalkyl; wherein
R$^{1a}$ and R$^{3a}$, at each occurrence, are each independently alkyl or haloalkyl; and
R$^b$ is hydrogen, alkyl, or haloalkyl.
12. The compound of claim 1, wherein R is (i)

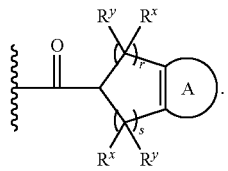

(i)

13. The compound of claim 12, wherein
X is CH$_2$;
A is phenyl;
R$^x$ and R$^y$, at each occurrence, are each independently hydrogen or alkyl; and
r and s are independently 0, 1, or 2, wherein the total of r and s is 2 or 3.
14. The compounds of claim 1, wherein R is hydrogen.
15. The compound of claim 14, that is selected from the group consisting of:
1,4-diazatricyclo[4.3.1.1$^{3,8}$]undecan-5-one; and
1,4-diazatricyclo[4.3.1.1$^{3,8}$]undecane.
16. A compound or pharmaceutically salt thereof, or amide thereof, the compound is selected from the group consisting of:
4-(thieno[2,3-c]pyridin-5-ylcarbonyl)-1,4-diazatricyclo[4.3.1.1$^{3,8}$]undecane;
4-(thieno[3,2-b]pyridin-5-ylcarbonyl)-1,4-diazatricyclo[4.3.1.1$^{3,8}$]undecane;
4-(5,5-dioxidodibenzo[b,d]thien-3-yl)-1,4-diazatricyclo[4.3.1.1$^{3,8}$]undecane;
4-(5-phenyl-1,3,4-oxadiazol-2-yl)-1,4-diazatricyclo[4.3.1.1$^{3,8}$]undecane;
4-(6-phenylpyridazin-3-yl)-1,4-diazatricyclo[4.3.1.1$^{3,8}$]undecane;
4-[6-(1-benzothien-5-yl)pyridazin-3-yl]-1,4-diazatricyclo[4.3.1.1$^{3,8}$]undecane;
4-(3-methoxybenzoyl)-1,4-diazatricyclo[4.3.1.1$^{3,8}$]undecane;
4-(1-naphthylacetyl)-1,4-diazatricyclo[4.3.1.1$^{3,8}$]undecane;
4-(pyridin-2-ylcarbonyl)-1,4-diazatricyclo[4.3.1.1$^{3,8}$]undecane;
4-(phenoxyacetyl)-1,4-diazatricyclo[4.3.1.1$^{3,8}$]undecane;
4-(3-chlorobenzoyl)-1,4-diazatricyclo[4.3.1.1$^{3,8}$]undecane;
N-[4-(1,4-diazatricyclo[4.3.1.1$^{3,8}$]undec-4-ylcarbonyl)phenyl]-N,N-dimethylamine;
4-[(2-methylphenyl)acetyl]-1,4-diazatricyclo[4.3.1.1$^{3,8}$]undecane;
3-(1,4-diazatricyclo[4.3.1.1$^{3,8}$]undec-4-ylcarbonyl)benzonitrile;
4-(2-methylbenzoyl)-1,4-diazatricyclo[4.3.1.1$^{3,8}$]undecane;
N-[4-(1,4-diazatricyclo[4.3.1.1$^{3,8}$]undec-4-ylcarbonyl)phenyl]acetamide;
4-[(3-methylphenyl)acetyl]-1,4-diazatricyclo[4.3.1.1$^{3,8}$]undecane;
4-(2,5-dimethylbenzoyl)-1,4-diazatricyclo[4.3.1.1$^{3,8}$]undecane;
4-(3-phenylpropanoyl)-1,4-diazatricyclo[4.3.1.1$^{3,8}$]undecane;
N-[3-(1,4-diazatricyclo[4.3.1.1$^{3,8}$]undec-4-ylcarbonyl)phenyl]acetamide;
4-(4-ethylbenzoyl)-1,4-diazatricyclo[4.3.1.1$^{3,8}$]undecane;
4-{[2-(trifluoromethyl)phenyl]acetyl}-1,4-diazatricyclo[4.3.1.1$^{3,8}$]undecane;
4-(2,4-dimethylbenzoyl)-1,4-diazatricyclo[4.3.1.1$^{3,8}$]undecane;
4-(3-phenylbutanoyl)-1,4-diazatricyclo[4.3.1.1$^{3,8}$]undecane;
4-(1,2,3,4-tetrahydronaphthalen-2-ylcarbonyl)-1,4-diazatricyclo[4.3.1.1$^{3,8}$]undecane;
4-(4-ethoxybenzoyl)-1,4-diazatricyclo[4.3.1.1$^{3,8}$]undecane;
N-{4-[2-(1,4-diazatricyclo[4.3.1.1$^{3,8}$]undec-4-yl)-2-oxoethyl]phenyl}-N,N-dimethylamine;
4-(2,3-difluorobenzoyl)-1,4-diazatricyclo[4.3.1.1$^{3,8}$]undecane;
4-(3-methylbenzoyl)-1,4-diazatricyclo[4.3.1.1$^{3,8}$]undecane;
4-(2,5-dimethyl-3-furoyl)-1,4-diazatricyclo[4.3.1.1$^{3,8}$]undecane;
4-(pyridin-3-ylcarbonyl)-1,4-diazatricyclo[4.3.1.1$^{3,8}$]undecane;
4-(5-chloro-2-fluorobenzoyl)-1,4-diazatricyclo[4.3.1.1$^{3,8}$]undecane;
4-(3-methyl-2-furoyl)-1,4-diazatricyclo[4.3.1.1$^{3,8}$]undecane;
4-[(1-phenyl-1H-pyrazol-5-ylcarbonyl]-1,4-diazatricyclo[4.3.1.1$^{3,8}$]undecane;
4-(1H-indol-5-ylcarbonyl)-1,4-diazatricyclo[4.3.1.1$^{3,8}$]undecane;
4-(3,5-dimethoxybenzoyl)-1,4-diazatricyclo[4.3.1.1$^{3,8}$]undecane;
4-[(4-methylthien-2-yl)carbonyl]-1,4-diazatricyclo[4.3.1.1$^{3,8}$]undecane;
4-[(2,5-dimethoxyphenyl)acetyl]-1,4-diazatricyclo[4.3.1.1$^{3,8}$]undecane;
4-[(5-methylthien-2-yl)carbonyl]-1,4-diazatricyclo[4.3.1.1$^{3,8}$]undecane;
4-(2-fluorobenzoyl)-1,4-diazatricyclo[4.3.1.1$^{3,8}$]undecane;
4-[(2-fluorophenyl)acetyl]-1,4-diazatricyclo[4.3.1.1$^{3,8}$]undecane;
4-[4-(trifluoromethyl)benzoyl]-1,4-diazatricyclo[4.3.1.1$^{3,8}$]undecane;
4-(3,4-difluorobenzoyl)-1,4-diazatricyclo[4.3.1.1$^{3,8}$]undecane;
4-(thien-2-ylcarbonyl)-1,4-diazatricyclo[4.3.1.1$^{3,8}$]undecane;

4-[(5-methylpyrazin-2-yl)carbonyl]-1,4-diazatricyclo[4.3.1.1$^{3,8}$]undecane;
4-(2,3-dimethylbenzoyl)-1,4-diazatricyclo[4.3.1.1$^{3,8}$]undecane;
4-(quinolin-2-ylcarbonyl)-1,4-diazatricyclo[4.3.1.1$^{3,8}$]undecane;
4-(thien-2-ylacetyl)-1,4-diazatricyclo[4.3.1.1$^{3,8}$]undecane;
4-[(3-methoxyphenyl)acetyl]-1,4-diazatricyclo[4.3.1.1$^{3,8}$]undecane;
4-[(1-methyl-1H-pyrrol-2-yl) carbonyl]-1,4-diazatricyclo[4.3.1.1$^{3,8}$]undecane;
2-(1,4-diazatricyclo[4.3.1.1$^{3,8}$]undec-4-ylcarbonyl)phenol;
4-[(2-methoxypyridin-3-yl) carbonyl]-1,4-diazatricyclo[4.3.1.1$^{3,8}$]undecane;
4-(1H-pyrrol-2-ylcarbonyl)-1,4-diazatricyclo[4.3.1.1$^{3,8}$]undecane;
4-(3-chloro-4-fluorobenzoyl)-1,4-diazatricyclo[4.3.1.1$^{3,8}$]undecane;
4-(1H-indazol-3-ylcarbonyl)-1,4-diazatricyclo[4.3.1.1$^{3,8}$]undecane;
4-(5-chloro-2-methoxybenzoyl)-1,4-diazatricyclo[4.3.1.1$^{3,8}$]undecane;
4-(2,4-difluorobenzoyl)-1,4-diazatricyclo[4.3.1.1$^{3,8}$]undecane;
4-(thien-3-ylacetyl)-1,4-diazatricyclo[4.3.1.1$^{3,8}$]undecane;
4-(4-fluoro-3-methylbenzoyl)-1,4-diazatricyclo[4.3.1.1$^{3,8}$]undecane;
4-(2-furoyl)-1,4-diazatricyclo[4.3.1.1$^{3,8}$]undecane;
4-benzoyl-1,4-diazatricyclo[4.3.1.1$^{3,8}$]undecane;
4-(2-methoxybenzoyl)-1,4-diazatricyclo[4.3.1.1$^{3,8}$]undecane;
4-[5-(3-fluoro-4-methoxyphenyl)pyridin-3-yl]-1,4-diazatricyclo[4.3.1.1$^{3,8}$]undecane;
4-[5-(2,3-dihydro-1,4-benzodioxin-6-yl)pyridin-3-yl]-1,4-diazatricyclo[4.3.1.1$^{3,8}$]undecane;
N-{4-[5-(1,4-diazatricyclo[4.3.1.1$^{3,8}$]undec-4-yl)pyridin-3-yl]phenyl}-N,N-dimethylamine;
4-[5-(3,4,5-trimethoxyphenyl)pyridin-3-yl]-1,4-diazatricyclo[4.3.1.1$^{3,8}$]undecane;
4-[5-(3,5-dimethylisoxazol-4-yl)pyridin-3-yl]-1,4-diazatricyclo[4.3.1.1$^{3,8}$]undecane;
4-[5-(2,6-dimethoxyphenyl)pyridin-3-yl]-1,4-diazatricyclo[4.3.1.1$^{3,8}$]undecane;
4-(5-phenylpyridin-3-yl)-1,4-diazatricyclo[4.3.1.1$^{3,8}$]undecane;
4-[5-(4-methylphenyl)pyridin-3-yl]-1,4-diazatricyclo[4.3.1.1$^{3,8}$]undecane;
4-[5-(4-fluorophenyl)pyridin-3-yl]-1,4-diazatricyclo[4.3.1.1$^{3,8}$]undecane;
4-[5-(4-methoxyphenyl)pyridin-3-yl]-1,4-diazatricyclo[4.3.1.1$^{3,8}$]undecane;
4-{5-[4-(trifluoromethyl)phenyl]pyridin-3-yl}-1,4-diazatricyclo[4.3.1.1$^{3,8}$]undecane;
4-[5-(3-methylphenyl)pyridin-3-yl]-1,4-diazatricyclo[4.3.1.1$^{3,8}$]undecane;
4-[5-(3-fluorophenyl)pyridin-3-yl]-1,4-diazatricyclo[4.3.1.1$^{3,8}$]undecane;
4-[5-(3-methoxyphenyl)pyridin-3-yl]-1,4-diazatricyclo[4.3.1.1$^{3,8}$]undecane;
4-[5-(2-furyl)pyridin-3-yl]-1,4-diazatricyclo[4.3.1.1$^{3,8}$]undecane;
4-(5-thien-3-ylpyridin-3-yl)-1,4-diazatricyclo[4.3.1.1$^{3,8}$]undecane;
4-[5-(3,4-dimethoxyphenyl)pyridin-3-yl]-1,4-diazatricyclo[4.3.1.1$^{3,8}$]undecane;
4-(3,3'-bipyridin-5-yl)-1,4-diazatricyclo[4.3.1.1$^{3,8}$]undecane;
4-(3,4'-bipyridin-5-yl)-1,4-diazatricyclo[4.3.1.1$^{3,8}$]undecane;
4-[5-(2-methoxyphenyl)pyridin-3-yl]-1,4-diazatricyclo[4.3.1.1$^{3,8}$]undecane;
4-[5-(2,5-dimethoxyphenyl)pyridin-3-yl]-1,4-diazatricyclo[4.3.1.1$^{3,8}$]undecane;
4-[5-(2,4-dimethoxyphenyl)pyridin-3-yl]-1,4-diazatricyclo[4.3.1.1$^{3,8}$]undecane;
4-[5-(2-fluorophenyl)pyridin-3-yl]-1,4-diazatricyclo[4.3.1.1$^{3,8}$]undecane;
4-[5-(2-ethoxyphenyl)pyridin-3-yl]-1,4-diazatricyclo[4.3.1.1$^{3,8}$]undecane;
4-[5-(1,4-diazatricyclo[4.3.1.1$^{3,8}$]undec-4-yl)pyridin-3-yl]benzonitrile;
3-[5-(1,4-diazatricyclo[4.3.1.1$^{3,8}$]undec-4-yl)pyridin-3-yl]benzonitrile;
4-{5-[3-(trifluoromethyl)phenyl]pyridin-3-yl}-1,4-diazatricyclo[4.3.1.1$^{3,8}$]undecane;
4-[5-(1,3-benzodioxol-5-yl)pyridin-3-yl]-1,4-diazatricyclo[4.3.1.1$^{3,8}$]undecane;
4-(2'-methoxy-3,3'-bipyridin-5-yl)-1,4-diazatricyclo[4.3.1.1$^{3,8}$]undecane;
N-{3-[5-(1,4-diazatricyclo[4.3.1.1$^{3,8}$]undec-4-yl)pyridin-3-yl]phenyl}acetamide;
4-[5-(3,5-difluorophenyl)pyridin-3-yl]-1,4-diazatricyclo[4.3.1.1$^{3,8}$]undecane;
4-(6'-methoxy-3,3'-bipyridin-5-yl)-1,4-diazatricyclo[4.3.1.1$^{3,8}$]undecane;
4-[5-(2-methoxy-5-methylphenyl)pyridin-3-yl]-1,4-diazatricyclo[4.3.1.1$^{3,8}$]undecane;
4-[5-(4-methoxy-3-methylphenyl)pyridin-3-yl]-1,4-diazatricyclo[4.3.1.1$^{3,8}$]undecane;
4-[5-(3,4-difluorophenyl)pyridin-3-yl]-1,4-diazatricyclo[4.3.1.1$^{3,8}$]undecane;
1-{5-[5-(1,4-diazatricyclo[4.3.1.1$^{3,8}$]undec-4-yl)pyridin-3-yl]thien-2-yl}ethanone;
4-(5-pyrimidin-5-ylpyridin-3-yl)-1,4-diazatricyclo[4.3.1.1$^{3,8}$]undecane;
1-{2-[5-(1,4-diazatricyclo[4.3.1.1$^{3,8}$]undec-4-yl)pyridin-3-yl]phenyl}ethanone;
4-[5-(1H-indol-5-yl)pyridin-3-yl]-1,4-diazatricyclo[4.3.1.1$^{3,8}$]undecane;
4-[5-(1H-indol-4-yl)pyridin-3-yl]-1,4-diazatricyclo[4.3.1.1$^{3,8}$]undecane;
4-[5-(4-methoxyphenyl)-1,3-thiazol-2-yl]-1,4-diazatricyclo[4.3.1.1$^{3,8}$]undecane;
4-[5-(4-methylphenyl)-1,3-thiazol-2-yl]-1,4-diazatricyclo[4.3.1.1$^{3,8}$]undecane;
4-[5-(3-methylphenyl)-1,3-thiazol-2-yl]-1,4-diazatricyclo[4.3.1.1$^{3,8}$]undecane;
4-[5-(3-fluorophenyl)-1,3-thiazol-2-yl]-1,4-diazatricyclo[4.3.1.1$^{3,8}$]undecane;
4-[5-(2,5-dimethoxyphenyl)-1,3-thiazol-2-yl]-1,4-diazatricyclo[4.3.1.1$^{3,8}$]undecane;
4-[5-(4-fluorophenyl)-1,3-thiazol-2-yl]-1,4-diazatricyclo[4.3.1.1$^{3,8}$]undecane;
4-(6-chloro-1,3-benzothiazol-2-yl)-1,4-diazatricyclo[4.3.1.1$^{3,8}$]undecane;
4-(6-chloro-1,3-benzoxazol-2-yl)-1,4-diazatricyclo[4.3.1.1$^{3,8}$]undecane; and
4-(1,3-benzothiazol-2-yl)-1,4-diazatricyclo[4.3.1.1$^{3,8}$]undecane.

17. A method for treating a disorder selected from the group consisting of acute pain, chronic pain, neuropathic pain, nociceptive pain, allodynia, inflammatory pain, neuralgia, rheumatoid arthritic pain, osteoarthritic pain, back pain, eye pain, cancer pain, dental pain, pelvic pain, post operative pain, post stroke pain, and menstrual pain, said method comprising the step of administering to a subject in need thereof the compound of claim 16, or a pharmaceutically acceptable salt, or amide thereof.

18. A method for treating a disorder selected from the group consisting of schizophrenia and Alzheimer's disease, comprising the step of administering to a subject in need thereof the compound of claim 16, or a pharmaceutically acceptable salt, or amide thereof and one or more atypical antipsychotics.

19. A pharmaceutical composition comprising a therapeutically effective amount of the compound of claim 16, or a pharmaceutically acceptable salt, or amide thereof in combination with one or more pharmaceutically acceptable carriers.

20. The pharmaceutical composition of claim 19 further comprising one or more atypical antipsychotics.

\* \* \* \* \*